(12) United States Patent
Lesage et al.

(10) Patent No.: US 7,517,517 B2
(45) Date of Patent: Apr. 14, 2009

(54) RADIOLABELLED QUINOLINE AND QUINOLINONE DERIVATIVES AND THEIR USE AS METABOTROPIC GLUTAMATE RECEPTOR LIGANDS

(75) Inventors: Anne Simone Josephine Lesage, Halle-Zoersel (BE); François Paul Bischoff, Vosselaar (BE); Cornelus Gerardus Maria Janssen, Vosselaar (BE); Hilde Lavreysen, Lommel (BE)

(73) Assignee: Janssen Pharmaceutica N.V., Beerse (BE)

( * ) Notice: Subject to any disclaimer, the term of this patent is extended or adjusted under 35 U.S.C. 154(b) by 453 days.

(21) Appl. No.: 10/509,069

(22) PCT Filed: Mar. 26, 2003

(86) PCT No.: PCT/EP03/03240

§ 371 (c)(1),
(2), (4) Date: Sep. 24, 2004

(87) PCT Pub. No.: WO03/082350

PCT Pub. Date: Oct. 9, 2003

(65) Prior Publication Data
US 2006/0083676 A1 Apr. 20, 2006

(30) Foreign Application Priority Data
Mar. 29, 2002 (EP) .................. 02076254

(51) Int. Cl.
A61K 51/00 (2006.01)
A61M 36/14 (2006.01)
G01N 33/00 (2006.01)

(52) U.S. Cl. ..................... 424/1.11; 435/7.93
(58) Field of Classification Search ................. 424/1.11
See application file for complete search history.

(56) References Cited

U.S. PATENT DOCUMENTS

| 4,931,270 | A |   | 6/1990 | Horn et al. |
| 5,441,963 | A | * | 8/1995 | McDonald et al. .......... 514/311 |
| 5,541,325 | A | * | 7/1996 | Freyne et al. ............. 544/363 |
| 5,597,922 | A | * | 1/1997 | Cai et al. ................ 544/354 |
| 5,958,919 | A | * | 9/1999 | Olney et al. ............. 514/214.03 |
| 6,001,331 | A | * | 12/1999 | Caprathe et al. ............ 424/9.1 |

FOREIGN PATENT DOCUMENTS

| JP | 2000169450 A | 6/2000 |
| WO | WO 9427605 A | 12/1994 |
| WO | WO 96 05818 A | 2/1996 |
| WO | WO 9903822 A | 1/1999 |
| WO | WO 9926927 A | 6/1999 |
| WO | WO 0228837 A | 4/2002 |

| WO | WO 0228837 A1 * | 4/2002 |

OTHER PUBLICATIONS

Stone T.W., "Development and therapeutic potential of kynurenic acid and kynurenine derivatives for neuroprotection," Trends in Pharmacological Scienses, Elsevier Trends Journal, vol. 21, No. 4, Apr. 2000, pp. 149-154.

(Continued)

Primary Examiner—Michael G. Hartley
Assistant Examiner—Melissa Perreira
(74) Attorney, Agent, or Firm—Woodcock Wshburn LLP

(57) ABSTRACT

The present invention is concerned with radiolabelled quinoline and quinolinone derivatives according Formula (I-A)* or (I-B)* showing metabotropic glutamate receptor antagonistic activity, in particular mGlu1 receptor activity, and their preparation; it further relates to compositions comprising them, as well as their use for marking and identifying metabotropic glutamate receptor sites and for imaging an organ.

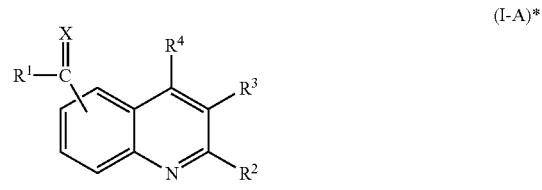

(I-A)*

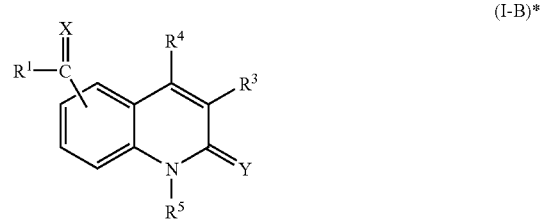

(I-B)*

Figure 1:
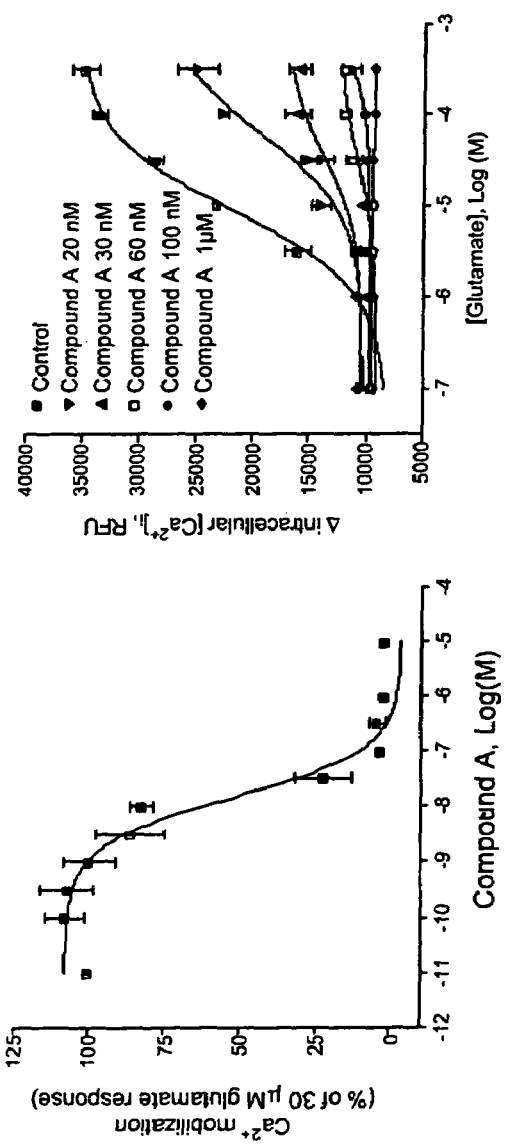

In a preferable embodiment, X represents O; $R^1$ represents $C_{1-6}$alkyl; cyclo$C_{3-12}$alkyl or (cyclo$C_{3-12}$alkyl)$C_{1-6}$alkyl, wherein one or more hydrogen atoms in a $C_{1-6}$alkyl-moiety or in a cyclo$C_{3-12}$alkyl-moiety optionally may be replaced by $C_{1-6}$alkyloxy, aryl, halo or thienyl; $R^2$ represents hydrogen; halo; $C_{1-6}$alkyl or amino; $R^3$ and $R^4$ each independently represent hydrogen or $C_{1-6}$alkyl; or $R^2$ and $R^3$ may be taken together to form $-R^2-R^3-$, which represents a bivalent radical of formula $-Z_4-CH_2-CH_2-CH_2-$ or $-Z_4-CH_2-CH_2-$ with $Z_4$ being O or $NR^{11}$ wherein $R^{11}$ is $C_{1-6}$alkyl; and wherein each bivalent radical is optionally substituted with $C_{1-6}$alkyl; or $R^3$ and $R^4$ may be taken together to form a bivalent radical of formula $-CH_2-CH_2-CH_2-CH_2-$; $R^5$ represents hydrogen; Y represents O; and aryl represents phenyl optionally substituted with halo. Most preferred are radiolabelled compounds in which the radioactive isotope is selected from the group of of $^3H$, $^{11}C$ and $^{18}F$. The invention also relates to their use in a diagnostic method, in particular for marking and identifying a mGluR1 receptor in biological material, as well as to their use for imaging an organ, in particular using PET.

21 Claims, 10 Drawing Sheets

OTHER PUBLICATIONS

Sing-Yuen S et al., "3-Hydroxy-quinolin-2-ones: inhibitors of Hl-glycine binding to the site associated with the NMDA receptor," *Bioorganic & Medicinal Chemistry Letters*, vol. 6, No. 5, Mar. 5, 1996, pp. 499-504.

Dabhi T.P. et al., "Potential antimicrobial Agents: Synthesis of N,N-Diaryl/N,N-Dialkyl/N-Aryl-N-Alkyl-(2-Aryl/Styrl-6-Acetylquinolin-4-YL)-Formadies," *Indian Journal of Heterocyclic Chemistry*, vol. 2, No. 2 Oct. 1992 (pp. 137-138).

Bhatt D.J. et al., "Studies on Chalcones: Preparation and Antimicrobial Activityof 2-aryl-4-carboxy-6-acetylquinoline and 2-aryl-4-carboxy-6- benzalacetoquinolines," *Journal of the Indian Chemical Society*, The Indian Chemical Society, vol. 61, No. 9, Sep. 1984, pp. 816-818.

Mutel Vincent et al., "Characterization of (3H) quisqualate binding to recombinant rat metabotropic glutamate 1a and 5a receptors and to rat and human brain sections," *Journal of Neurochemistry*, vol. 75, No. 6, Dec. 2000, pp. 2590-2601.

Peng C. T. et al., "An Evaluation of Different Methods for Tritium Labelling," *Fusion Technology*, American Nuclear Society, vol. 21, No. 2, pt. 2, pp. 307-311, Mar. 1, 1992.

Brundish et al., "Tritium labeling by selective debromination," *Journal of Labelled Compounds and Radio pharmaceuticals*, Sussex, GB, vol. 25, No. 12, 1988, pp. 1361-1369.

Thomsen et al.,"A Pharmacological characterization of the MgluR1α subtype of the metabotorpic glutamate receptor expressed in a cloned baby hamster kidney cell line," *Brain Res*. 619:22-28, 1993.

Kingston, A.E., et al., "Sulphur-containing amino acids are agonists for group 1 metabotropic receptors expressed in clonal RGT cell lines," *Neuropharmacology* 37:277-287, 1998.

Mutel et al., "Characterization of [3H] Quisqualate Binding to Recombinant Rat Metabotropic Glutamate 1a and 5a Receptors and to Rat and Human Brain Sections," *J. Neurochem.* 75:2590-2601, 2000.

Scott, W.J. et al., "Palladium-Catalyzed Coupline of Vinyl Triflates with Organostannanes. A short Synthesis of Pleraplysillin-1," *J. Am. Chem. Soc.*, 1984, 106, 4630.

Lavreysen et al., "Supersensitivityof Human Metabotropic Glutamate 1a Receptor Signaling in L929sA Cells," *Mol. Pharmacol.* 61:1244-1254, 2002.

Cheng et al., "Relationship Between the Inhibition Constant ($K_1$) and the Concentration of Inhibitor Which Causes 50 Per Cent Inhibition (I50) of an Enzymatic Reaction," *Biochem. Pharmacol.* 22, 3099-3108, 1973.

Litschig et al., "CPCOEt, a Noncompetitive Metabotropic Glutamate Receptor 1 Antagonist, Inhyibits Receptor Signaling Without Affecting Glutamate Binding," *Molecular Pharmacol*, 55:453-461, 1999.

Zhu et al., "The Competitive and Noncompetitive Antagonism of Recepotr-Mediated Drug Actions in the Presence of Spare Receptors," *J.Pharm. Tox. Meth*. 29:85-91, 1993).

Carroll et al., "BAY36-7620: A Potent Non-Competitive mGlu1 Receptor Antagonist with Inverse Agonist Activity," *Mol. Pharmacol*. 59:965-973, 2001.

Hermans et al., "Reversible and non-competitive antagonist profile of CPCCOEt at the human type 1α metabotropic glutamate receptor," *Neuropharmacology* 37:1645-1647 , 1998.

van de Waterbeemd et al., "Molecular electrostatic Potential of Orthopramides: Implications for Their Interaction with the D-2 Dopamine Receptor," *J.Med. Chem*. 29:600-606, 1986.

Schoepp et al., "1S,3R-ACPD-sensitive (metabotropic) [$^3$H]glutamate receptor binding in membranes," *Neurosci. Lett* 145:100-104, 1992.

Wright et al., "Distribution and Ontogeny of 1S,3R-1-Aminocyclopentane-1,3-Dicarboxylic Acid-Sensitive and Quisqualate-Insensitive [3H]Glutamate Binding Sites in the Rat Brain," *J. Neurochem*. 63:938-945, 1994.

Lujan et al., "Perisynaptic Location of Metabotropic Glutamate Receptors mGluR1 and MgluR5 on Dendrites and Dendritic Spines in the Rat Hippocampus," *Eur.J.Neurosci*. 8:1488-1500, 1996.

Shigemoto et al., "Differential Presynaptic Localization of Metabotropic Glutamate Receptor Subtypes in the Rat Hippocampus," *J. Neurosci*. 17:7503-7522, 1997.

Martin et al., "Cellular Localizationof a Metabotropic Glutamate Receptor in Rat Brain," *Neuron*. 9:259-270, 1992.

Ferraguti et al., "Immunohistochemical Localization of the mGluR1α Metabotropic Glutamate Receptor in the Adult Rodent Forebrain: Evidence for a Differential Distribution of mGluR1 Splice Variants," *J. Comp. Neur*. 400:391-407, 1998.

PCT Search Report for PCT/EP03/03240 dated Sep. 23, 2003.

* cited by examiner

RADIOLABELLED QUINOLINE AND QUINOLINONE DERIVATIVES AND THEIR USE AS METABOTROPIC GLUTAMATE RECEPTOR LIGANDS

CROSS REFERENCE TO RELATED APPLICATIONS

This application is the national stage of Application No. PCT/EP03/03240, filed Mar. 26, 2003, which application claims priority from EP 02076254.8 filed Mar. 29, 2002.

FIELD OF THE INVENTION

The present invention is concerned with radiolabelled quinoline and quinolinone derivatives showing metabotropic glutamate receptor antagonistic activity, in particular mGlu1 receptor activity, and their preparation; it further relates to compositions comprising them, as well as their use in a diagnostic method, in particular for marking and identifying metabotropic glutamate receptor sites and for imaging an organ.

INTRODUCTION

The neurotransmitter glutamate is considered to be the major excitatory neurotransmitter in the mammalian central nervous system. The binding of this neurotransmitter to metabotropic glutamate receptors (mGluRs), which are a subfamily of the G-protein-coupled receptors and which comprise 8 distinct subtypes of mGluRs, namely mGluR1 through mGluR8, activates a variety of intracellular second messenger systems. The mGluRs can be divided into 3 groups based on amino acid sequence homology, the second messenger system utilized by the receptors and the pharmacological characteristics. Group I mGluRs, which comprises mGluR subtype 1 and 5, couple to phospholipase C and their activation leads to intracellular calcium-ion mobilization. Group II mGluRs (mGluR2 and 3) and group III mGluRs (mGluR4, 6, 7 and 8) couple to adenyl cyclase and their activation causes a reduction in second messenger cAMP and as such a dampening of the neuronal activity. Treatment with Group I mGluR antagonists has been shown to translate in the parasynapsis into a reduced release of neurotransmitter glutamate and to decrease the glutamate-mediated neuronal excitation via postsynaptic mechanisms. Since a variety of pathophysiologic processes and disease states affecting the central nervous system are thought to be due to excessive glutamate induced excitation of the central nervous system neurons, Group I mGluR antagonists, in particular mGluR1 antagonists could be therapeutically beneficial in the treatment of central nervous system diseases, in particular in psychiatric and neurological diseases.

However, up to now, no specific mGluR1-ligands were available, a lack severely hampering the study of the mGlu1 receptors, in particular the radioautographic investigations of the unequivocal distribution and abundance of these receptors in brain sections. For group I, only [$^3$H]glutamate was available so far, being used on rat (Thomsen et al., *Brain Res.* 619:22-28, 1993) or human (Kingston et al., *Neuropharmacology* 37:277-287, 1998) mGlu1a receptors. For the mGlu1a receptor and the mGlu5 receptor [$^3$H]quisqualate is available, however, said receptor is not specific for the mGlu1 receptor (it also binds to the AMPA receptor) and it is competitive, i.e. it displaces glutamate (Mutel at al., *J. Neurochem.* 75:2590-2601, 2000).

It has been the goal of this invention to provide suitable specific, in particular non-competitive mGlu1 receptor ligands.

SUMMARY OF THE INVENTION

The inventors have now found a particular group of compounds that—in a radiolabelled form—provides for suitable specific, in particular non-competitive mGlu1 receptor ligands as well as a method for marking and identifying metabotropic glutamate receptor sites and for imaging an organ.

In the framework of this application, the term "specific" means that the ligand binds preferentially to the mGlu1 receptor site. The term "non-competitive" means that the ligand does not or only marginally displaces glutamate bonded to the mGlu1 receptor site.

WO 02/28837 discloses the non-radioactive compounds according to the present invention.

WO 99/26927 discloses antagonists of Group I mGluRs for treating neurological diseases and disorders, based—among others—on a quinoline structure.

WO 99/03822 discloses bicyclic metabotropic glutamate receptor ligands, none of them based on a quinoline or quinolinone structure.

WO 94/27605 discloses 1,2,3,4-tetrahydroquinoline-2,3,4-trione-3 or 4-oximes and use thereof for treating and preventing neuronal loss, neurodegenerative diseases, adverse consequences of the hyperactivity of the excitatory amino acids and anxiety, as well as radiolabelled compounds thereof.

DETAILED DESCRIPTION OF THE INVENTION

The present invention concerns the radiolabelled compounds of Formula (I-A)* or (I-B)*

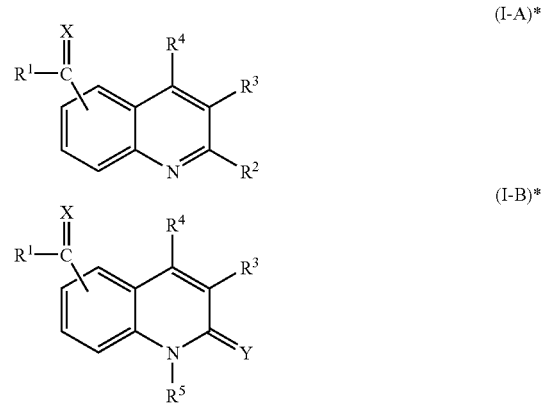

an N-oxide form, a pharmaceutically acceptable addition salt, a quaternary amine and a stereochemical isomeric form thereof, wherein X represents O; C(R$^6$)$_2$ with R$^6$ being hydrogen, aryl or C$_{1-6}$alkyl optionally substituted with amino or mono- or di(C$_{1-6}$alkyl)amino; S or N—R$^7$ with R$^7$ being amino or hydroxy;

R$^1$ represents C$_{1-6}$alkyl; aryl; thienyl; quinolinyl; cycloC$_{3-12}$ alkyl or (cycloC$_{3-12}$alkyl)C$_{1-6}$alkyl, wherein the cyclo C$_{3-12}$alkyl moiety optionally may contain a double bond and wherein one carbon atom in the cycloC$_{3-12}$alkyl moiety may be replaced by an oxygen atom or an NR$^8$-moiety with $R^8$ being hydrogen, benzyl or $C_{1-6}$alkyloxycarbonyl; wherein one or more hydrogen atoms in a $C_{1-6}$alkyl-moiety or in a cyclo$C_{3-12}$alkyl-moiety optionally may be replaced by $C_{1-6}$alkyl, hydroxy$C_{1-6}$alkyl, halo$C_{1-6}$alkyl, amino$C_{1-6}$alkyl, hydroxy, $C_{1-6}$alkyloxy, aryl$C_{1-6}$alkyloxy, halo, $C_{1-6}$alkyloxycarbonyl, aryl, amino, mono- or di($C_{1-6}$alkyl)amino, $C_{1-6}$alkyloxycarbonylamino, halo, piperazinyl, pyridinyl, morpholinyl, thienyl or a bivalent radical of formula —O—, —O—$CH_2$—O or —O—$CH_2$—$CH_2$—O—; or a radical of formula (a-1)

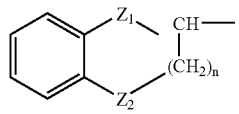

(a-1)

wherein $Z_1$ is a single covalent bond, O, NH or $CH_2$;
$Z_2$ is a single covalent bond, O, NH or $CH_2$;
n is an integer of 0, 1, 2 or 3;
and wherein each hydrogen atom in the phenyl ring independently may optionally be replaced by halo, hydroxy, $C_{1-6}$alkyl, $C_{1-6}$alkyloxy or hydroxy$C_{1-6}$alkyl;

or X and $R^1$ may be taken together with the carbon atom to which X and $R^1$ are attached to form a radical of formula (b-1), (b-2) or (b-3);

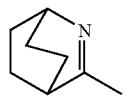

(b-1)

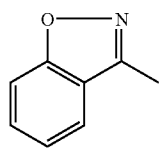

(b-2)

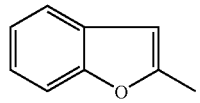

(b-3)

$R^2$ represents hydrogen; halo; cyano; $C_{1-6}$alkyl; $C_{1-6}$alkyloxy; $C_{1-6}$alkylthio; $C_{1-6}$alkylcarbonyl; $C_{1-6}$alkyloxycarbonyl; $C_{1-6}$alkylcarbonyloxy$C_{1-6}$alkyl; $C_{2-6}$alkenyl; hydroxy$C_{2-6}$alkenyl; $C_{2-6}$alkynyl; hydroxy$C_{2-6}$alkynyl; tri($C_{1-6}$alkyl)silane$C_{2-6}$alkynyl; amino; mono- or di($C_{1-6}$alkyl)amino; mono- or di($C_{1-6}$alkyloxy$C_{1-6}$alkyl)amino; mono- or di($C_{1-6}$alkylthio$C_{1-6}$alkyl)amino; aryl; aryl$C_{1-6}$alkyl; aryl$C_{2-6}$alkynyl; $C_{1-6}$alkyloxy$C_{1-6}$alkylamino$C_{1-6}$alkyl; aminocarbonyl optionally substituted with $C_{1-6}$alkyl, $C_{1-6}$alkyloxy$C_{1-6}$alkyl, $C_{1-6}$alkyloxycarbonyl$C_{1-6}$alkyl or pyridinyl$C_{1-6}$alkyl;

a heterocycle selected from thienyl, furanyl, pyrrolyl, thiazolyl, oxazolyl, imidazolyl, isothiazolyl, isoxazolyl, pyrazolyl, pyridyl, pyrazinyl, pyridazinyl, pyrimidinyl, piperidinyl and piperazinyl, optionally N-substituted with $C_{1-6}$alkyloxy$C_{1-6}$alkyl, morpholinyl, thiomorpholinyl, dioxanyl or dithianyl;

a radical —NH—C(=O)$R^9$ wherein $R^9$ represents $C_{1-6}$alkyl optionally substituted with cyclo$C_{3-12}$alkyl, $C_{1-6}$alkyloxy, $C_{1-6}$alkyloxycarbonyl, aryl, aryloxy, thienyl, pyridinyl, mono- or di($C_{1-6}$alkyl)amino, $C_{1-6}$alkylthio, benzylthio, pyridinylthio or pyrimidinylthio;

cyclo$C_{3-12}$alkyl; cyclohexenyl; amino; arylcyclo$C_{3-12}$ alkylamino; mono- or -di($C_{1-6}$alkyl)amino; mono- or di($C_{1-6}$alkyloxycarbonyl$C_{1-6}$alkyl)amino; mono- or di($C_{1-6}$alkyloxycarbonyl)amino; mono- or di($C_{2-6}$alkenyl)amino; mono- or di(aryl$C_{1-6}$alkyl)amino; mono- or diarylamino; aryl$C_{2-6}$alkenyl; furanyl$C_{2-6}$alkenyl; piperididinyl; piperazinyl; indolyl; furyl; benzofuryl; tetrahydrofuryl; indenyl; adamantyl; pyridinyl; pyrazinyl; aryl; aryl$C_{1-6}$alkylthio or a radical of formula (a-1);

a sulfonamid —NH—$SO_2$—$R^{10}$ wherein $R^{10}$ represents $C_{1-6}$alkyl, mono- or poly halo$C_{1-6}$alkyl, aryl$C_{1-6}$alkyl, aryl$C_{2-6}$alkenyl, aryl, quinolinyl, isoxazolyl or di($C_{1-6}$alkyl)amino;

$R^3$ and $R^4$ each independently represent hydrogen; halo; hydroxy; cyano; $C_{1-6}$alkyl; $C_{1-6}$alkyloxy; $C_{1-6}$alkyloxy$C_{1-6}$ alkyl; $C_{1-6}$alkylcarbonyl; $C_{1-6}$alkyloxycarbonyl; $C_{2-6}$alkenyl; hydroxy$C_{2-6}$alkenyl; $C_{2-6}$alkynyl; hydroxy$C_{2-6}$alkynyl; tri($C_{1-6}$alkyl)silane$C_{2-6}$alkynyl; amino; mono- or di($C_{1-6}$alkyl)amino; mono- or di($C_{1-6}$alkyloxy$C_{1-6}$alkyl)amino; mono- or di($C_{1-6}$alkylthio$C_{1-6}$alkyl)amino; aryl; morpholinyl$C_{1-6}$alkyl or piperidinyl$C_{1-6}$ alkyl; or $R^2$ and $R^3$ may be taken together to form —$R^2$—$R^3$—, which represents a bivalent radical of formula —$(CH_2)_3$—, —$(CH_2)_4$—, —$(CH_2)_5$—, —$(CH_2)_6$—, —CH=CH—CH=CH—, -$Z_4$-CH=CH—, —CH=CH-$Z_4$-, -$Z_4$-$CH_2$—$CH_2$—$CH_2$—, —$CH_2$-$Z_4$-$CH_2$—$CH_2$—, —$CH_2$—$CH_2$-$Z_4$-$CH_2$—, —$CH_2$—$CH_2$—$CH_2$-$Z_4$-, -$Z_4$-$CH_2$—$CH_2$—, —$CH_2$-$Z_4$-$CH_2$— or —$CH_2$—$CH_2$-$Z_4$-, with $Z_4$ being O, S, $SO_2$ or $NR^{11}$ wherein $R^{11}$ is hydrogen, $C_{1-6}$alkyl, benzyl or $C_{1-6}$alkyloxycarbonyl; and wherein each bivalent radical is optionally substituted with $C_{1-6}$alkyl.

or $R^3$ and $R^4$ may be taken together to form a bivalent radical of formula —CH=CH—CH=CH— or —$CH_2$—$CH_2$—$CH_2$—$CH_2$—;

$R^5$ represents hydrogen; cyclo$C_{3-12}$alkyl; piperidinyl; oxothienyl; tetrahydrothienyl; aryl$C_{1-6}$alkyl; $C_{1-6}$alkyloxy$C_{1-6}$ alkyl; $C_{1-6}$alkyloxycarbonyl$C_{1-6}$alkyl or $C_{1-6}$alkyl optionally substituted with a radical C(=O)$NR_xR_y$, in which $R_x$ and $R_y$ each independently are hydrogen, cyclo$C_{3-12}$alkyl, $C_{2-6}$alkynyl or $C_{1-6}$alkyl optionally substituted with cyano, $C_{1-6}$alkyloxy, $C_{1-6}$alkyloxycarbonyl, furanyl, pyrrolidinyl, benzylthio, pyridinyl, pyrrolyl or thienyl;

Y represents O or S;
or Y and $R^5$ may be taken together to form =Y—$R^5$— which represents a radical of formula —CH=N—N= (c-1);

—N=N—N= (c-2); or

—N—CH=CH— (c-3);

aryl represents phenyl or naphthyl optionally substituted with one or more substituents selected from halo, hydroxy, $C_{1-6}$alkyl, $C_{1-6}$alkyloxy, phenyloxy, nitro, amino, thio, $C_{1-6}$alkylthio, halo$C_{1-6}$alkyl, polyhalo$C_{1-6}$alkyl, polyhalo$C_{1-6}$alkyloxy, hydroxy$C_{1-6}$alkyl, $C_{1-6}$alkyloxy$C_{1-6}$alkyl, amino$C_{1-6}$alkyl, mono- or di($C_{1-6}$alkyl)amino, mono- or di($C_{1-6}$alkyl)amino$C_{1-6}$alkyl, cyano, —CO—$R^{12}$, —CO—$OR^{13}$, —$NR^{13}SO_2R^{12}$, —$SO_2$—$NR^{13}R^{14}$, —$NR^{13}$C(O)$R^{12}$, —C(O)$NR^{13}R^{14}$, —$SOR^{12}$, —$SO_2R^{12}$; wherein each $R^{12}$, $R^{13}$ and $R^{14}$ independently represent $C_{1-6}$alkyl; cyclo$C_{3-6}$alkyl; phenyl; phenyl substituted with halo, hydroxy, $C_{1-6}$alkyl, $C_{1-6}$alkyloxy, halo$C_{1-6}$alkyl, polyhalo$C_{1-6}$alkyl, furanyl, thienyl, pyrrolyl, imidazolyl, thiazolyl or oxazolyl;

and when the $R^1$—C(=X) moiety is linked to another position than the 7 or 8 position, then said 7 and 8 position may be substituted with $R^{15}$ and $R^{16}$ wherein either one or both of $R^{15}$ and $R^{16}$ represents $C_{1-6}$alkyl, $C_{1-6}$alkyloxy or $R^{15}$ and $R^{16}$ taken together may form a bivalent radical of formula —CH=CH—CH=CH—.

As used in the foregoing definitions and hereinafter $C_{1-6}$alkyl as a group or part of a group encompasses the straight and branched chain saturated hydrocarbon radicals having from 1 to 6 carbon atoms such as, for example, methyl, ethyl, propyl, butyl, pentyl or hexyl; $C_{2-6}$alkenyl as a group or part of a group encompasses the straight and branched chain hydrocarbon radicals having from 2 to 6 carbon atoms and having a double bond such as ethenyl, propenyl, butenyl, pentenyl, hexenyl, 3-methylbutenyl and the like; $C_{2-6}$alkynyl as a group or part of a group defines straight or branched chain hydrocarbon radicals having from 2 to 6 carbon atoms and having a triple bond such as ethynyl, propynyl, butynyl, pentynyl, hexynyl, 3-methylbutynyl and the like; cyclo$C_{3-6}$alkyl encompasses monocyclic alkyl ring structures such as cyclopropyl, cyclobutyl, cyclopentyl, and cyclohexyl; cyclo$C_{3-12}$alkyl encompasses mono-, bi- or tricyclic alkyl ring structures and is generic to for example cyclopropyl, cyclobutyl, cyclopentyl, cyclohexyl, cycloheptyl, cyclooctyl, norbornanyl, adamantyl.

The term halo is generic to fluoro, chloro, bromo and iodo. As used in the foregoing and hereinafter, polyhalo$C_{1-6}$alkyl as a group or part of a group is defined as mono- or polyhalosubstituted $C_{1-6}$alkyl, in particular methyl with one or more fluoro atoms, for example, difluoromethyl or trifluoromethyl. In case more than one halogen atoms are attached to an alkyl group within the definition of polyhalo$C_{1-6}$alkyl, they may be the same or different.

When any variable, e.g. aryl, occurs more than one time in any constituent, each definition is independent.

When any bond is drawn into a ring structure, it means that the corresponding substituent may be linked to any atom of said ring structure. This means for instance that the $R^1$—C(=X) moiety may be linked to the quinoline or quinolinone moiety in position 5, 6, 7, 8 but also position 3 or position 4.

By the term "radiolabelled compound" is meant any compound according to Formula (I-A)* or (I-B)*, an N-oxide form, a pharmaceutically acceptable addition salt, a quaternary amine or a stereochemically isomeric form thereof, which contains at least one radioactive atom. In the framework of this application, compounds which do not contain a radio-active atom are denoted without an asterisk to their formula number, compounds which contain a radio-active atom are denoted with an asterisk to their formula number. Compounds can be labelled with either positron or gamma emitting radionuclides. For radioligand-binding techniques (membrane receptor assay), the [$^3$H]-atom or the [$^{125}$I]-atom is the atom of choice. For imaging, the most commonly used positron emitting (PET) radionuclides are $^{11}$C, $^{18}$F, $^{15}$O and $^{13}$N, all of which are accelerator produced and have half-lives of 20, 100, 2 and 10 minutes respectively. Since the half-lives of these radionuclides are so short, it is only feasible to use them at institutions which have an accelerator on site for their production, thus limiting their use. The most widely used of these are $^{18}$F, $^{99m}$Tc, $^{201}$Tl and $^{123}$I.

In particular, the radioactive atom is selected from the group of hydrogen, carbon, nitrogen, sulfur, oxygen and halogen. Preferably, the radioactive atom is selected from the group of hydrogen, carbon and halogen.

In particular, the radioactive atom is selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive atom is selected from the group of $^3$H, $^{11}$C and $^{18}$F.

By the term "compound according to the invention" is meant a compound according to Formula (I-A)* or (I-B)*, an N-oxide form, a pharmaceutically acceptable addition salt, a quaternary amine and a stereochemically isomeric form thereof.

For in vivo use, salts of the compounds of Formula (I-A)* and (I-B)* are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention. With the term "in vivo" is meant any use of the compounds according to the invention whereby said compounds are administered to live animals.

The pharmaceutically acceptable addition salts as mentioned hereinabove are meant to comprise the therapeutically active non-toxic acid addition salt forms which the compounds of Formula (I-A)* and (I-B)* are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of Formula (I-A)* and (I-B)* containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethyl amine, propyl amine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term "addition salt" also comprises the hydrates and solvent addition forms which the compounds of Formula (I-A)* and (I-B)* are able to form. Examples of such forms are e.g. hydrates, alcoholates and the like.

The term "quaternary amine" as used hereinbefore defines the quaternary ammonium salts which the compounds of Formula (I-A)* and (I-B)* are able to form by reaction between a basic nitrogen of a compound of Formula (I-A)* or (I-B)* and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counter ions include chloro, bromo, iodo, trifluoroacetate and acetate. The counter ion of choice can be introduced using ion exchange resins.

It will be appreciated that some of the compounds according to the invention may contain one or more centers of chirality and exist as stereochemically isomeric forms.

The term "stereochemically isomeric forms" as used hereinbefore defines all the possible stereoisomeric forms which the compounds according to the invention or physiologically functional derivatives may possess. Unless otherwise mentioned or indicated, the chemical designation of compounds denotes the mixture of all possible stereoisomeric forms, said mixtures containing all diastereomers and enantiomers of the basic molecular structure as well as each of the individual isomeric forms of the compounds according to the invention, substantially free, i.e. associated with less than 10%, preferably less than 5%, in particular less than 2% and most preferably less than 1% of the other isomers. Stereochemically isomeric forms of the compounds according to the invention are obviously intended to be embraced within the scope of the present invention. The same applies to the intermediates as described herein, used to prepare end products of the compounds according to the invention.

The terms cis and trans are used herein in accordance with Chemical Abstracts nomenclature.

In some compounds according to the invention and in the intermediates used in their preparation, the absolute stereochemical configuration has not been determined. In these cases, the stereoisomeric form which was first isolated is designated as "A" and the second as "B", without further reference to the actual stereochemical configuration. However, said "A" and "B" stereoisomeric forms can be unambiguously characterized by physicochemical characteristics such as their optical rotation in case "A" and "B" have an enantiomeric relationship. A person skilled in the art is able to determine the absolute configuration of such compounds using art-known methods such as, for example, X-ray diffraction. In case "A" and "B" are stereoisomeric mixtures, they can be further separated whereby the respective first fractions isolated are designated "A1" and "B1" and the second as "A2" and "B2", without further reference to the actual stereochemical configuration.

The N-oxide forms of the present compounds are meant to comprise the compounds of formula (I-A)* and (I-B)* wherein one or several nitrogen atoms are oxidized to the so-called N-oxide.

Some of the compounds according to the invention may also exist in their tautomeric form. Such forms although not explicitly indicated in the above formula are intended to be included within the scope of the present invention. Of special interest are those compounds of formula (I-A)* and (I-B)* which are stereochemically pure.

An interesting group of compounds are those compounds of formula (I-A)* and (I-B)* wherein X represents O; C($R^6$)$_2$ with $R^6$ being hydrogen or aryl; or N—$R^7$ with $R^7$ being amino or hydroxy;

$R^1$ represents $C_{1-6}$alkyl, aryl; thienyl; quinolinyl; cyclo$C_{3-12}$alkyl or (cyclo$C_{3-12}$alkyl)$C_{1-6}$alkyl, wherein the cyclo $C_{3-12}$alkyl moiety optionally may contain a double bond and wherein one carbon atom in the cyclo$C_{3-12}$alkyl moiety may be replaced by an oxygen atom or an N$R^8$-moiety with $R^8$ being benzyl or $C_{1-6}$alkyloxycarbonyl; wherein one or more hydrogen atoms in a $C_{1-6}$alkyl-moiety or in a cyclo$C_{3-12}$alkyl-moiety optionally may be replaced by $C_{1-6}$alkyl, halo$C_{1-6}$alkyl, hydroxy, $C_{1-6}$alkyloxy, aryl$C_{1-6}$alkyloxy, halo, aryl, mono- or di($C_{1-6}$alkyl)amino, $C_{1-6}$alkyloxycarbonylamino, halo, piperazinyl, pyridinyl, morpholinyl, thienyl or a bivalent radical of formula —O— or —O—CH$_2$—CH$_2$—O—; or a radical of formula (a-1)

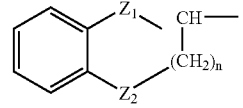

a-1 wherein $Z_1$ is a single covalent bond, O or CH$_2$;
$Z_2$ is a single covalent bond, O or CH$_2$;
n is an integer of 0, 1, or 2;
and wherein each hydrogen atom in the phenyl ring independently may optionally be replaced by halo or hydroxy;

or X and $R^1$ may be taken together with the carbon atom to which X and $R^1$ are attached to form a radical of formula (b-1), (b-2) or (b-3);

b-1

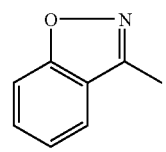

b-2

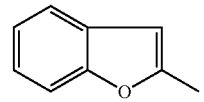

b-3

$R^2$ represents hydrogen; halo; cyano; $C_{1-6}$alkyl; $C_{1-6}$alkyloxy; $C_{1-6}$alkylthio; $C_{1-6}$alkylcarbonyl; $C_{1-6}$alkyloxycarbonyl; $C_{2-6}$alkenyl; hydroxy$C_{2-6}$alkenyl; $C_{2-6}$alkynyl; hydroxy$C_{2-6}$alkynyl; tri($C_{1-6}$alkyl)silane$C_{2-6}$alkynyl; amino; mono- or di($C_{1-6}$alkyl)amino; mono- or di($C_{1-6}$alkyloxy$C_{1-6}$alkyl)amino; mono- or di($C_{1-6}$alkylthio$C_{1-6}$alkyl)amino; aryl; aryl$C_{1-6}$alkyl; aryl$C_{2-6}$alkynyl; $C_{1-6}$alkyloxy$C_{1-6}$alkylamino$C_{1-6}$alkyl;

aminocarbonyl optionally substituted with $C_{1-6}$alkyloxycarbonyl$C_{1-6}$alkyl; a heterocycle selected from thienyl, furanyl, thiazolyl and piperidinyl, optionally N-substituted with morpholinyl or thiomorpholinyl;

a radical —NH—C(=O)$R^9$ wherein $R^9$ represents $C_{1-6}$alkyl optionally substituted with cyclo$C_{3-12}$alkyl, $C_{1-6}$alkyloxy, $C_{1-6}$alkyloxycarbonyl, aryl, aryloxy, thienyl, pyridinyl, mono- or di($C_{1-6}$alkyl)amino, $C_{1-6}$alkylthio, benzylthio, pyridinylthio or pyrimidinylthio; cyclo$C_{3-12}$alkyl; cyclohexenyl; amino; arylcyclo$C_{3-12}$alkylamino; mono- or -di($C_{1-6}$alkyl)amino; mono- or di($C_{1-6}$alkyloxycarbonyl$C_{1-6}$alkyl)amino; mono- or di($C_{1-6}$alkyloxycarbonyl)amino; mono- or di($C_{2-6}$alkenyl)amino; mono- or di(aryl$C_{1-6}$alkyl)amino; mono- or diarylamino; aryl$C_{2-6}$alkenyl; furanyl$C_{2-6}$alkenyl; piperidinyl; piperazinyl; indolyl; furyl; benzofuryl; tetrahydrofuryl; indenyl; adamantyl; pyridinyl; pyrazinyl; aryl or a radical of formula (a-1);

a sulfonamid —NH—SO$_2$—R$^{10}$ wherein R$^{10}$ represents C$_{1-6}$alkyl, mono- or poly haloC$_{1-6}$alkyl, arylC$_{1-6}$alkyl or aryl;

R$^3$ and R$^4$ each independently represent hydrogen; C$_{1-6}$alkyl; C$_{1-6}$alkyloxyC$_{1-6}$alkyl; C$_{1-6}$alkyloxycarbonyl; or R$^2$ and R$^3$ may be taken together to form —R$^2$—R$^3$—, which represents a bivalent radical of formula —(CH$_2$)$_4$—, —(CH$_2$)$_5$—, -Z$_4$-CH=CH—, -Z$_4$-CH$_2$—CH$_2$—CH$_2$— or -Z$_4$-CH$_2$—CH$_2$—, with Z$_4$ being O, S, SO$_2$ or NR$^{11}$ wherein R$^{11}$ is hydrogen, C$_{1-6}$alkyl, benzyl or C$_{1-6}$alkyloxycarbonyl; and wherein each bivalent radical is optionally substituted with C$_{1-6}$alkyl;

or R$^3$ and R$^4$ may be taken together to form a bivalent radical of formula —CH=CH—CH=CH— or —CH$_2$—CH$_2$—CH$_2$—CH$_2$—;

R$^5$ represents hydrogen; piperidinyl; oxo-thienyl; tetrahydrothienyl, arylC$_{1-6}$alkyl; C$_{1-6}$alkyloxycarbonylC$_{1-6}$alkyl or C$_{1-6}$alkyl optionally substituted with a radical C(=O)NR$_x$R$_y$, in which R$_x$ and R$_y$, each independently are hydrogen, cycloC$_{3-12}$alkyl, C$_{2-6}$alkynyl or C$_{1-6}$alkyl optionally substituted with cyano, C$_{1-6}$alkyloxy or C$_{1-6}$alkyloxycarbonyl;

Y represents O or S;

or Y and R$^5$ may be taken together to form =Y—R$^5$— which represents a radical of formula —CH=N—N= (c-1); or —N=N—N= (c-2);

aryl represents phenyl or naphthyl optionally substituted with one or more substituents selected from halo, C$_{1-6}$alkyloxy, phenyloxy, mono- or di(C$_{1-6}$alkyl)amino and cyano;

and when the R$^1$—C(=X) moiety is linked to another position than the 7 or 8 position, then said 7 and 8 position may be substituted with R$^{15}$ and R$^{16}$ wherein either one or both of R$^{15}$ and R$^{16}$ represents C$_{1-6}$alkyl or R$^{15}$ and R$^{16}$ taken together may form a bivalent radical of formula —CH=CH—CH=CH—.

A further most interesting group of compounds comprises those compounds of formula (I-A)* and (I-B)* wherein X represents O;

R$^1$ represents C$_{1-6}$alkyl; cycloC$_{3-12}$alkyl or (cycloC$_{3-12}$alkyl)C$_{1-6}$alkyl, wherein one or more hydrogen atoms in a C$_{1-6}$alkyl-moiety or in a cycloC$_{3-12}$alkyl-moiety optionally may be replaced by C$_{1-6}$alkyloxy, aryl, halo or thienyl;

R$^2$ represents hydrogen; halo; C$_{1-6}$alkyl or amino;

R$^3$ and R$^4$ each independently represent hydrogen or C$_{1-6}$alkyl; or

R$^2$ and R$^2$ may be taken together to form —R$^2$—R$^3$—, which represents a bivalent radical of formula -Z$_4$-CH$_2$—CH$_2$—CH$_2$— or -Z$_4$-CH$_2$—CH$_2$— with Z$_4$ being O or NR$^{11}$ wherein R$^{11}$ is C$_{1-6}$alkyl; and wherein each bivalent radical is optionally substituted with C$_{1-6}$alkyl;

or R$^3$ and R$^4$ may be taken together to form a bivalent radical of formula —CH$_2$—CH$_2$—CH$_2$—CH$_2$—;

R$^5$ represents hydrogen;

Y represents O; and aryl represents phenyl optionally substituted with halo.

A further interesting group of compounds comprises those compounds of formula (I-A)* and (I-B)* wherein the R$^1$—C(=X) moiety is linked to the quinoline or quinolinone moiety in position 6.

Especially interesting are the following radioactive compounds:

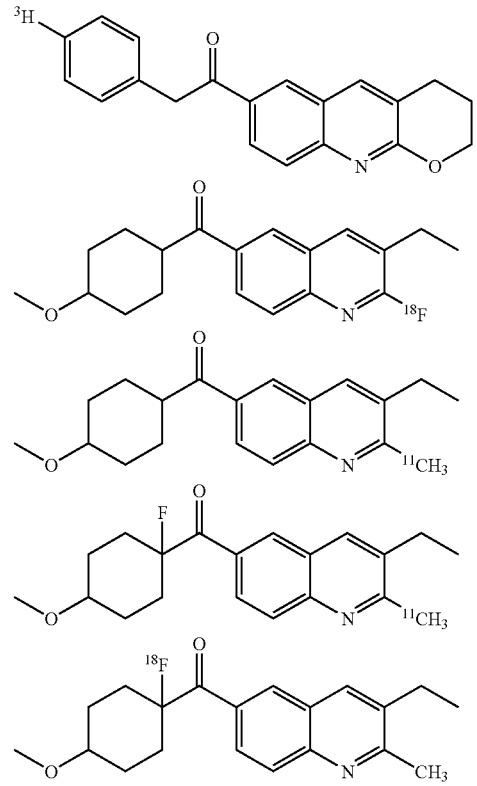

All compounds according to the invention show a moderate to strong mGluR1 activity. Such activity is among others attributed to the specific binding of said compound to the mGlu1 receptor, which makes the compounds useful in a diagnostic method, e.g. for labeling and detecting mGlu1 receptor sites. The invention therefore also relates to a radiolabelled compound according to the invention for use in a diagnostic method.

First Preferred Embodiment (Gamma Emitting Radionuclide)

According to a first preferred embodiment, the radiolabelled compound comprises at least one [$^3$H]-atom or one [$^{125}$I]-atom. A [$^3$H]-atom is conveniently introduced by partially or completely substituting one or more non-radioactive [$^3$H]-hydrogen atoms in the molecule by their radioactive isotopes. The choice of whether a [$^3$H] or [$^{125}$I] radioligand will be used may depend in part on the availability of liquid scintillation counters (LSC), which are fairly expensive. [$^{125}$I] ligands can be quantified using either a γ-counter or an LSC, whereas [$^3$H] ligands necessitate the use of an LSC.

The radiolabelled compound comprising at least one [$^3$H]-atom or one [$^{125}$I]-atom is advantageously used in radioligand-binding techniques, in particular in in vitro membrane receptor assays for marking or identifying a mGlu1 receptor in biological material.

The radiolabelled compounds comprising at least one [$^3$H]-atom or one [$^{125}$I]-atom is also advantageously used in in vivo mGlu1 receptor autoradiography of the brain since the compounds according to the invention have the advantageous and unexpected ability to readily cross the blood-brain barrier.

The invention therefore also relates to a radiolabelled compound according to the invention used in a diagnostic method which consists of marking or identifying a mGlu1 receptor in biological material, as well as the use of the compounds according to the invention for the manufacture of a diagnostic tool for marking or identifying an mGlu1 receptor in biological material, whether in vivo or in vitro.

In the framework of this application, by the term "biological material" is meant to include any material which has a biological origin. In particular, this relates to tissue samples, plasma fluids, body fluids, body parts and organs originating from warm-blooded animals and warm-blooded animals per se, in particular humans.

Basic experiments that are performed using the membrane assay system for marking or identifying a mGlu1 receptor in biological material are: saturation experiments, inhibition experiments, association kinetic experiments and dissociation kinetic experiments. These methods are applicable to most neurotransmitter and hormone receptor systems, including the mGluR1-system (Methods for Neurotransmitter Receptor Analysis, ed. by Henry I. Yamamura et al., Raven Press Ltd., New York, 1990). To this end, the radiolabelled compound is administered to the biological material to mark the mGlu1 receptors and the emissions from the radiolabelled compound are detected to identify the amount or location of the mGlu1 receptors, for instance for ex vivo receptor autoradiography.

The radiolabelled compounds according to the invention comprising at least one [$^3$H]-atom or one [$^{125}$I]-atom are also useful as agents for screening whether a test compound has the ability to occupy or bind to a mGlu1 receptor site. The degree to which a test compound will displace a compound according to the invention from the mGlu1 receptor site will show the test compound ability to occupy or bind to a mGlu1 receptor and therefore act as either an agonist, an antagonist or a mixed agonist/antagonist of a mGlu1 receptor.

The radiolabelled compounds according to the invention comprising at least one [$^3$H]-atom or one [$^{125}$I]-atom are advantageously prepared by substituting a halogen atom with a tritium atom, as is documented in the Experimental Section below.

Second Preferred Embodiment (Positron Emitting Radionuclide)

In a second preferred embodiment, the radiolabelled compound comprises at least one radioactive carbon or halogen atom. In principle, any compound according to Formula (I) containing a carbon or halogen atom is prone for radiolabelling by replacing the carbon or halogen atom by a suitable radioactive isotope or by making the compounds according to Formula (I) using radioactively-labelled reagentia. Suitable halogen radioisotopes to this purpose are radioactive carbon, e.g. [$^{11}$C]; radioactive iodides, e.g. [$^{122}$I], [$^{123}$I], [$^{131}$I]; radioactive bromides, e.g. [$^{75}$Br], [$^{76}$Br], [$^{77}$Br] and [$^{82}$Br]; and radioactive fluorides, e.g. [$^{18}$F]. Preferred radiolabelled compounds are those compounds of Formula (I-A)* and (I-B)*, wherein $R^1$ comprises a radioactive carbon or halo atom, especially [$^{11}$C], [$^{18}$F], [$^{123}$I], [$^{75}$Br], [$^{76}$Br] or [$^{77}$Br].

Preparation of the Radioactive Compounds

The introduction of a radioactive halogen atom can be performed by a suitable reaction such as depicted below

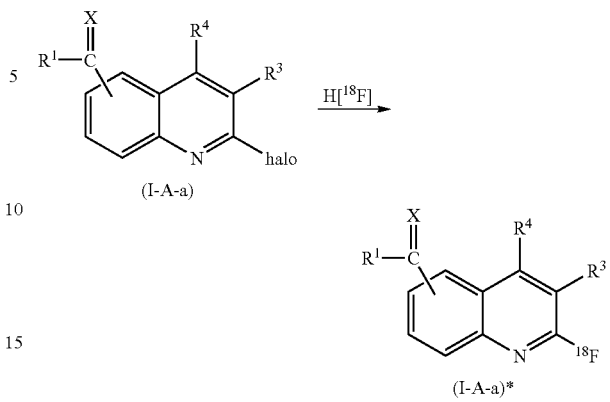

in which all substituents in Formula (I-A-a) and (I-A-a)* are defined as in Formula (I-A)* and halo is a halogen atom. A suitable compound (I-A-a) is reacted with H[$^{18}$F] such that the halogen atom present on the quinoline ring is displaced by a nucleophilic displacement reaction with the radioactive [$^{18}$F] atom.

For obtaining radiolabelled compounds according to Formula (I-B)*, radiolabelling can be performed on an equivalent way, for instance by way of a reaction scheme as depicted below. Obviously, also compounds according to Formula (I-A)* can be obtained in an equivalent way, i.e. by way of labelling an $R^1$ substituent.

Other methods for tritium-labelling are disclosed e.g. by Peng et al. *Fusion Technology*, American Nuclear Society, 21(2):307-311, 1992 and by Brundish et al. *Journal of Labelled Compounds and Radiopharmaceuticals* 25(12): 1361-1369 (1988).

The introduction of a radioactive [$^{11}$C] can be performed using the reaction scheme below in which a suitable compound (I-A-a) is first stanyllated after which the radioactive [$^{11}$C] is introduced using e.g. a palladium catalyzed "Stille-type" coupling reaction using [$^{11}$C]methyliodide (Scott, W. J.; Crisp, G. T.; Stille, J. K. *J. Am. Chem. Soc.*, 1984, 106, 4630).

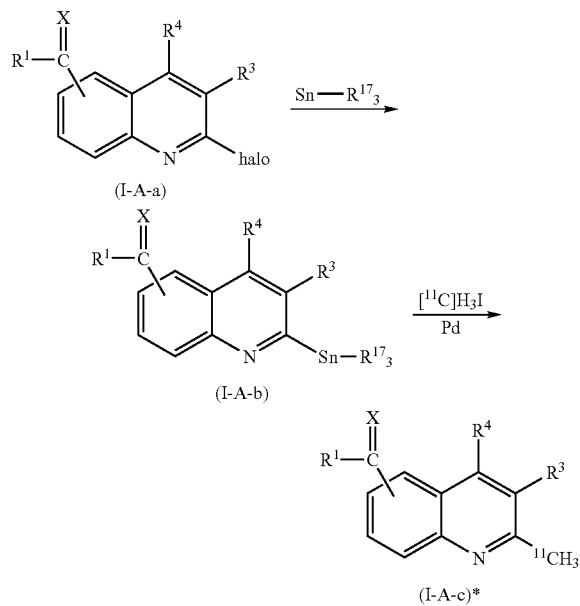

In Formula (I-A-a), (I-A-b) and (I-A-c)*, all substituents have the same meaning as defined in Formula (I-A)*, halo is a halogen atom and $R^{17}$ is methyl or butyl.

Because of their unexpected property to penetrate readily the blood-brain barrier, the radiolabelled compounds comprising a radioactive halogen atom are advantageously administered in vivo, in an appropriate composition to an animal, especially a warm-blooded animal, and the location of said radiolabelled compounds is detected using imaging techniques, such as, for instance, Single Photon Emission Computered Tomography (SPECT) or Positron Emission Tomography (PET) and the like. In this manner the distribution of mGlu1 receptor sites throughout the body can be detected and organs containing mGlu1 receptor sites such as, for example, the brain, can be visualized by the imaging techniques mentioned hereinabove. This process of imaging an organ by administering a radiolabelled compound of Formula (I-A)* or (I-A)*, which bind to the mGlu1 receptor sites and detecting the emissions from the radioactive compound also constitutes an aspect of the present invention.

The application of the compounds of Formula (I-A)* and (I-B)* in the above described techniques constitutes a further aspect of the present invention. The invention in particular relates to the use of the compounds according to the invention for the manufacture of a diagnostic tool for use in PET. For use in PET, most preferred are radiolabelled compounds according to the invention, in which a $^{18}F$ is incorporated (U.S. Pat. No. 4,931,270 by Horn et al., published Jun. 5, 1990).

Preparation of the Non-radioactive Compounds

The non-radioactive compounds according to the invention may be produced in a number of ways.

In order to simplify the structural representation of some of the present compounds and intermediates in the following preparation procedures, the quinoline or the quinolinone moiety will hereinafter be represented by the symbol Q.

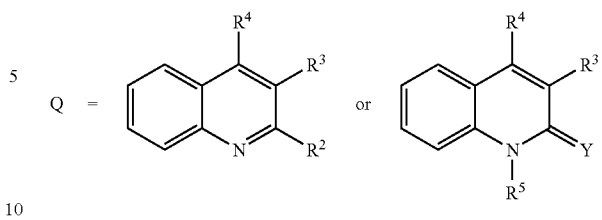

The compounds of formula (I-A) or (I-B), wherein X represents O, said compounds being represented by formula ($I_{A/B}$-a), can be prepared by oxidizing an intermediate of formula (II) in the presence of a suitable oxidizing agent, such as potassium permanganate, and a suitable phase-transfer catalyst, such as tris(dioxa-3,6-heptyl)amine, in a suitable reaction-inert solvent, such as for example dichloromethane.

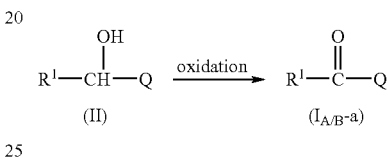

Compounds of formula ($I_{A/B}$-a) may also be prepared by reacting an intermediate of formula (III) with an intermediate of formula (IV), wherein $W_1$ represents a halo atom, e.g. bromo, in the presence of butyl lithium and a suitable reaction-inert solvent, such as for example tetrahydrofuran.

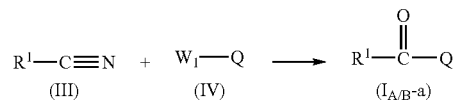

Alternatively, compounds of formula ($I_{A/B}$-a) may also be prepared by reacting an intermediate of formula (V) with an intermediate of formula (IV) in the presence of butyl lithium and a suitable reaction-inert solvent, such as for example tetrahydrofuran.

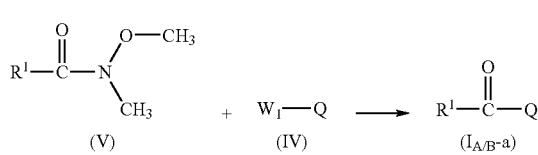

Compounds of formula ($I_{A/B}$-a), wherein the $R^1$ substituent is linked to the carbonyl moiety via an oxygen atom, said $R^1$ substituent being represented by O—$R^{1a}$ and said compounds by formula ($I_{A/B}$-a-1), can be prepared by reacting an intermediate of formula (VI) with an intermediate of formula (VII) in the presence of a suitable acid, such as sulfuric acid.

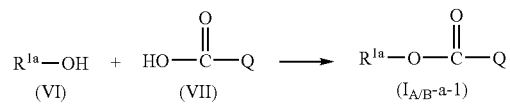

Compounds of formula (I-A), wherein $R^2$ represents methylcarbonyl, said compounds being represented by formula (I-A-1), can be prepared by reacting an intermediate of formula (VIII) in the presence of a suitable acid, such as hydrochloric acid, and a suitable reaction-inert solvent, such as for example tetrahydrofuran.

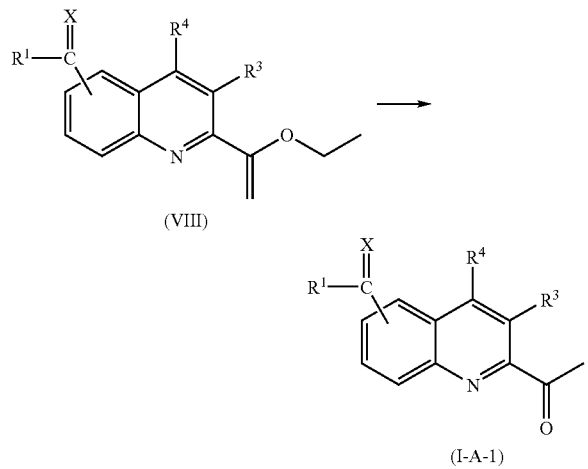

The compounds of formula (I) may also be converted into each other following art-known transformations.

Compounds of formula (I-A) wherein $R^2$ is a halo atom, such as chloro, can be converted into a compound of formula (I-A), wherein $R^2$ is another halo atom, such as fluoro or iodo, by reaction with a suitable halogenating agent, such as for example potassium fluoride or sodium iodide, in the presence of a suitable reaction-inert solvent, e.g. dimethyl sulfoxide or acetonitrile and optionally in the presence of acetyl chloride.

Compounds of formula (I-A), wherein $R^2$ is a suitable leaving group, such as a halo atom, e.g. chloro, iodo, said leaving group being represented by $W^2$ and said compounds by (I-A-2), can be converted into a compound of formula (I-A) wherein $R^2$ is cyano, said compound being represented by formula (I-A-3), by reaction with a suitable cyano-introducing agent, such as for example trimethylsilanecarbonitrile, in the presence of a suitable base such as N,N-diethylethanamine and a suitable catalyst, such as for example tetrakis(triphenylphosphine)palladium.

Compounds of formula (I-A-2) can also be converted into a compound of formula (I-A-4) by reaction with $C_{2-6}$alkynyl-tri($C_{1-6}$alkyl)silane in the presence of CuI, an appropriate base, such as for example N,N-diethylethanamine, and an appropriate catalyst, such as for example tetrakis(triphenylphosphine)palladium. Compounds of formula (I-A-4) can on their turn be converted into a compound of formula (I-A-5) by reaction with potassium fluoride in the presence of a suitable acid such as acetic acid, or by reaction with a suitable base, such as potassium hydroxide, in the presence of a suitable reaction-inert solvent, such as an alcohol, e.g. methanol and the like.

Compounds of formula (I-A-2) can also be converted into a compound of formula (I-A-6) by reaction with an intermediate of formula (IX) in the presence of CuI, a suitable base, such as for example N,N-diethylethanamine, and a suitable catalyst such as tetrakis(triphenylphosphine)palladium.

Compounds of formula (I-A-2) can also be converted into a compound wherein $R^2$ is $C_{1-6}$alkyl, said compound being represented by formula (I-A-8) in the presence of a suitable alkylating agent, such as for example $Sn(C_{1-6}alkyl)_4$, or into a compound wherein $R^2$ is $C_{2-6}$alkenyl, said compound being represented by formula (I-A-9) in the presence of a suitable alkenylating agent, such as for example $Sn(C_{2-6}alkenyl)(C_{1-6}alkyl)_3$, both reactions in the presence of a suitable catalyst, such as for example tetrakis(triphenylphosphine)palladium and a reaction-inert solvent, such as for example toluene or dioxane.

Compounds of formula (I-A-2) can also be converted into a compound of formula (I-A-7) wherein Z represents O or S, by reaction with an intermediate of formula (X) optionally in the presence of a suitable base such as dipotassium carbonate and a reaction-inert solvent, such as N,N-dimethyl formamide.

Compounds of formula (I-A-2) can also be converted into a compound of formula (I-A), wherein $R^2$ is $C_{1-6}$alkyloxycarbonyl, said compound being represented by formula (I-A-10) and a compound of formula (I-A), wherein $R^2$ is hydrogen, said compound being represented by formula (I-A-11), by reaction with a suitable alcohol of formula $C_{1-6}$alkylOH and CO in the presence of a suitable catalyst, such as for example palladium(II)acetate, triphenylphosphine, a suitable base such as dipotassium carbonate and a reaction-inert solvent, such as N,N-dimethylformamide.

Compounds of formula (I-A-11) can also be prepared by reacting a compound of formula (I-A-2) with Zn in the presence of a suitable acid such as acetic acid.

Compounds of formula (I-A-2) can also be converted into a compound of formula (I-A), wherein $R^2$ is aminocarbonyl substituted with $C_{1-6}$alkyloxycarbonyl$C_{1-6}$alkyl, said compound being represented by formula (I-A-12), by reaction with an intermediate of formula $H_2N-C_{1-6}alkyl-C(=O)-O-C_{1-6}alkyl$ in the presence of CO, a suitable catalyst such as tetrakis(triphenylphosphine)palladium, a suitable base, such as for example N,N-diethylethanamine, and a suitable reaction-inert solvent, such as for example toluene.

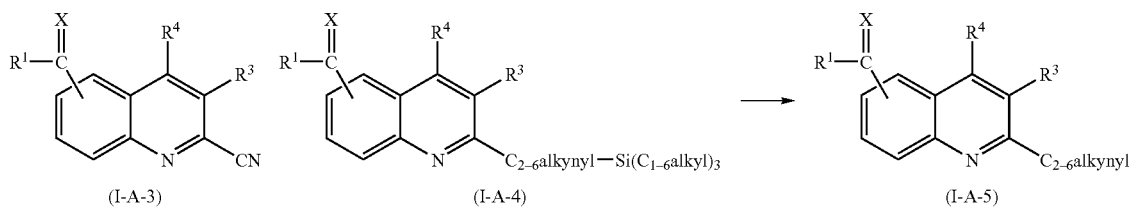

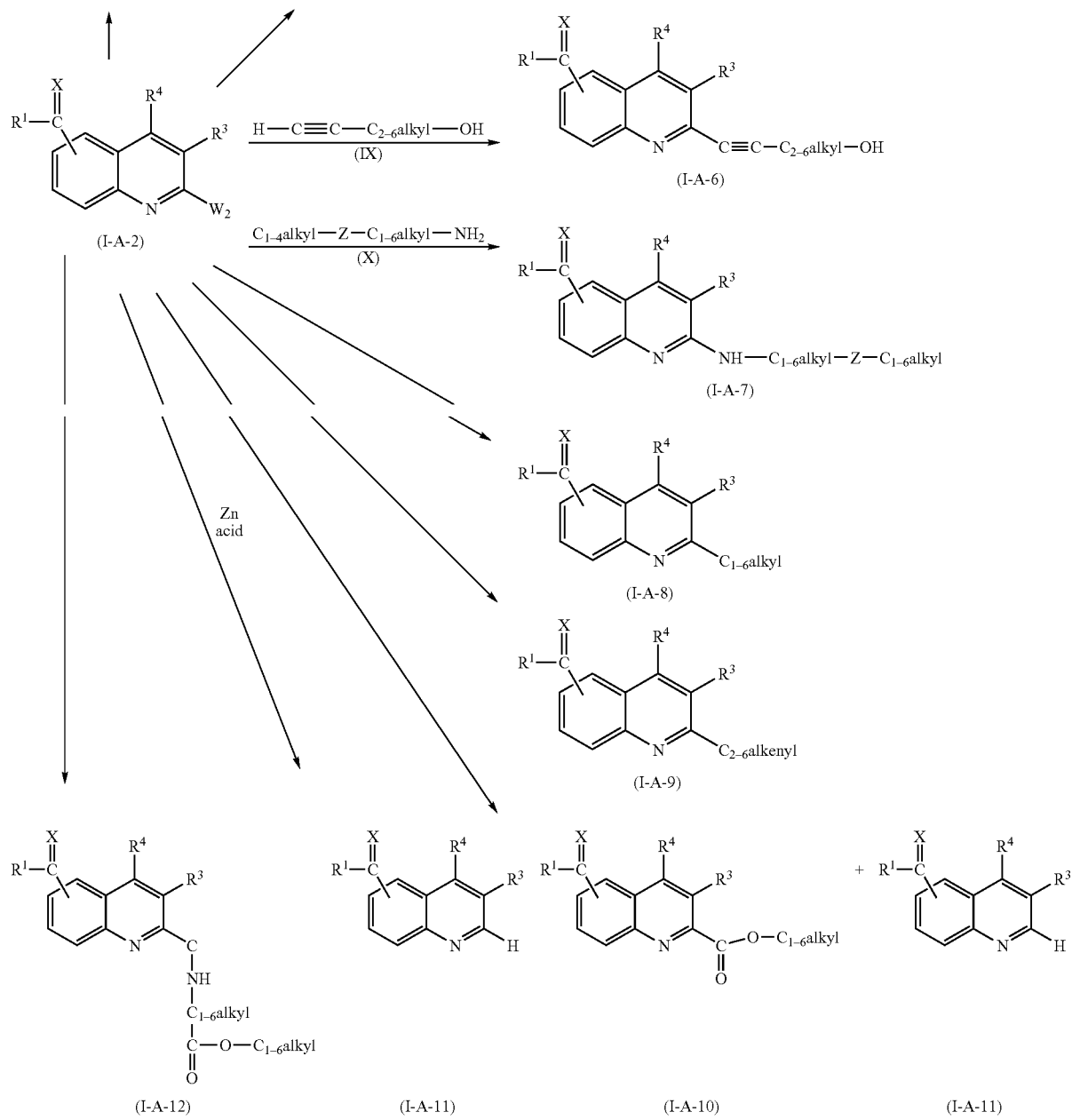

Compounds of formula (I-A-2) can also be converted into a compound of formula (I-A) wherein $R^2$ is aryl or a heterocycle selected from the group described in the definition of $R^2$ hereinabove, said $R^2$ being represented by $R^{2a}$ and said compound by formula (I-A-13) by reaction with an intermediate of formula (XI), (XII) or (XIII) in the presence of a suitable catalyst such as for example tetrakis(triphenylphosphine)palladium and a suitable reaction-inert solvent, such as for example dioxane.

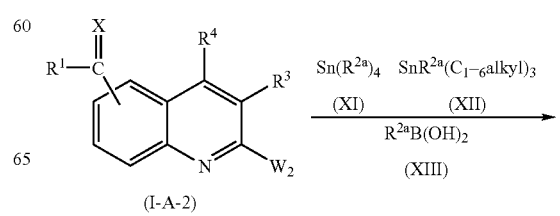

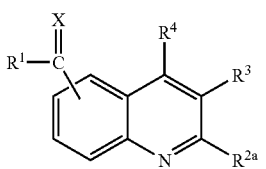

(I-A-13)

Compounds of formula (I-A-2) can also be converted into a compound of formula (I-B), wherein Y and $R^5$ are taken together to form a radical of formula (b-1) or (b-2), said compound being represented by formula (I-B-1) or (I-B-2), by reaction with hydrazincarboxaldehyde or sodium azide in a suitable reaction-inert solvent, such as an alcohol, e.g. butanol, or N,N-dimethylformamide.

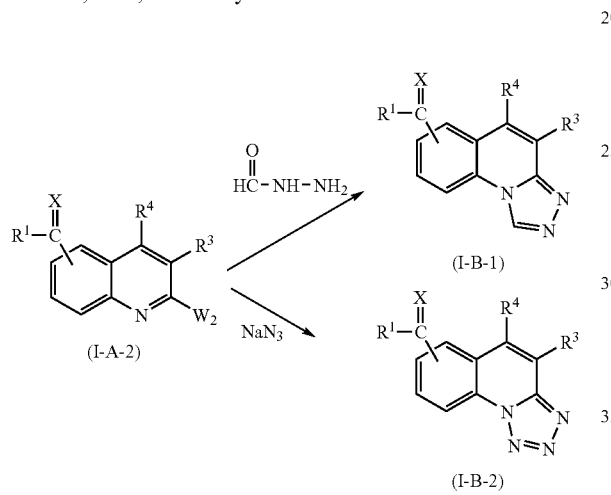

Compounds of formula (I-A-11) can be converted into the corresponding N-oxide, represented by formula (I-A-14), by reaction with a suitable peroxide, such as 3-chloro-benzenecarboperoxoic acid, in a suitable reaction-inert solvent, such as for example methylene chloride. Said compound of formula (I-A-14) can further be converted into a compound of formula (I-B), wherein $R^5$ is hydrogen, said compound being represented by formula (I-B-3), by reaction with 4-methylbenzene sulfonyl chloride in the presence of a suitable base, such as for example dipotassium carbonate and a suitable reaction-inert solvent, such as for example methylene chloride.

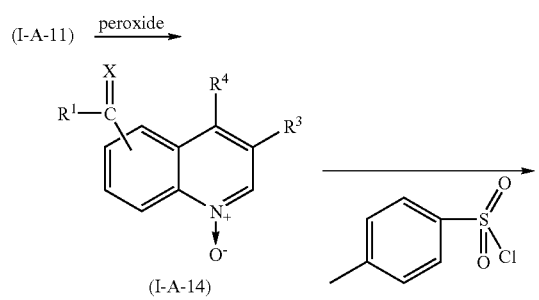

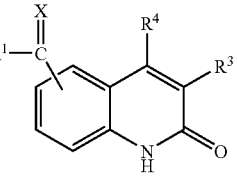

(I-B-3)

Compounds of formula (I-B-3) can also be prepared from a compound of formula (I-A), wherein $R^2$ is $C_{1-6}$alkyloxy, said compound being represented by formula (I-A-15), by reaction with a suitable acid, such as hydrochloric acid, in the presence of a suitable reaction-inert solvent, such as for example tetrahydrofuran.

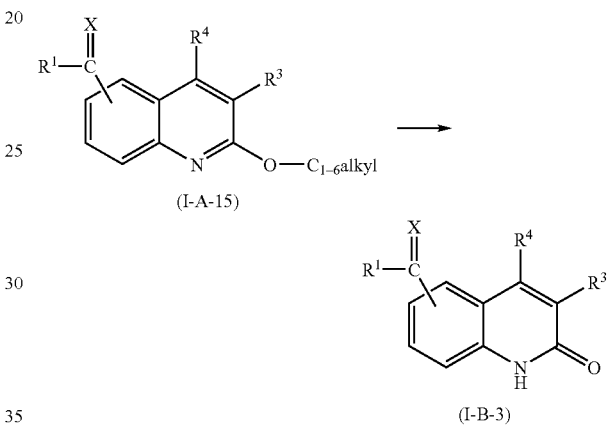

Compounds of formula (I-B-3) can be converted into a compound of formula (I-B), wherein $R^5$ represents $C_{1-6}$alkyl, said compound being represented by formula (I-B-4), by reaction with an appropriate alkylating agent, such as for example an intermediate of formula (XIV), wherein $W_3$ represents a suitable leaving group such as a halo atom e.g. iodo, in the presence of potassium tert. butoxide and in the presence of a suitable reaction-inert solvent, such as for example tetrahydrofuran.

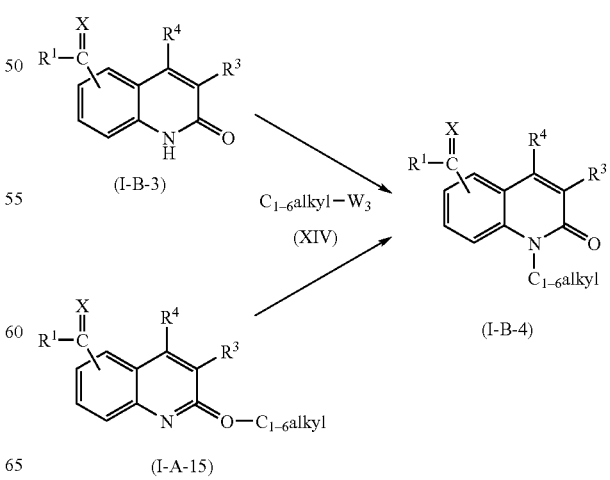

Compounds of formula (I-B-3) can also be converted into a compound of formula (I-B), wherein $R^5$ is $C_1$-alkyloxycarbonyl$C_{1-6}$alkyl or aryl$C_{1-6}$alkyl, said $R^5$ being represented by $R^{5a}$ and said compound being represented by formula (I-B-5), by reaction with an intermediate of formula (XV), wherein $W_4$ represents a suitable leaving group, such as a halo atom, e.g. bromo, chloro and the like, in the presence of a suitable base, such as for example sodium hydride and a suitable reaction-inert solvent, such as for example N,N-dimethylformamide.

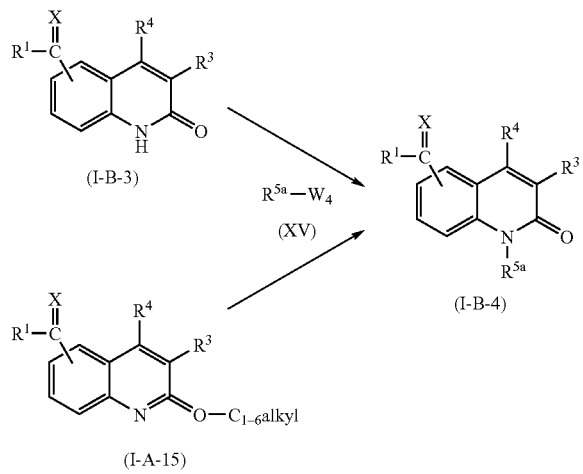

Compounds of formula (I-A-2) can also be converted into a compound of formula (I-B), wherein $R^5$ is hydrogen and Y is S, said compound being represented by formula (I-B-6), by reaction with $H_2N-C(=S)-NH_2$ in the presence of a suitable base, such as potassium hydroxide, and a suitable reaction-inert solvent, such as an alcohol, for example ethanol, or water. Compounds of formula (I-B-6) can further be converted into a compound of formula (I-A), wherein $R^2$ is $C_{1-6}$alkylthio, said compound being represented by formula (I-A-16), by reaction with a suitable $C_{1-6}$alkylhalide, such as for example $C_{1-6}$alkyliodide, in the presence of a suitable base, such as dipotassium carbonate, and a suitable solvent, such as for example acetone.

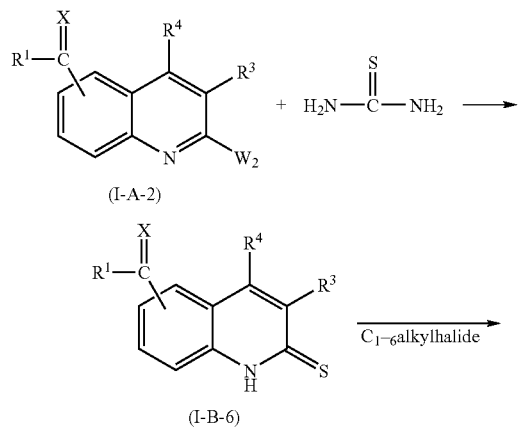

Compounds of formula ($I_{A/B}$-a) can be converted into a compounds of formula (I-A) or (I-B), wherein X is N—$R^7$, said compound being represented by formula ($I_{A/B}$-b), by reaction with an intermediate of formula (XVI), optionally in the presence of a suitable base, such as for example N,N-diethylethanamine, and in the presence of a suitable reaction-inert solvent, such as an alcohol, e.g. ethanol.

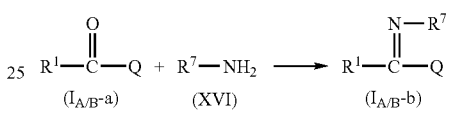

As already indicated in the preparation procedure of compounds of formula (I-A-13) described above, the compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Some of the intermediates and starting materials used in the above reaction procedures are commercially available, or may be synthesized according to procedures already described in the literature.

Intermediates of formula (II) may be prepared by reacting an intermediate of formula (XVII) with an intermediate of formula (XVIII), wherein $W_5$ represents a suitable leaving group such as a halo atom, e.g. chloro, bromo and the like, in the presence of magnesium, diethylether and a suitable reaction-inert solvent, such as diethylether.

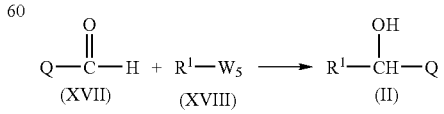

Intermediates of formula (XVII) may be prepared by oxidizing an intermediate of formula (XIX) in the presence of a suitable oxidizing agent, such as $MnO_2$, and a suitable reaction-inert solvent, such as methylene chloride.

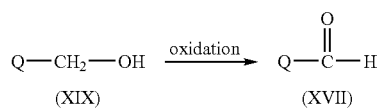

Intermediates of formula (XIX) can be prepared by reducing an intermediate of formula (XX) in the presence of a suitable reducing agent such as lithium aluminium hydride, and a suitable reaction-inert solvent, such as tetrahydrofuran.

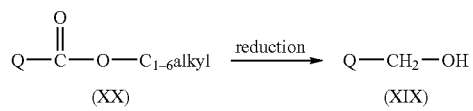

Intermediates of formula (XX), wherein Q represents a quinoline moiety optionally substituted in position 3 with $C_{1-6}$alkyl and wherein the carbonyl moiety is placed in position 6, said intermediates being represented by formula (XX-a), can be prepared by reacting an intermediate of formula (XXI) with an intermediate of formula (XXII) in the presence of sodium 3-nitro-benzene sulfonate, a suitable acid, such as sulfuric acid, and a suitable alcohol, e.g. methanol, ethanol, propanol, butanol and the like.

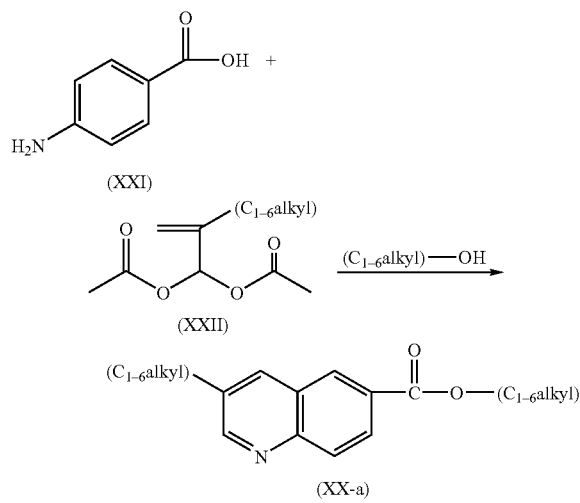

Alternatively, intermediates of formula (II) can also be prepared by reacting an intermediate of formula (XXIII) with an intermediate of formula (XXIV), wherein $W_6$ is a suitable leaving group, such as a halo atom, e.g. bromo, chloro and the like, in the presence of a suitable agent, such as butyl lithium and a suitable reaction-inert solvent, such as tetrahydrofuran.

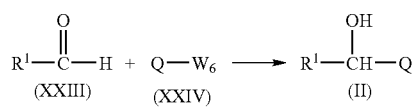

Intermediates of formula (XXIII) can be prepared by oxidizing an intermediate of formula (XXV) using the Moffatt Pfitzner or Swern oxidation (dimethylsulfoxide adducts with dehydrating agents e.g. DCC, $Ac_2O$, $SO_3$, $P_4O_{10}$, $COCl_2$ or Cl—CO—COCl) in an inert solvent such as methylene chloride.

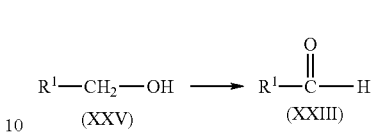

Intermediates of formula (XXV) can be prepared by reducing an intermediate of formula (XXVI) in the presence of a suitable reducing agent, such as for example lithium aluminium hydride and a suitable reaction-inert solvent, such as benzene.

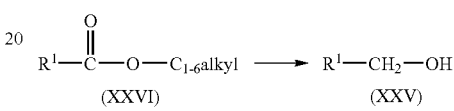

Intermediates of formula (XXVI) can be prepared from an intermediate of formula (XXVII) by esterification in the presence of a suitable alcohol, such as methanol, ethanol, propanol, butanol and he like, and a suitable acid, such as sulfuric acid.

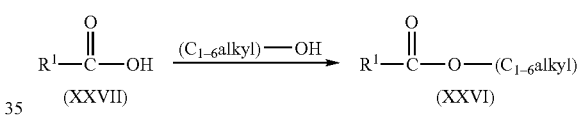

Intermediates of formula (XXVII), wherein $R^1$ represents a radical of formula (a-1) with Z, being O, $Z_2$ being $CH_2$ and n being 1, said intermediates being represented by formula (XXVII-a), can be prepared by reducing an intermediate of formula (XXVIII) in the presence of a suitable reducing agent such as hydrogen, and a suitable catalyst, such as palladium on charcoal, and a suitable acid such as acetic acid. When $R^1$ of intermediate (XXVII) represents an optionally substituted phenyl moiety, it can also be converted into an optionally substituted cyclohexyl moiety by reduction in the presence of a suitable reducing agent such as rhodium on $Al_2O_3$, and a suitable reaction-inert solvent, such as tetrahydrofuran.

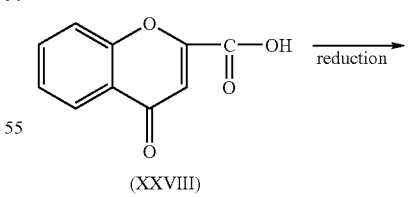

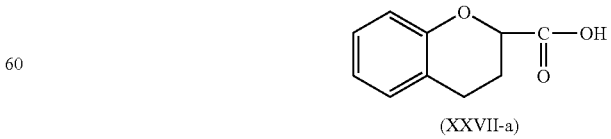

Intermediates of formula (IV), wherein Q represents a quinoline moiety substituted in position 2 with halo, e.g. chloro, said intermediates being represented by formula (IV-a), can be prepared by reacting an intermediate of formula (IV), wherein Q represents a quinolinone moiety with $R^5$ being hydrogen, said intermediate being represented by formula (IV-b), in the presence of $POCl_3$.

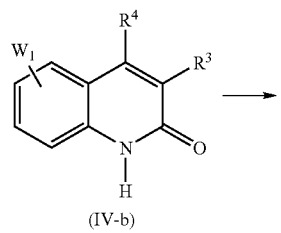

(IV-b)

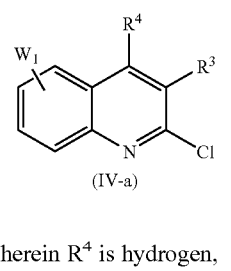

(IV-a)

Intermediates of formula (IV-a), wherein $R^4$ is hydrogen, said intermediates being represented by formula (IV-a-1), can also be prepared by reacting an intermediate of formula (XXIX) with $POCl_3$ in the presence of N,N-dimethylformamide (Vilsmeier-Haack formylation followed by cyclization).

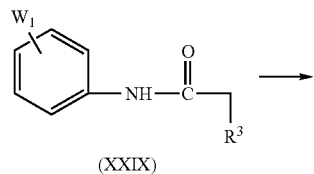

(XXIX)

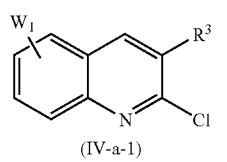

(IV-a-1)

Intermediates of formula (XXIX) may be prepared by reacting an intermediate of formula (XXX) with an intermediate of formula (XXXI), wherein $W_7$ represents a suitable leaving group, such as a halo atom, e.g. chloro, in the presence of a suitable base, such as for example N,N-diethylethanamine, and a suitable reaction-inert solvent, such as methylene chloride.

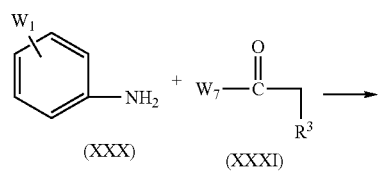

(XXX)   (XXXI)

-continued

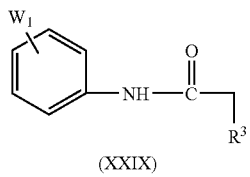

(XXIX)

Intermediates of formula (IV-a) can be converted into an intermediate of formula (IV-c) by reaction with an intermediate of formula (XXXII) in the presence of a suitable reaction-inert solvent, such as an alcohol, e.g. methanol and the like.

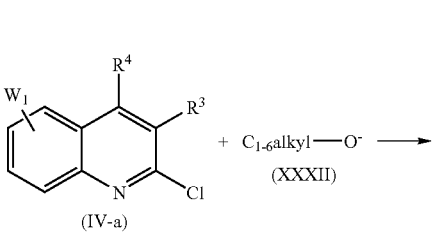

(IV-a)

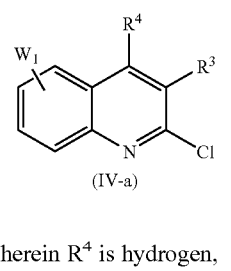

(IV-c)

Intermediates of formula (IV-a) can also be converted into an intermediate of formula (IV-d-1) by reaction with a suitable amine of formula (XXXIII-a), wherein $Z_3$ and $Z_4$ each independently represent hydrogen, $C_{1-6}$alkyl, $C_{1-6}$alkyloxy$C_{1-6}$alkyl, $C_{1-6}$alkylthio$C_{1-6}$alkyl or into an intermediate of formula (IV-d-2) by reaction with a suitable amine of formula (XXXIII-b), wherein $Z_3$ and $Z_4$ are taken together to form a heterocycle as defined hereinabove in the definition of $R^2$ provided that the heterocycle comprises at least one nitrogen atom, in the presence of a suitable base, such as for example dipotassium carbonate, and a reaction-inert solvent, such as N,N-dimethylformamide.

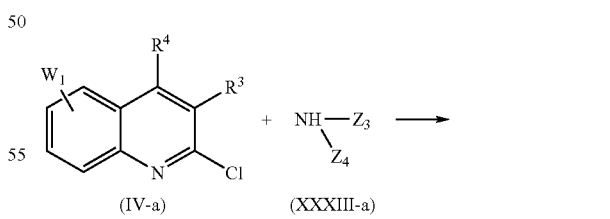

(IV-a)   (XXXIII-a)

(IV-d-1)

-continued

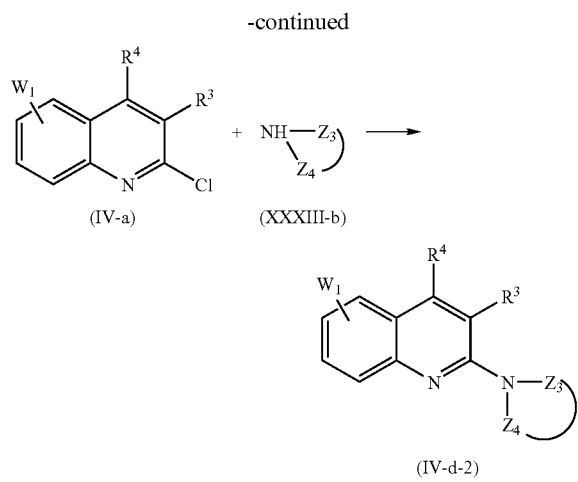

Intermediates of formula (IV-a), wherein $R^3$ represents $CH_2$—$CH_2$—$CH_2$—Cl, said intermediates being represented by formula (IV-a-2), can also be converted into an intermediate of formula (IV), wherein $R^2$ and $R^3$ are taken together to form a bivalent radical of formula —O—$CH_2$—$CH_2$—$CH_2$—, said intermediate being represented by formula (IV-e-1), by reaction with a suitable acid, such as hydrochloric acid and the like.

Intermediates of formula (IV-a-2) can also be converted into an intermediate of formula (IV), wherein $R^2$ and $R^3$ are taken together to form a bivalent radical of formula —S—$CH_2$—$CH_2$—$CH_2$—, said intermediate being represented by formula (IV-e-2), by reaction with $H_2N$—C(=S)—$NH_2$ in the presence of a suitable reaction-inert solvent, such as an alcohol, e.g. ethanol.

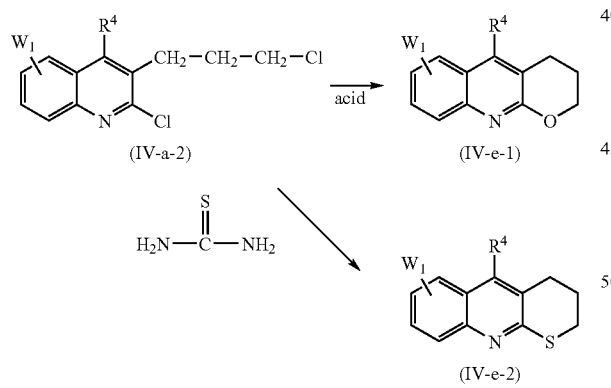

Intermediates of formula (V) may be prepared by reacting an intermediate of formula (XXVII) with an intermediate of formula $CH_3$—NH—O—$CH_3$ in the presence of 1,1'-carbonyldiimidazole and a suitable reaction-inert solvent, such as methylene chloride.

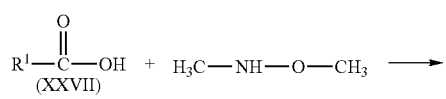

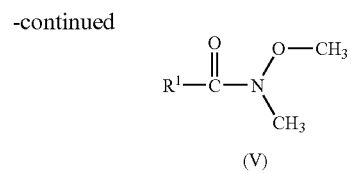

Intermediates of formula (VII), wherein Q represents a quinoline moiety, in particular a quinoline moiety wherein $R^2$ is ethyl, $R^3$ is methyl and $R^4$ is hydrogen, and the carboxyl moiety is placed in position 6, said intermediates being represented by formula (VII-a), can be prepared by reaction an intermediate of formula (XXXIV) in the presence of a suitable aldehyde, such as $CH_3$—$CH_2$—CH(=O), $(CH_2O)_n$, $ZnCl_2$, $FeCl_3$ and a suitable reaction-inert solvent, such as an alcohol, for example ethanol.

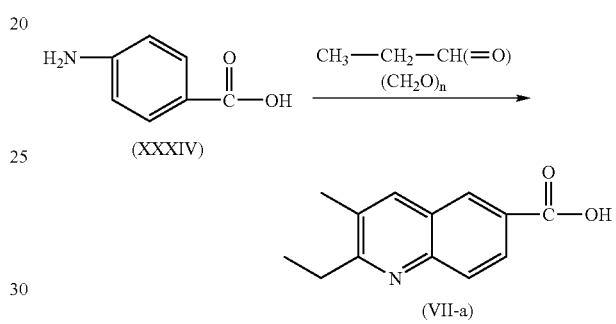

Intermediates of formula (VIII) can be prepared by reacting an intermediate of formula (XXXV) with an intermediate of formula (XXXVI) in the presence of a suitable catalyst, such as for example tetrakis(triphenylphosphine)palladium and a suitable reaction-inert solvent, such as for example dioxane.

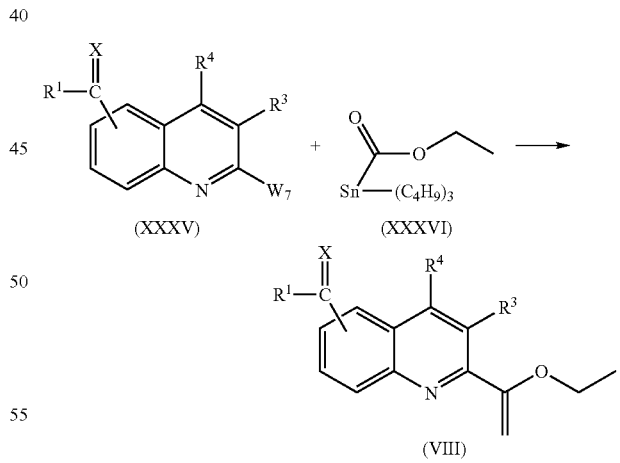

Still some other preparations can be devised, some of them are disclosed further in this application with the Examples.

Pure stereoisomeric forms of the compounds and the intermediates of this invention may be obtained by the application of art-known procedures. Diastereomers may be separated by physical separation methods such as selective crystallization and chromatographic techniques, e.g. liquid chromatography using chiral stationary phases. Enantiomers may be separated from each other by the selective crystallization of their diastereomeric salts with optically active acids. Alternatively, enantiomers may be separated by chromato-graphic techniques using chiral stationary phases. Said pure stereoisomeric forms may also be derived from the corresponding pure stereoisomeric forms of the appropriate starting materials, provided that the reaction occurs stereo selectively or stereospecifically. Preferably, if a specific stereoisomer is desired, said compound will be synthesized by stereoselective or stereospecific methods of preparation. These methods will advantageously employ chirally pure starting materials. Stereoisomeric forms of the compounds of formula (I) are obviously intended to be included within the scope of the invention.

A stereoisomer of a compound of formula (I-A) or (I-B) such as a cis form, may be converted into another stereoisomer such as the corresponding trans form by reacting the compound with a suitable acid, such as hydrochloric acid, in the presence of a suitable reaction-inert solvent, such as for example tetrahydrofuran.

The mGluR1 antagonistic activity of the present compounds can be demonstrated in the Signal transduction on cloned rat mGluR1 in CHO cells test and the Cold allodynia test in rats with a Bennett ligation, as described hereinafter.

Due to their mGluR antagonistic activity, more in particular their Group I mGluR antagonistic activity and even more in particular, their mGluR1 antagonistic activity, the compounds of formula (I-A) or (I-B), their N-oxides, pharmaceutically acceptable addition salts, quaternary amines and stereochemically isomeric forms are useful in the treatment or prevention of glutamate-induced diseases of the central nervous sytem. Diseases in which a role for glutamate has been demonstrated include drug addiction or abstinence (dependence, opioid tolerance, opioid withdrawal), hypoxic, anoxic and ischemic injuries (ischemic stroke, cardiac arrest), pain (neuropathic pain, inflammatory pain, hyperalgesia), hypoglycemia, diseases related to neuronal damage, brain trauma, head trauma, spinal cord injury, myelopathy, dementia, anxiety, schizophrenia, depression, impaired cognition, amnesia, bipolar disorders, conduct disorders, Alzheimer's disease, vascular dementia, mixed (Alzheimer's and vascular) dementia, Lewy Body disease, delirium or confusion, Parkinson's disease, Huntington's disease, Down syndrome, epilepsy, aging, Amyotrophic Lateral Sclerosis, multiple sclerosis, AIDS (Acquired Immune Deficiency Syndrome) and AIDS related complex (ARC).

The present invention also provides compositions for the administration to mamals, in particular humans, in particular for diagnostic reasons, more in particular for imaging an organ comprising a therapeutically effective amount of a radiolabelled compound of formula (I-A)* or (I-B)* and a pharmaceutically acceptable carrier or diluent.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, a therapeutically effective amount of a particular compound, in base or addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, topically, percutaneously or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, emulsions, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. As appropriate compositions for topical application there may be cited all compositions usually employed for topically administering drugs e.g. creams, gel, dressings, shampoos, tinctures, pastes, ointments, salves, powders and the like. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used in the specification and claims herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions, teaspoonfuls, tablespoonfuls and the like, and segregated multiples thereof.

The diagnostically effective dose or frequency of administration depends on the particular compound of formula (I-A)* or (I-B)* used and the particular condition of the mamal being treated, as is well known to those skilled in the art.

The following examples are intended to illustrate and not to limit the scope of the present invention.

Experimental Part

Hereinafter, "DMF" is defined as N,N-dimethylformamide, "DIPE" is defined as diisopropylether, "DMSO" is defined as dimethylsulfoxide, "BHT" is defined as 2,6-bis(1,1-dimethylethyl)-4-methylphenol, and "THF" is defined as tetrahydrofuran.

A. Preparation of the Intermediates

EXAMPLE A1

Preparation of

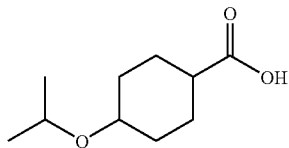
(interm. 1)

A mixture of 4-(1-methylethoxy)benzoic acid (0.083 mol) and Rh/Al$_2$O$_3$ 5% (10 g) in THF (220 ml) was hydrogenated at 50° C. (under 3 bar pressure of H$_2$) for 1 night. The mixture was filtered over celite, washed with THF and evaporated. Yield: 16 g of intermediate 1 (100%).

EXAMPLE A2

Preparation of 2-ethyl-3-methyl-6-quinolinecarboxylic acid (interm. 2)

A mixture of 4-aminobenzoic acid (0.299 mol) in ethanol (250 ml) was stirred at room temperature. ZnCl$_2$ (0.0367 mol) and (CH$_2$O)$_n$ (10 g) were added. FeCl$_3$.6H$_2$O (0.5 mol) was added portionwise and the temperature rised till 60-65° C. Propanal (30 ml) was added dropwise over a 2 hours period. The mixture was refluxed for 2 hours and kept at room temperature for 12 hours. The mixture was poured into water and filtered through celite. The filtrate was acidified till pH=7 with HCl 6N and the mixture was evaporated till dryness. The residue was used without further purification. Yield: 56.1 g of 2-ethyl-3-methyl-6-quinolinecarboxylic acid (interm. 2).

EXAMPLE A3

Preparation of

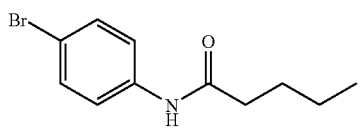
(interm. 3)

Pentanoyl chloride (0.2784 mol) was added at 5° C. to a mixture of 4-bromobenzenamine (0.232 mol) and N,N-diethylethanamine (0.2784 mol) in CH$_2$Cl$_2$ (400 ml). The mixture was stirred at room temperature overnight, poured out into water and extracted with CH$_2$Cl$_2$. The organic layer was separated, washed with a concentrated NH$_4$OH solution and water, dried (MgSO$_4$), filtered and the solvent was evaporated. The residue (60 g) was crystallized from diethylether. The precipitate was filtered off and dried. The residue (35 g, 63%) was taken up in CH$_2$Cl$_2$. The organic layer was separated, washed with a 10% K$_2$CO$_3$ solution, washed with water, dried (MgSO$_4$), filtered and the solvent was evaporated. Yield: 30 g of intermediate (3) (54%).

EXAMPLE A4

Preparation of

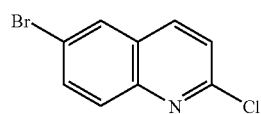
(interm. 4)

A mixture of 6-bromo-2(1H)-quinolinone (0.089 mol) in POCl$_3$ (55 ml) was stirred at 60° C. overnight, then at 100° C. for 3 hours and the solvent was evaporated. The residue was taken up in CH$_2$Cl$_2$, poured out into ice water, basified with NH$_4$OH conc., filtered over celite and extracted with CH$_2$Cl$_2$. The organic layer was separated, dried (MgSO$_4$), filtered and the solvent was evaporated. Yield: 14.5 g of intermediate (4) (67%).

EXAMPLE A5 a) Preparation of

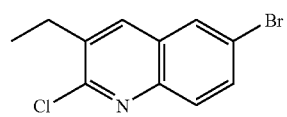
(interm. 5)

DMF (37 ml) was added dropwise at 10° C. under N$_2$ flow to POCl$_3$ (108 ml). After complete addition, the mixture was allowed to warm to room temperature. N-(4-bromophenyl)butanamide (0.33 mol) was added portionwise. The mixture was stirred at 85° C. overnight, then allowed to cool to room temperature and poured out on ice (exothermic reaction). The precipitate was filtered off, washed with a small amount of water and dried (vacuum). The residue was washed with EtOAc/diethyl ether and dried. Yield: 44.2 g of intermediate (5) (50%).

b) Preparation of

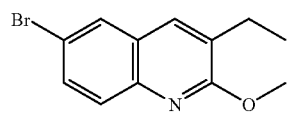
(interm. 6)

A mixture of intermediate (5) (0.162 mol) in methanol (600 ml), and a solution of methanol sodium salt in methanol at 35% (154 ml) was stirred and refluxed overnight. The mixture was poured out on ice. The precipitate was filtered off, washed with a small amount of water and taken up in CH$_2$Cl$_2$. K$_2$CO$_3$ 10% was added and the mixture was extracted with CH$_2$Cl$_2$. The organic layer was separated, washed with water,

EXAMPLE A6

Preparation of

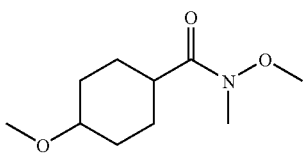
(interm. 7)

1,1'-Carbonylbis-1H-imidazole (0.074 mol) was added portionwise to a mixture of 4-methoxycyclohexanecarboxylic acid (0.063 mol) in $CH_2Cl_2$ (200 ml). The mixture was stirred at room temperature for 1 hour. Then N-methoxymethanamine (0.074 mol) was added. The mixture was stirred at room temperature overnight, poured out into $H_2O$ and extracted with $CH_2Cl_2$. The organic layer was separated, washed several times with $H_2O$, dried ($MgSO_4$), filtered and the solvent was evaporated. Yield: 12.6 g of interm. 7.

EXAMPLE A7 a) A mixture of 6-fluoro-4-oxo-4H-1-benzopyran-2-carboxylic acid (0.30 mol) in acetic acid (400 ml) was hydrogenated with Pd/C (3 g) as a catalyst. After uptake of $H_2$ (3 equiv), the catalyst was filtered off. The filtrate was evaporated. The residue was stirred in petroleum ether. The precipitate was filtered off and dried (vacuum; 70° C.). After recrystallization from $CHCl_3/CH_3OH$, the precipitate was filtered off and dried (vacuum; 80° C. and high vacuum; 85° C.). Yield: 8.8 g of 6-fluoro-3,4-dihydro-2H-1-benzopyran-2-carboxylic acid (interm. 8) (15.0%).

b) A mixture of intermediate (8) (0.255 mol) in ethanol (400 ml) and $H_2SO_4$ (5 ml) was stirred and refluxed for 8 hours. The solvent was evaporated till dryness. The residue was dissolved in $CH_2Cl_2$. The organic layer was separated, washed with $K_2CO_3$ 10%, dried ($MgSO_4$), filtered and the solvent was evaporated. Yield: 45 g of ethyl 6-fluoro-3,4-dihydro-2H-1-benzopyran-2-carboxylate (interm. 9) (79%).

c) Reaction under $N_2$. A mixture of sodium bis(2-methoxyethoxy)aluminumhydride, 70 wt % solution in methylbenzene 3.4M (0.44 mol) in benzene (150 ml) (reflux) was added dropwise during 1 hour to a refluxed mixture of interm. 9 (0.22 mol) and benzene (600 ml). After stirring for 2.5 hours at reflux temperature, the mixture was cooled to ±15° C. The mixture was decomposed by adding dropwise ethanol (30 ml) and water (10 ml). This mixture was poured out onto ice/water and this mixture was acidified with concentrated hydrochloric acid. This mixture was extracted with diethyl ether (500 ml). The separated organic layer was washed with water, dried, filtered and the solvent was evaporated. The residue was purified by column chromotoghaphy over silica gel (eluent: $CHCl_3$). The desired fraction was collected and the eluent was evaporated. Yield: 34 g of 6-fluoro-3,4-dihydro-2H-1-benzopyran-2-methanol (interm. 10) (85%).

d) Reaction under $N_2$. To a stirred and cooled (−60° C.; 2-propanone/$CO_2$ bath) mixture of ethanedioyl dichloride (0.1 mol) in $CH_2Cl_2$ (350 ml) was added sulfinylbis[methane] (30 ml) during 10 minutes. After stirring 10 minutes, a mixture of interm. 10 in $CH_2Cl_2$ (90 ml) was added during 5 minutes. After stirring for 15 minutes, N,N-diethylethanamine (125 ml) was added. When the mixture was warmed up to room temperature, it was poured out in water. The product was extracted with $CH_2Cl_2$. The organic layer was wased with water, HCl (1M), water, $NaHCO_3$ (10%) and water, dried and evaporated. The residue was dissolved in diethyl ether, washed with water, dried, filtered and evaporated. The residue was purified by column chromotoghaphy over silica gel (eluent: $CHCl_3$). The desired fraction was collected and the eluent was evaporated. Yield: 21.6 g of 6-fluoro-3,4-dihydro-2H-1-benzopyran-2-carboxaldehyde (interm. 11) (67%).

e) Preparation of

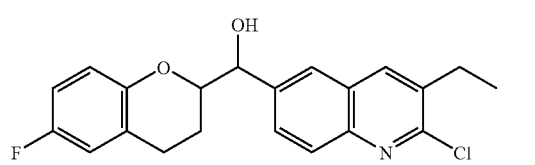
(interm. 12)

nButyllithium 1.6M (0.056 mol) was added slowly at −70° C. to a solution of intermediate (5) (0.046 mol) in THF (100 ml). The mixture was stirred at −70° C. for 30 minutes. A suspension of interm. 11 (0.056 mol) in THF (100 ml) was added slowly. The mixture was stirred at −70° C. for 1 hour, then brought to room temperature, poured out into $H_2O$ and extracted with EtOAc. The organic layer was separated, dried ($MgSO_4$), filtered and the solvent was evaporated. The residue (21 g) was purified by column chromatography over silica gel (eluent: cyclohexane/EtOAc 80/10; 15-35 µm). The pure fractions were collected and the solvent was evaporated. Yield: 9.5 g of interm. 12 (55%).

EXAMPLE A8 a) Preparation of

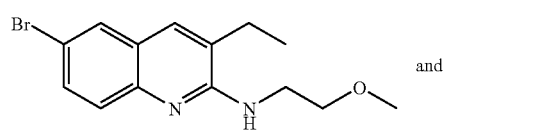
(interm. 13)

and

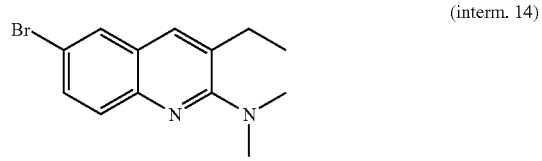
(interm. 14)

A mixture of intermediate (5) (0.1127 mol), 2-methoxyethanamine (0.2254 mol) and $K_2CO_3$ (0.2254 mol) in DMF (500 ml) was stirred at 120° C. for 15 hours and then cooled. The solvent was evaporated. The residue was taken up in $CH_2Cl_2$ and $H_2O$. The organic layer was separated, dried ($MgSO_4$), filtered and the solvent was evaporated till dryness. The residue (33.53 g) was purified by column chromatography over silica gel (eluent: $CH_2Cl_2/CH_3OH$ 99.5/0.5; 15-40

μm). Two fractions were collected and their solvents were evaporated. Yield: 5.7 g of interm. 14 (38%) and interm. 13 (34%).

b) Preparation of

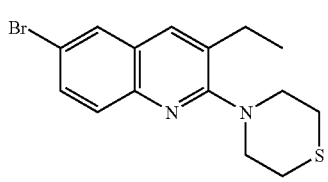
(interm. 15)

A mixture of intermediate (5) (0.0751 mol), thiomorpholine (0.0891 mol) and K$_2$CO$_3$ (0.15 mol) in DMF (200 ml) was stirred at 120° C. for 12 hours. The solvent was evaporated till dryness. The residue was taken up in CH$_2$Cl$_2$ and H$_2$O. The organic layer was separated, dried (MgSO$_4$), filtered and the solvent was evaporated. The residue (26 g) was purified by column chromatography over silica gel (eluent: cyclohexane/EtOAc 80/20; 20-45 μm). Two fractions were collected and their solvents were evaporated. The two fractions were combined. Yield: 9.4 g of interm. 15 (37%); mp. 82° C.

EXAMPLE A9 a) 4-Aminobenzoic acid (0.219 mol) was added to a solution of sodium 3-nitrobenzenesulfonate (0.118 mol) in H$_2$SO$_4$ 70% (230 ml) and the mixture was stirred and refluxed. 2-propene-1,1-diol, 2-methyl-, diacetate (0.216 mol) was added dropwise and the mixture was refluxed for 4 hours. Ethanol (200 ml) was added and the mixture was stirred at 80° C. for 48 hours. The mixture was evaporated, the residue was poured into ice water/NH$_4$OH and extracted with CH$_2$Cl$_2$. The organic layer was dried (MgSO$_4$) and evaporated. The residue was purified by column chromatography over silica gel (eluent: CH$_2$Cl$_2$/2-propanol 99/1). The pure fractions were collected and evaporated. Yield: 21 g of ethyl 3-methyl-6-quinolinecarboxylate (interm. 16) (45%).

b) Interm. 16 (0.098 mol) in THF (270 ml) was added at 0° C. to a solution of LiAlH$_4$ (0.098 mol) in THF under N$_2$. When the addition was complete, water (10 ml) was added. The precipitate was filtered off and washed with CH$_2$Cl$_2$. The organic layer was dried (MgSO$_4$), filtered off and evaporated. The product was used without further purification. Yield: 16.71 g of 3-methyl-6-quinolinemethanol (interm. 17).

c) MnO$_2$ (0.237 mol) was added to a solution of interm. 17 (0.096 mol) in CH$_2$Cl$_2$ (200 ml) and the mixture was stirred at room temperature for 12 hours. The mixture was filtered through celite and the filtrate was stirred again with MnO$_2$ (20 g) for 12 hours. MnO$_2$ (10 g) was added again. The mixture was stirred for 12 hours. The mixture was filtered through celite and evaporated. The product was used without further purification. Yield: 11.71 g of 3-methyl-6-quinolinecarboxaldehyde (71%) (interm. 18).

d) A solution of bromocyclohexyl (0.14 mol) in 1,1'-oxybisethane (50 ml) and Mg turnings (50 ml) was added at 10° C. to a mixture of THF (0.14 mol) in 1,1'-oxybisethane (10 ml). A solution of interm. 18 (0.07 mol) in Mg turnings (100 ml) was added carefully at 5° C., the mixture was poured into ice water and extracted with EtOAc. Yield: 11.34 g of (±)-α-cyclohexyl-3-methyl-6-quinolinemethanol (63%) (interm. 19).

EXAMPLE A10

Preparation of

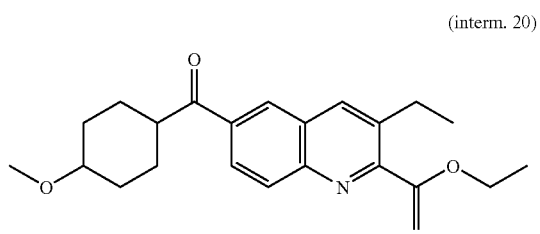
(interm. 20)

A mixture of compound (5) (0.001507 mol), tributyl(1-ethoxyethenyl)stannane (0.00226 mol) and Pd(PPh$_3$)$_4$ (0.000151 mol) in 1,4-dioxane (5 ml) was stirred at 80° C. for 3 hours. Water was added. The mixture was extracted with EtOAc. The organic layer was separated, dried (MgSO$_4$), filtered and the solvent was evaporated. This product was used without further purification. Yield: 1.4 g of interm. 20.

EXAMPLE A11

Preparation of

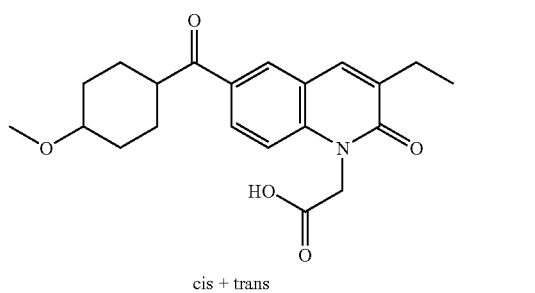
(interm. 21)

cis + trans

A mixture of compound (45) (prepared according to B6) (0.00125 mol) in NaOH 3N (5 ml) and iPrOH (1.7 ml) was stirred at room temperature overnight, then poured out into H$_2$O, acidified with HCl 3N and extracted with EtOAc. The organic layer was separated, dried (MgSO$_4$), filtered and the solvent was evaporated. The residue was taken up in diethyl ether. The precipitate was filtered off and dried. Yielding: 0.26 g of intermediate 21 (56%). (mp.: 232° C.)

EXAMPLE A12 a. Preparation of

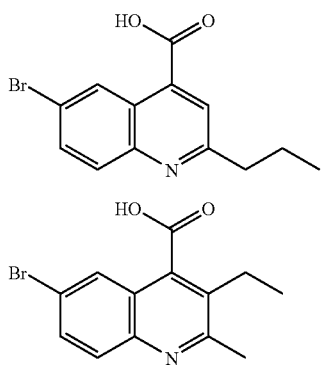

A mixture of 5-bromo-1H-indole-2,3-dione (0.221 mol) in NaOH 3N (500 ml0 was stirred at 80° C. for 30 minutes, brought to room temperature and 2-pentanone (0.221 mol) was added. The mixture was stirred and refluxed for 1 hour and 30 minutes and acidified with AcOH until pH=5. The precipitate was filtered, washed with water and dried. Yielding 52.3 g of intermediate 22 and intermediate 23. (Total yielding: 80%).

b. Preparation of

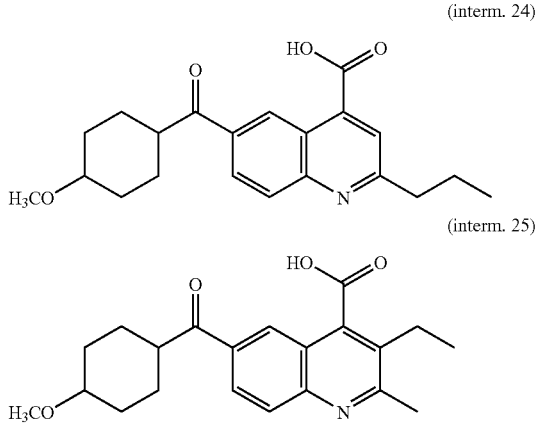

nBuLi 1.6 M (0.0816 mol) was added dropwise at −78° C. to a suspension of intermediate 22 (0.034 mol) and intermediate 23 (0.034 mol) in THF (300 ml) under $N_2$ flow. The mixture was stirred at −78° C. for 30 minutes. nBuLi 1.6M (0.0816 mol) was added dropwise. The mixture was stirred for 1 hour. A mixture of intermediate 9 (0.102 mol) in THF (250 ml) was added slowly. The mixture was stirred for −78° C. to −20° C., poured out into $H_2O$/HCl 3N and extracted with EtOAc. The organic layer was separated, dired (MgSO$_4$), filtered, and the solvent was evaporated till dryness. Yielding: 20.89 g of compound intermediate 24 and intermediate 25 (86%).

EXAMPLE A13 a. Preparation of

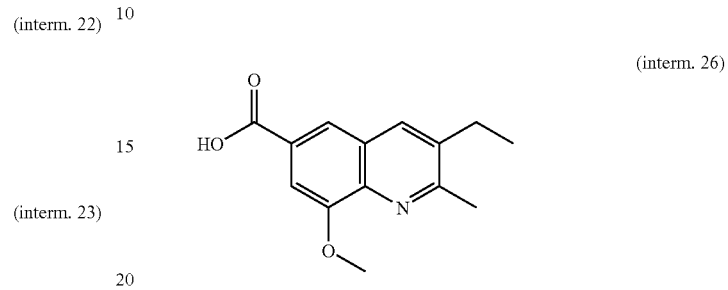

4-amino-3-methoxybenzoic acid (0.054 mol) was added portionwise at room temperature to a solution of 3-chloro-2-ethyl-2-butenal (0.065 mol) in AcOH (100 ml). The mixture was stirred and refluxed for 8 hours and evaporated to dryness. The residue was taken up in $CH_2Cl_2$, water was added and the solution was basified by $Et_3N$. The organic layer was separated, dried (MgSO$_4$), filtered, and the solvent was evaporated. The residue was crystallized from 2-propanone. The precipitate was filtered off and dried. Yielding: 2.5 g of interm. 26 (18%).

b. Preparation of

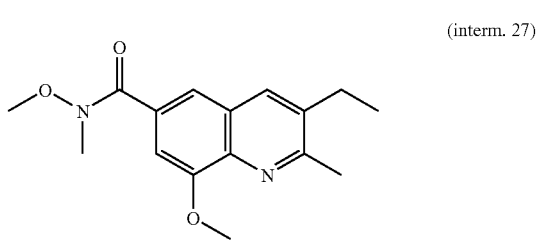

CDI (0.012 mol) was added at room temperature to a solution of interm. 26 (0.011 mol) in $CH_2Cl_2$ (30 ml). The mixture was stirred at room temperature for 1 hour. methoxyaminomethyl (0.012 mol) was added and the mixture was stirred at room temperature for 8 hours. $H_2O$ was added. A precipitate was filtered off. The filtrate was extracted with $CH_2Cl_2$. The organic layer was separated, dried (MgSO$_4$), filtered, and the solvent was evaporated. The residue was crystallized from diethyl ether. The precipitate was filtered off and dried. Yielding: 0.95 g of interm. 27 (31%) (mp.: 148° C.).

EXAMPLE A14

Preparation of

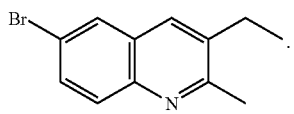
(interm. 28)

4-Bromobenzenamine (0.034 mol) was added at room temperature to a solution of 3-chloride-2-ethyl-2-butanal (0.041 mol) in AcOH (60 ml). The mixture was stirred and refluxed for 8 hours, brought to room temperature and evaporated to dryness. The product was crystallized from EtOAc. The precipitate was filtered, washed with $K_2CO_3$ 10% and taken up in $CH_2Cl_2$. The organic layer was separated, dried ($MgSO_4$), filtered, and the solvent was evaporated. Yielding: 4.6 g of interm. 28 (54%).

EXAMPLE A15 a. Preparation of

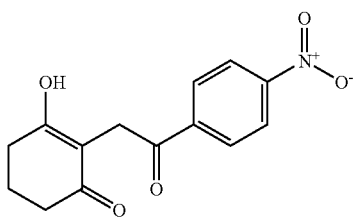
(interm. 29)

A solution of KOH (0.326 mol) in $H_2O$ (150 ml) was added slowly at 5° C. to a solution of 1,3-cyclohexanedione (0.268 mol) in $H_2O$ (150 ml). The temperature must not reach 12° C. KI (2 g) then 2-bromo-1-(4-nitrophenyl)ethanone (0.294 mol) were added portionwise. The mixture was stirred at room temperature for 48 hours. The precipitate was fitered, washed with $H_2O$ then with diethyl ether and dried. Yielding: 63 g (85%). A part of this fraction (1 g) was crystallized from EtOH. The precipitate was filtered off and dried. Yielding: 0.5 g of interm. 29 (42%) (mp.: 100° C.).

b. Preparation of

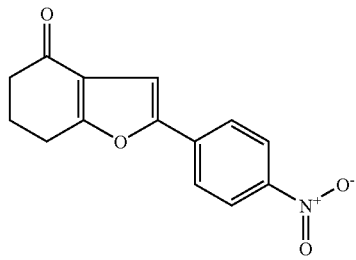
(interm. 30)

A mixture of interm. 29 (0.145 mol) in $H_2SO_4$ (40 ml) was stirred at room temperature for 1 hour, poured out into ice, basified with $NH_4OH$ and extracted with $CH_2Cl_2$. The organic layer was separated, dried ($MgSO_4$), filtered, and the solvent was evaporated. The residue was crystallized from EtOH. The precipitate was filtered off and dried. Yielding: 31 g (58%). A part of this fraction (1 g) was crystallized from EtOH. The precipitate was filtered off and dried. Yielding: 0.7 g of interm. 30 (58%) (mp.: 200° C.).

c. Preparation of

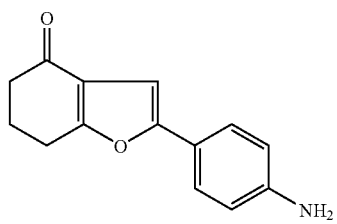
(interm. 31)

A mixture of interm. 30 (0.039 mol), Raney Ni (10 g) in EtOH (100 ml) was hydrogenated at room temperature under a 3 bar pressure for 1 hour. The mixture was filtered over celite and washed with $CH_2Cl_2$. The organic layer was separated, dried ($MgSO_4$), filtered, and the solvent was evaporated. The residue (9.5 g) was crystallized from diethyl ether. The precipitate was filtered off and dried. Yielding: 4.6 g (52%). The filtrate was evaporated. The residue (2.7 g) was purified by column chromatography over silica gel (eluent: $CH_2Cl_2$/$CH_3OH$; 99/1; 15-40 μm). Two fractions were collected and the solvent was evaporated. Yielding: 1.6 g F1 and 1.2 g F2.

F2 was crystallized from EtOH. The precipitate was filtered off and dried. Yielding: 0.24 g of interm. 31 (2%) (mp.: 202° C.).

d. Preparation of

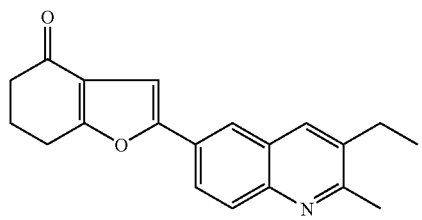
(interm. 32)

Interm. 30 (0.02 mol) was added at room temperature to a solution of 3-chloro-2-ethyl-2-butenal (0.04 mol) in AcOH (50 ml). The mixture was stirred and refluxed for 4 hours. The solvent was evaporated till dryness. The residue was crystallized from EtOAc. The precipitate was filtered off and dried. The residue was taken up in $CH_2Cl_2$. The mixture was basified with $K_2CO_3$ 10% and extracted with $CH_2Cl_2$. The organic layer was separated, dried ($MgSO_4$), filtered, and the solvent was evaporated. The residue was crystallized from EtOH. The precipitate was filtered off and dried. Yielding: 2.5 g of interm. 32 (40%).

EXAMPLE A16

Preparation of

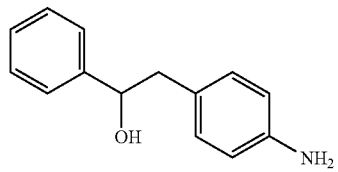
(interm. 33)

A mixture of 2-(4-nitrophenyl)-1-phenylethanone (0.083 mol) and Raney Ni (20 g) in EtOH (200 ml) was hydrogenated at room temperature for 1 hour under a 3 bar pressure, then filtered over celite, washed with $CH_2Cl_2/CH_3OH$ and dried. Yielding: 17.5 g of interm. 33 (97%).

EXAMPLE A17 a. Preparation of

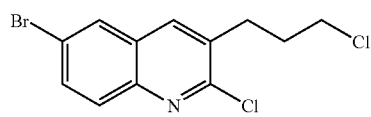
(interm. 34)

DMF (12.4 ml) was added dropwise at 5° C. to $POCl_3$ (0.7536 mol). 4'-bromo-5-chlorovaleranilide (0.1032 mol) was added and the mixture was stirred at 75° C. for 6 hours, cooled at room temperature and poured out into ice water. The insoluble was filtered, washed with water and dried. Yielding: 25.7 g of intermediate 34 (78%).

b. Preparation of

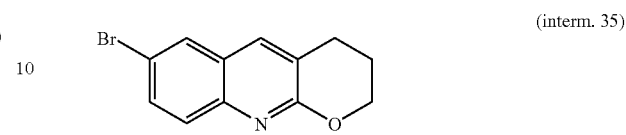
(interm. 35)

A mixture of intermediate 34 (0.094 mol) in HCl 6N (250 ml) was stirred and refluxed for 2 days, cooled, poured out on water (100 ml) and neutralyzed with $NH_4OH$ (concentrated). The insoluble was filtered and washed with water then with EtOH. Yielding: 19 g. The filtrate was evaporated. The residue (9.4 g) was purified by column chromatography over silica gel (eluent: $CH_2Cl_2/CH_3OH$ 99.25/0.75; 15-35 μm). One fraction was collected and the solvent was evaporated. Yielding: 8 g of intermediate 35 (32%).

B. Preparation of the Non-Radioactive Compounds

EXAMPLE B1

Preparation of

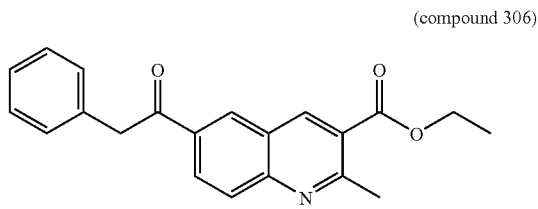
(compound 306)

$POCl_3$ (0.024 mol) was added slowly at 5° C. to DMF (0.024 mol). The mixture was stirred at room temperature for 30 minutes, then cooled to 5° C. 3-Oxo-butanoic acid ethyl ester (0.024 mol) was added slowly. The mixture was stirred at 5° C. for 30 minutes. 1-(4-aminophenyl)-2-phenylethanone (0.024 mol) was added portionwise. The mixture was stirred at 90° C. for 3 hours and dissolved in $CH_2Cl_2$. Ice water was added. The mixture was basified with $NH_4OH$ and extracted with $CH_2Cl_2$. The organic layer was separated, dried ($MgSO_4$), filtered, and the solvent was evaporated. The residue was crystallized from 2-propanone/diethyl ether. The precipitate was filtered off and dried. Yielding: 0.9 g of compound 306 (11%) (mp.: 136° C.).

EXAMPLE B2

Preparation of

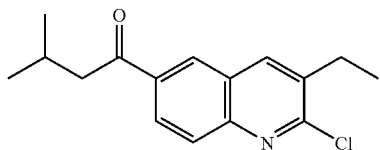
(compound 2)

$KMnO_4$ (10 g) was added portionwise at room temperature to a solution of

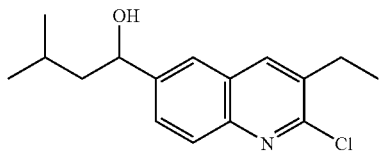

(prepared according to example A7.e) (0.022 mol) in tris (dioxa-3,6-heptyl)amine (1 ml) and $CH_2Cl_2$ (100 ml). The mixture was stirred at room temperature for 8 hours, filtered over celite, washed with $CH_2Cl_2$ and dried. The residue (6 g, 100%) was crystallized from diethyl ether/petroleum ether. The precipitate was filtered off and dried. Yield: 2 g of compound (2) (33%); mp. 82° C.

EXAMPLE B3 a) Preparation of

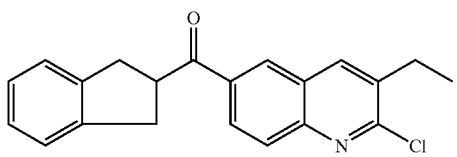
(compound 3)

nBuLi 1.6M (0.07 mol) was added slowly at −70° C. to a solution of intermediate (5) (0.058 mol) in THF (150 ml). The mixture was stirred at −70° C. for 30 minutes. A solution of 2,3-dihydro-1H-Indene-2-carbonitrile (0.07 mol) in THF (100 ml) was added slowly. The mixture was stirred at −70° C. for 1 hour, brought slowly to room temperature, hydrolized with $H_2O$ and extracted with EtOAc. The organic layer was separated, dried ($MgSO_4$), filtered and the solvent was evaporated. The residue (22 g) was purified by column chromatography over silica gel (eluent: $CH_2Cl_2$/cyclohexane 80/20 to 100; 15-35 μm). The pure fractions were collected and the solvent was evaporated. The second fraction was crystallized from 2-propanone/diethyl ether. The precipitate was filtered off and dried. Yield: 0.11 g of compound (3). The filtrate was concentrated. Yield: 0.55 g of compound (3); mp. 145° C.

b) Preparation of

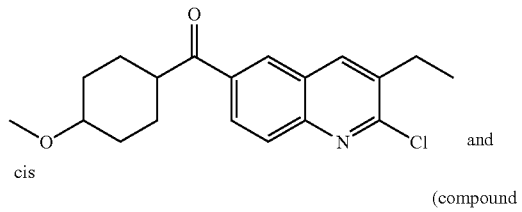
cis (compound 4)

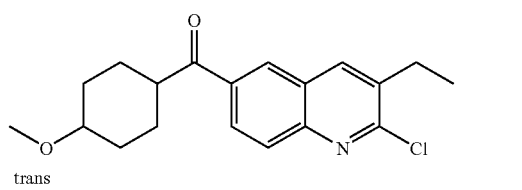
trans (compound 5)

nBuLi 1.6M (0.022 mol) was added slowly at −70° C. to a solution of intermediate (5) (0.018 mol) in THF (50 ml). The mixture was stirred at −70° C. for 1 hour, brought to −40° C., then cooled to −70° C. A solution of interm. 7 (0.018 mol) in THF (40 ml) was added slowly. The mixture was stirred at −70° C. for 1 hour, then brought to −20° C., hydrolyzed with $H_2O$ and extracted with EtOAc. The organic layer was separated, dried ($MgSO_4$), filtered and the solvent was evaporated. The residue (6.5 g) was purified by column chromatography over silica gel (eluent: toluene/EtOAc 90/10; 15-40 μM). Two fractions (F1 and F2) were collected and the solvent was evaporated. F1 (2.4 g) was crystallized from diethyl ether. The precipitate was filtered off and dried. Yield: 1.8 g of compound (4) (29%); mp. 123° C. F2 (0.9 g) was crystallized from diethyl ether. The precipitate was filtered off and dried. Yield: 0.2 g of compound (5) (3%); mp. 120° C.

c) Preparation of

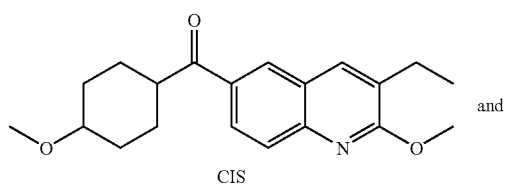
CIS (compound 7)

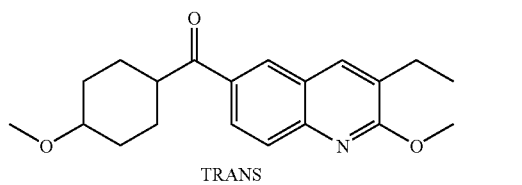
TRANS (compound 8)

nBuLi 1.6M in exane (0.107 mol) was added dropwise at −78° C. under $N_2$ flow to a mixture of intermediate (6) (0.089 mol) in THF. The mixture ws stirred at −78° C. for 1 hour. A mixture of interm. 7 (150 ml) was added at −78° C. under N₂ flow. The mixture was stirred at −78° C. for 2 hours, brought to 0° C., poured out into H₂O and extracted with EtOAc. The organic layer was separated, dried (MgSO₄), filtered and the solvent was evaporated. The residue (31 g) was purified by column chromatography over silica gel (eluent: cyclohexane/ EtOAc 85/15; 20-45 µm). Two pure fractions were collected and their solvents were evaporated. Yielding: 11 g of compound (7) (38%) and 8.2 g of compound (8) (28%).

d) Preparation of

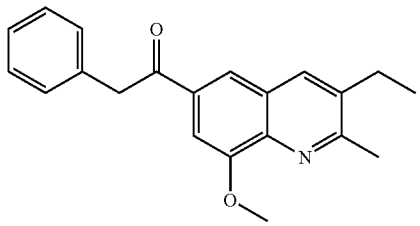

(compound 503)

A solution of chloromethylbenzeen (0.0069 mol) in diethyl ether (8 ml) was added slowly to a suspension of Mg (0.0069 mol) in a small amount of diethyl ether. The mixture was stirred at room temperature for 30 minutes (disparition of Mg), then cooled to 5° C. A solution of interm. 27 (0.0027 mol) in THF (8 ml) was added slowly. The mixture was stirred at 5° C. for 15 minutes, then at room temperature for 2 hours, poured out into H₂O and filtered over celite. The precipitate was washed with EtOAc. The filtrate was extracted with EtOAc. The organic layer was separated, dried (MgSO₄), filtered, and the solvent was evaporated. The residue (1 g) was purified by column chromatography over kromasil (eluent: CH₁Cl₂ 100 to CH₂Cl₂/CH₃OH 99/1; 15-40 µm). The pure fractions were collected and the solvent was evaporated. The residue (0.5 g, 56%) was crystallized from diethyl ether. The precipitate was filtered off and dried. Yielding: 0.14 g of compound 503 (15%).

EXAMPLE B4

Examples of Endgroup Modifications a) Preparation of

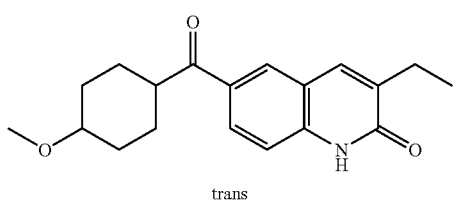

(compound 156)

A mixture of

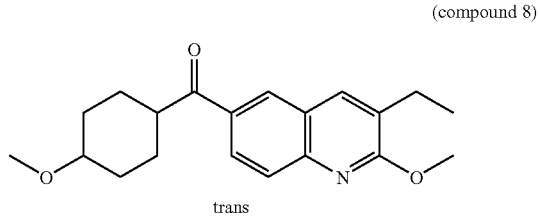

(compound 8)

(prepared according to example B3.c) (0.018 mol) in HCl 3N (60 ml) and THF (60 ml) was stirred at 60° C. overnight. The mixture was basified with a K₂CO₃ 10% solution and extracted with CH₂Cl₂. The organic layer was separated, dried (MgSO₄), filtered and the solvent was evaporated. Yield: 4.6 g of compound (156) (82%).

b) Preparation of

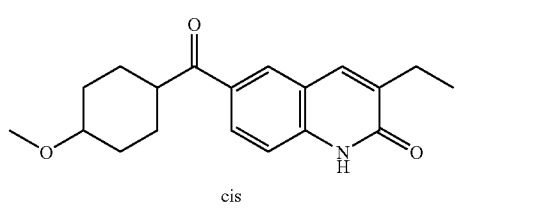

(compound 9)

A mixture of

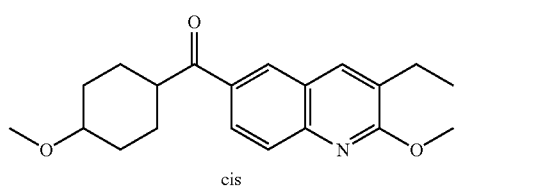

(compound 7)

(prepared according to example B3.c) (0.0122 mol) in HCl 3N (40 ml) and THF (40 ml) was stirred and refluxed overnight, poured out into water, basified with K₂CO₃ 10% and extracted with CH₂Cl₂. The organic layer was separated, dried (MgSO₄), filtered and the solvent was evaporated. The residue was purified by column chromatography over silica gel (eluent: cyclohexane/EtOAc 40/60; 15-40 µm). The pure fractions were collected and the solvent was evaporated. Yield: 2 g of compound (9) (52%); mp. 226° C.

c) Preparation of

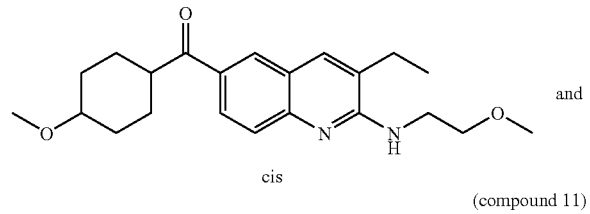

(compound 10)

and (compound 11)

A mixture of compound (4) (0.0015 mol), 2-methoxyethanamine (0.003 mol) and K₂CO₃ (0.003 mol) in DMF (5 ml) was stirred at 140° C. for 48 hours. H₂O was added. The mixture was extracted with EtOAc. The organic layer was separated, dried (MgSO₄), filtered and the solvent was evaporated. The residue (1 g) was purified by column chromatography over silica gel (eluent: cyclohexane/EtOAc 60/40; 15-40 μm). Two fractions were collected and the solvent was evaporated. Both fractions were crystallized separately from pentane. The precipitate was filtered off and dried. Yield: 0.05 g of compound (10) (9%; mp. 115° C.) and 0.057 g of compound (11) (10%; mp. 107° C.).

d) Preparation of

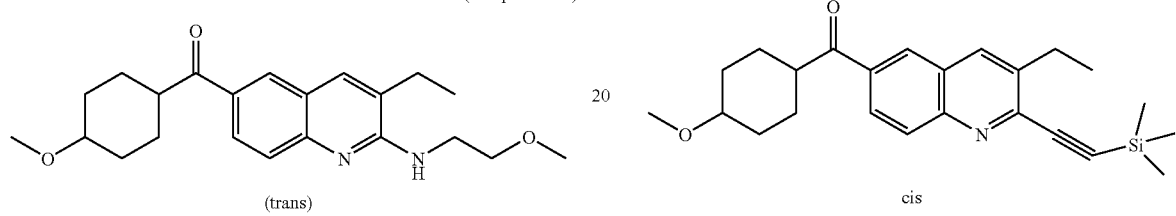

(compound 12)

and (compound 13)

A mixture of compound (4) (0.0015 mol) in 2-(methylthio) ethanamine (2 ml) was stirred at 120° C. for 8 hours. K₂CO₃ 10% was added. The mixture was extracted with CH₂Cl₂. The organic layer was separated, dried (MgSO₄), filtered and the solvent was evaporated. The residue (2.2 g) was purified by column chromatography over silica gel (eluent: cyclohexane/

EtOAc 70/30; 15-40 μm). Two fractions were collected and the solvent was evaporated. The first fraction was crystallized from diethyl ether/petroleum ether. The precipitate was filtered off and dried. Yield: 0.08 g of compound (12) (14%); mp. 120° C. The second fraction was crystallized from diethyl ether. The precipitate was filtered off and dried. Yield: 0.18 g of compound (13) (31%); mp. 125° C., e) Preparation of

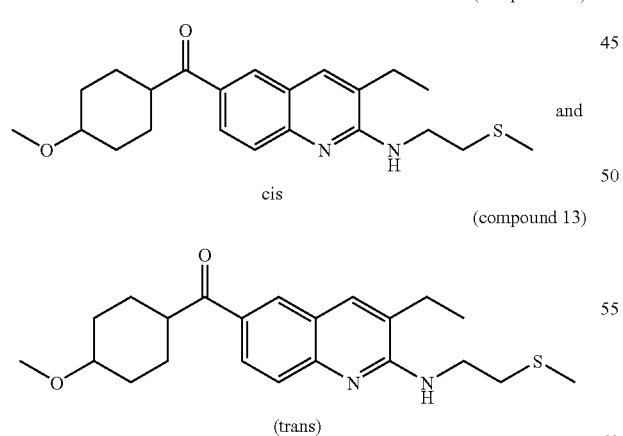

(compound 14)

A mixture of compound (4) (0.001507 mol), ethynyltrimethylsilane (0.003013 mol), CuI (0.000151 mol) and Pd(PPh₃)₄ (0.000151 mol) in N,N-diethylethanamine (5 ml) was stirred at 100° C. for 24 hours. Water was added. The mixture was filtered over celite, washed with EtOAc and the filtrate was extracted with EtOAc. The organic layer was separated, dried (MgSO₄), filtered and the solvent was evaporated. The residue (1.3 g) was purified by column chromatography over silica gel (eluent: cyclohexane/EtOAc 85/15; 15-40 μm). The pure fractions were collected and the solvent was evaporated. The residue (0.3 g) was crystallized from pentane. The precipitate was filtered off and dried. Yield: 0.11 g of compound (14) (18%); mp. 114° C.

f) Preparation of (compound 15)

A mixture of compound (14) (0.013 mol) and KF (0.038 mol) in acetic acid (50 ml) was stirred at room temperature for 2 hours. H₂O was added and the mixture was extracted with diethyl ether. The organic layer was separated, dried (MgSO₄), filtered and the solvent was evaporated. The residue (4.4 g) was purified by column chromatography over silica gel (eluent: cyclohexane/EtOAc 70/30; 15-40 μm). One fraction was collected and the solvent was evaporated. This fraction (3 g, 73%) was crystallized from diethyl ether. The precipitate was filtered off and dried. Yield: 2.45 g of compound (15) (60%); mp. 132° C.

g) Preparation of

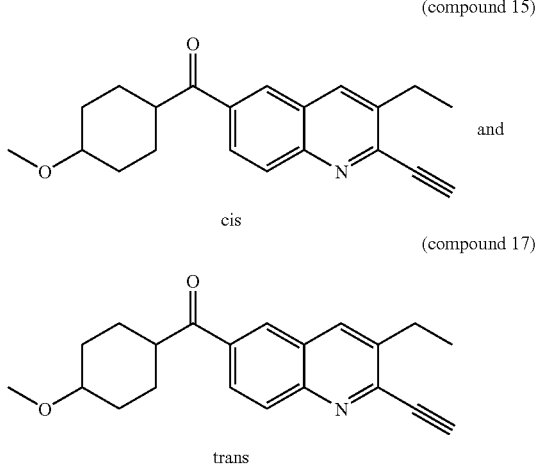

A mixture of

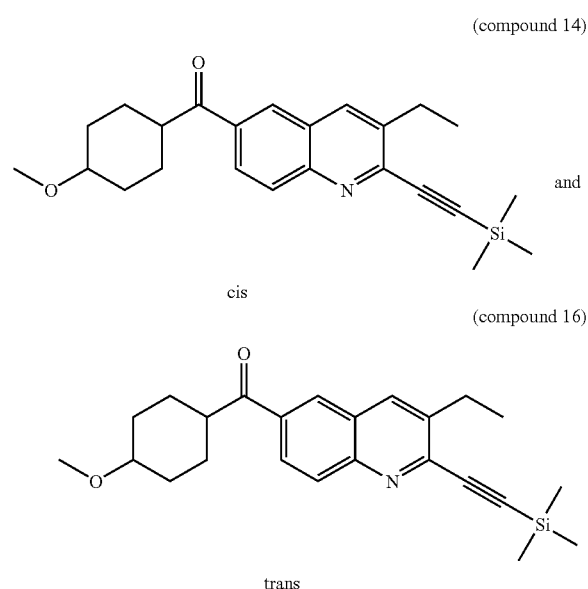

prepared according to example B.7.a) (0.0056 mol) in KOH [1M, H₂O] (10 ml) and methanol (30 ml) was stirred at room temperature for 1 hour, poured out into water and extracted with EtOAc. The organic layer was separated, dried (MgSO₄), filtered and the solvent was evaporated. The residue (2.2 g) was purified by column chromatography over silica gel (eluent: cyclohexane/EtOAc 85/15 to 70/30; 15-40 μm). Two fractions were collected and the solvent was evaporated.

The first fraction was crystallized from diethyl ether. The precipitate was filtered off and dried. Yield: 0.2 g of compound (15) (11%); mp. 133° C. The second fraction was crystallized from diethyl ether. The precipitate was filtered off and dried. Yield: 0.3 g of compound (17) (16%); mp. 128° C.

h) Preparation of

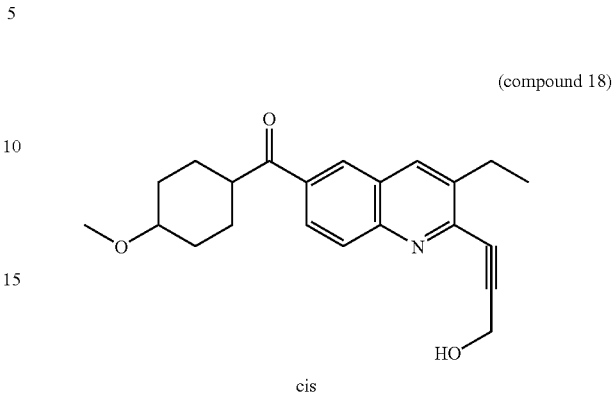

A mixture of compound (4) (0.001205 mol), 2-propyn-1-ol (0.002411 mol), Pd(PPh₃)₄ (0.000121 mol) and CuI (0.000121 mol) in N,N-diethylethanamine (5 ml) was stirred at 100° C. for 2 hours. Water was added. The mixture was filtered over celite, washed with EtOAc and extracted aith EtOAc. The organic layer was separated, dried (MgSO₄), filtered and the solvent was evaporated. The residue (0.7 g) was purified by column chromatography over silica gel (eluent: CH₂Cl₂/CH₃OH 98/2; 15-40 μm). The pure fractions were collected and the solvent was evaporated. The residue was crystallized from petroleum ether and diethyl ether. The precipitate was filtered off and dried. Yield: 0.1 g of compound (18) (23%); mp. 113° C.

i) Preparation of

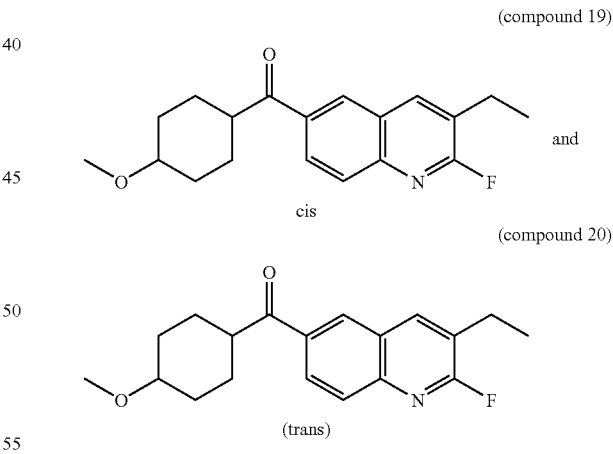

A mixture of compound (4) (0.006027 mol) and KF (0.024108 mol) in DMSO (20 ml) was stirred at 140° C. The solvent was evaporated till dryness. The residue was solidified in water and diethyl ether. The mixture was extracted with diethyl ether. The organic layer was separated, washed with diethyl ether, washed with a saturated solution of NaCl, dried (MgSO₄), filtered and the solvent was evaporated. The residue (1.7 g) was purified by column chromatography over silica gel (eluent: cyclohexane/EtOAc 85/15; 15-40 μm). Three fractions were collected and their solvents were evaporated.

The first fraction was crystallized from petroleum ether. The precipitate was filtered off and dried. Yield: 0.21 g of compound (19) (11%); mp. 92° C.

The second fraction was crystallized from petroleum ether. The precipitate was filtered off and dried. Yield: 0.33 g of compound (20) (17%); mp. 114° C., j) Preparation of

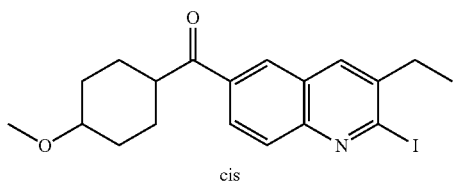

(compound 21)

A mixture of compound (4) (0.003013 mol), acetyl chloride (0.003315 mol) and sodium iodide (0.006027 mol) in CH$_3$CN (10 ml) was stirred and refluxed for 1 hour. K$_2$CO$_3$ 10% was added. The mixture was extracted with CH$_2$Cl$_2$. The organic layer was separated, dried (MgSO$_4$), filtered and the solvent was evaporated. The residue (1 g) was purified by column chromatography over silica gel (eluent: cyclohexane/EtOAc 80/20; 15-40 μm). Two fractions were collected and their solvents were evaporated. The first fraction was crystallized from petroleum ether. The precipitate was filtered off and dried. Yield: 0.12 g of compound (21); mp. 110° C., k) Preparation of

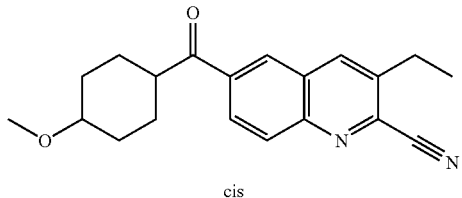

(compound 22)

A mixture of compound (21) (0.000898 mol), trimethylsilanecarbonitrile (0.001347 mol) and Pd(PPh$_3$)$_4$ (0.00009 mol) in N,N-diethylethanamine (5 ml) was stirred at 100° C. for 2 hours. Water was added. The mixture was extracted with EtOAc. The organic layer was separated, dried (MgSO$_4$). filtered and the solvent was evaporated. The residue (0.4 g) was purified by column chromatography over silica gel (eluent: cyclohexane/EtOAc 80/20; 15-40 μm). The pure fractions were collected and the solvent was evaporated. The residue (0.18 g, 62%) was crystallized from petroleum ether.

The precipitate was filtered off and dried. Yield: 0.13 g of compound (22) (45%); mp. 138° C.

l) Preparation of

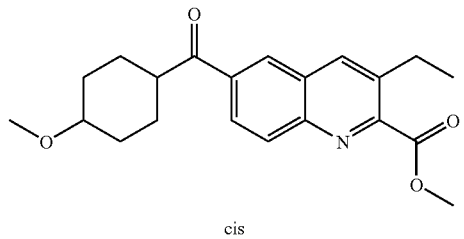

(compound 23)

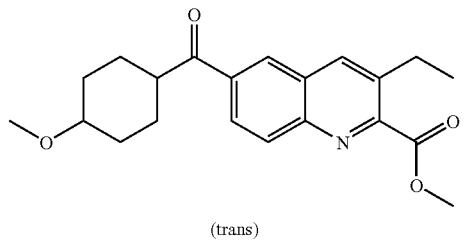

(compound 24)

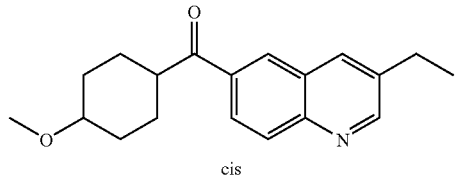

(compound 25)

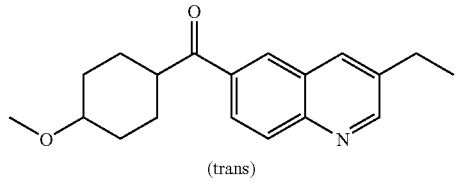

(compound 26)

A mixture of compound (4) (0.00603 mol), Pd(OAc)$_2$ (0.000603 mol), PPh$_3$ (0.00904 mol) and K$_2$CO$_3$ (0.012054 mol) in CO (gas) and methanol (40 ml) was stirred at 90° C. for 8 hours under a 5 bar pressure of CO. H$_2$O was added. The mixture was extracted with EtOAc. The organic layer was separated, dried (MgSO$_4$), filtered and the solvent was evaporated. The residue (6 g) was purified by column chromatography over silica gel (eluent: CH$_2$Cl$_2$/CH$_3$OH 100/0 to 98/2; 15-35 μm). Four fractions (F1-F4) were collected and the solvent was evaporated. Yield: 0.13 g (cis) F1; 0.02 g F2 (cis, compound 25); 0.055 g F3 (trans, 3%) and 0.11 g F4 (trans; compound 26).

F1 was crystallized from petroleum ether. The precipitate was filtered off and dried. Yield: 0.03 g of compound (23) (1%); mp. 91° C.

F3 was crystallized from petroleum ether. The precipitate was filtered off and dried. Yield: 0.035 g of compound (24) (1%); mp. 99° C.

m) Preparation of

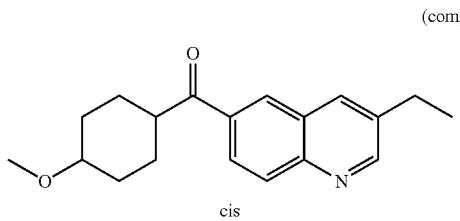
(compound 25)

cis

A mixture of compound (4) (0.009 mol) and Zn (0.027 mol) in acetic acid (30 ml) was stirred at 60° C. for 4 hours, filtered over celite, washed with $CH_2Cl_2$, evaporated till dryness, solubilized in $CH_2Cl_2$ and washed with $K_2CO_3$ 10%. The organic layer was separated, dried ($MgSO_4$), filtered and the solvent was evaporated. The residue (4 g) was purified by column chromatography over silica gel (eluent: cyclohexane/EtOAc 75/25; 15-40 μm). One fraction was collected and the solvent was evaporated. This fraction (1 g 37%) was crystallized from petroleum ether. The precipitate was filtered off and dried. Yield: compound (25); mp. 88° C.

n) Preparation of

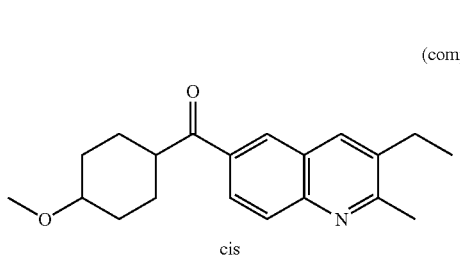
(compound 27)

cis

A mixture of compound (4) (0.001502 mol), $Sn(CH_3)_4$ (0.003004 mol) and $Pd(PPh_3)_4$ (0.00015 mol) in methylbenzene (5 ml) was stirred and refluxed for 3 hours. $K_2CO_3$ 10% was added. The mixture was extracted with EtOAc. The organic layer was separated, dried ($MgSO_4$), filtered and the solvent was evaporated. The residue (0.7 g) was purified by column chromatography over silica gel (eluent: cyclohexane/EtOAc 85/15; 15-40 μm). Two fractions (F1 and F2) were collected and their solvents were evaporated. Yield: 0.27 g (F1, starting material) and 0.14 g (F2). F2 was crystallized from pentane and petroleum ether. The precipitate was filtered off and dried. Yield: 0.08 g of compound (27) (17%); mp. 110° C.

o) Preparation of

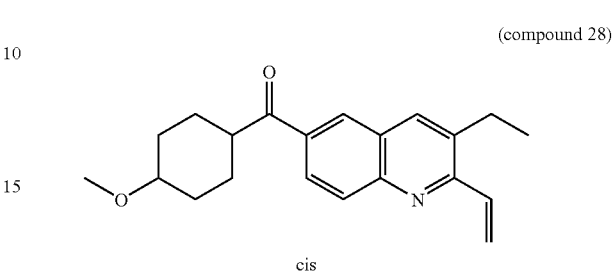
(compound 28)

cis

A mixture of compound (4) (0.001507 mol), tributylethenylstannane (0.002260 mol) and $Pd(PPh_3)_4$ (0.000151 mol) in dioxane (5 ml) was stirred at 80° C. for 8 hours. Water was added. The mixture was filtered over celite, washed with EtOAc and extracted with EtOAc. The organic layer was separated, dried ($MgSO_4$), filtered and the solvent was evaporated. The residue (0.65 g) was purified by column chromatography over silica gel (eluent: cyclohexane/EtOAc 90/10; 15-40 μm). The pure fractions were collected and the solvent was evaporated. The residue was crystallized from petroleum ether. The precipitate was filtered off and dried. Yield: 0.07 g of compound (28) (14%); mp. 108° C.

p) Preparation of

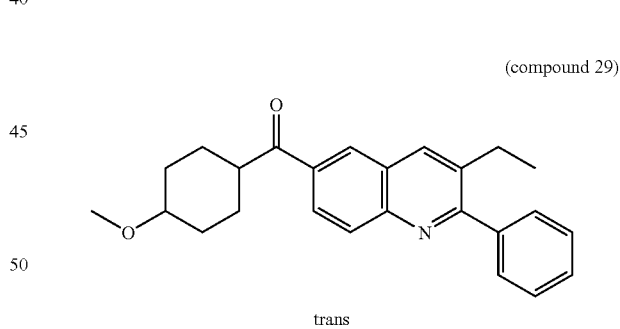
(compound 29)

trans

A mixture of compound (5) (0.001507 mol), triphenyl (phenylmethyl)stannane (0.002260 mol) and $Pd(PPh_3)_4$ (0.000151 mol) in dioxane (5 ml) was stirred at 80° C. for 8 hours. Water was added. The mixture was extracted with EtOAc. The organic layer was separated, dried ($MgSO_4$), filtered and the solvent was evaporated. The residue (1.4 g) was purified by column chromatography over silica gel (eluent: $CH_2Cl_2$/EtOAc 96/4; 15-40 μm). The pure fractions were collected and the solvent was evaporated. The residue (0.38 g)

was crystallized from petroleum ether. The precipitate was filtered off and dried. Yield: 0.16 g of compound (29) (28%); mp. 112° C.

q) Preparation of (compound 30)

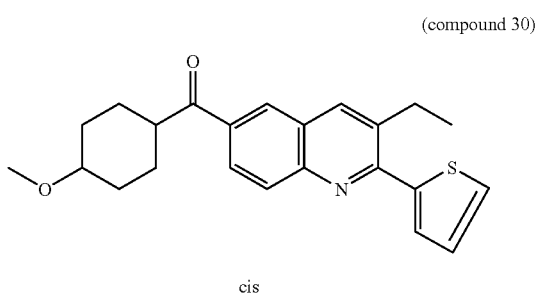

cis

A mixture of compound (4) (0.001507 mol), tributyl-2-thienylstannane (0.00226 mol) and Pd(PPh$_3$)$_4$ (0.0001507 mol) in dioxane (5 ml) was stirred at 80° C. for 8 hours. K$_2$CO$_3$ 10% was added. The mixture was extracted with EtOAc. The organic layer was separated, dried (MgSO$_4$), filtered and the solvent was evaporated. The residue (1.7 g) was purified by column chromatography over silica gel (eluent: cyclohexane/EtOAc 85/15; 15-40 μm). The pure fractions were collected and the solvent was evaporated. The residue (0.65 g) was crystallized from diethyl ether. The precipitate was filtered off and dried. Yield: 0.35 g of compound (30) (61%); mp. 142° C.

r) Preparation of (compound 31)

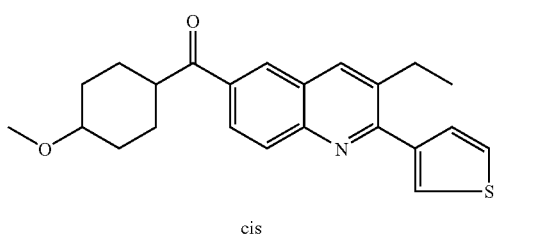

cis

A mixture of compound (4) (0.0015 mol), 3-thienyl boronic acid (0.00226 mol), Pd(PPh$_3$)$_4$ (0.00015 mol) and dioxane was stirred and refluxed for 24 hours. K$_2$CO$_3$ 10% was added. The mixture was extracted with EtOAc. The organic layer was separated, dried (MgSO$_4$), filtered and the solvent was evaporated. The residue (0.8 g) was purified by column chromatography over silica gel (eluent: cyclohexane/EtOAc 80/20; 15-40 μm). The pure fractions were collected and the solvent was evaporated. The residue (0.4 g, 70%) was crystallized from petroleum ether. The precipitate was filtered off and dried. Yield: 0.39 g of compound (31) (68%); mp. 113° C.

s) Preparation of (compound 32)

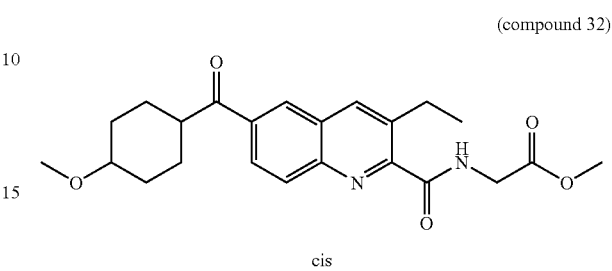

cis

A mixture of compound (4) (0.003 mol), glycine methyl ester monohydrochloride (0.0066 mol) and Pd(PPh$_3$)$_4$ (0.0003 mol) in Et$_3$N (2 ml) and toluene (10 ml) was stirred at 100° C. under 5 bar pressure of CO for 8 hours, filtered over celite, washed with CH$_2$Cl$_2$ and evaporated. The residue (2 g) was purified by column chromatography over silica gel (eluent: cyclohexane/EtOAc 80/20; 75-35 μm). One fraction was collected and the solvent was evaporated. This fraction (1 g 80%) was crystallized from diethyl ether. The precipitate was filtered off and dried. Yielding: 0.46 g of compound (32) (37%).

t) Preparation of (compound 33)

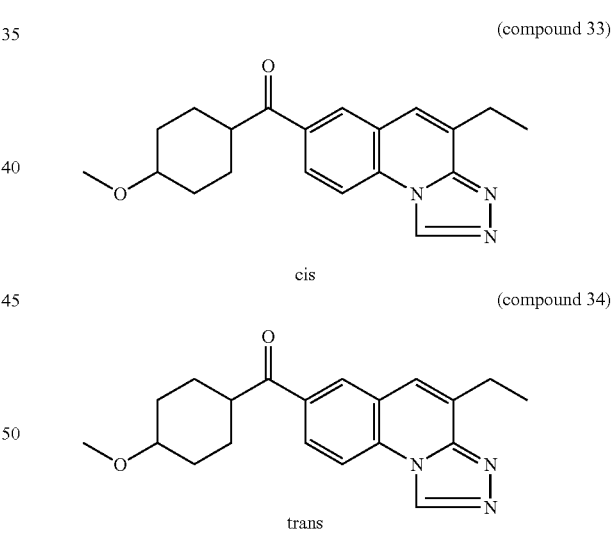

A mixture of compound (4) (0.003 mol) and hydrazinecarboxaldehyde (0.0045 mol) in 1-butanol (15 ml) was stirred and refluxed overnight, poured out into water and extracted with CH$_2$Cl$_2$. The organic layer was separated, dried (MgSO$_4$), filtered and the solvent was evaporated. The residue was purified by column chromatography over silica gel (eluent: CH$_2$Cl$_2$/CH$_3$OH/NH$_4$OH 95/5/0.1; 15-40 μm). Two fractions (F1 and F2) were collected and their solvents were evaporated. Yield: 0.3 g F1 and 0.3 g F2.

F1 was crystallized from CH$_3$CN and diethyl ether. The precipitate was filtered off and dried. Yield: 0.102 g of compound (33); mp. 224° C.

F2 was crystallized from CH₃CN and diethyl ether. The precipitate was filtered off and dried. Yield: 0.2 g of compound (34); mp. 185° C., u) Preparation of

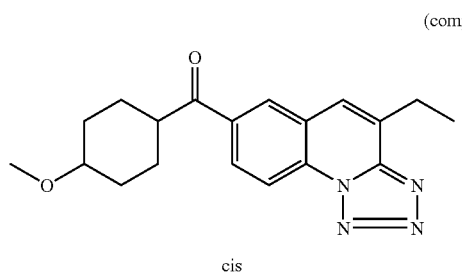
(compound 35)

cis

A mixture of compound 4 (0.015 mol) and NaN₃ (0.045 mol) in DMF (50 ml) was stirred at 140° C. for 2 hours. K₂CO₃ 10% was added and the mixture was extracted with EtOAc. The organic layer was separated, dried (MgSO₄), filtered and the solvent was evaporated. The residue (6 g) was purified by column chromatography over silica gel (eluent: cyclohexane/EtOAc 60/40; 15-40 μm). The first fraction was collected and the solvent was evaporated. The residue was crystallized from diethyl ether. The precipitate was filtered off and dried. Yield: 1.26 g of compound (35) (24%); mp. 160° C.

v) Preparation of

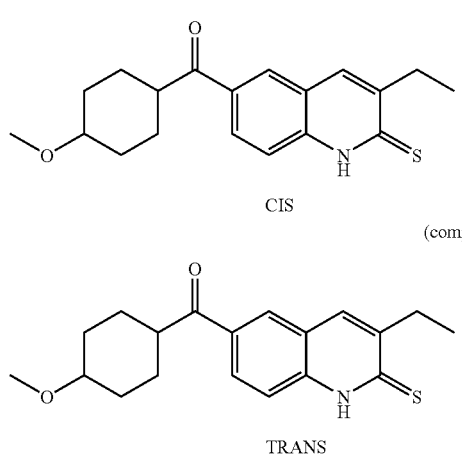

(compound 36)

CIS (compound 37)

TRANS

A mixture of compound (4) (0.009 mol) and thiourea (0.0099 mol) in ethyl alcohol (30 ml) was stirred and refluxed for 12 hours and a solution of KOH (0.0149 mol) in H₂O (5 ml) was added slowly. The mixture was stirred and refluxed for 1 hour, poured out into water and extracted with CH₂Cl₂. The organic layer was separated, dried (MgSO₄), filtered and the solvent was evaporated. The residue was purified by column chromatography over silica gel (cyclohexane/EtOAc 70/30; 15-40 μm). The pure fractions were collected and the solvent was evaporated. Yielding: 1.1 g of F1 (37%) and 0.4 g of F2 (13%). F1 was crystallized from 2-propanone. The precipitate was filtered off and dried. Yielding: compound (36). F2 was crystallized from 2-propanone. The precipitate was filtered off and dried. Yielding: compound (37).

w) Preparation of

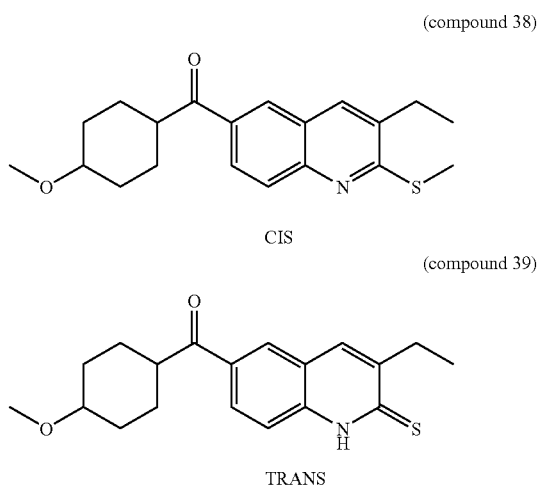

(compound 38)

CIS (compound 39)

TRANS

CH₃I (0.0034 mol) was added slowly at room temperature to a solution of compound (36) (0.0015 mol), compound (37) (0.0015 mol) and K₂CO₃ (0.0034 mol) in acetone (15 ml). The mixture was stirred at room temperature for 8 hours. Water was added and the mixture was extracted with CH₂Cl₂. The organic layer was separated, dried (MgSO₄), filtered and the solvent was evaporated. The residue (1.2 g) was purified by column chromatography over silica gel (eluent: cyclohexane/EtOAc 85/15; 15-40 μm). The pure fractions were collected and the solvent was evaporated. Yielding: 0.6 g F1 (57%), and 0.18 g F2 (17%). F1 was crystallized from diethyl ether. The precipitate was filtered off and dried. Yielding: 0.28 g compound (38) (27%). F2 was crystallized from diethyl ether. The precipitate was filtered off and dried. Yielding: 0.065 g of compound (39) (6%).

x) Preparation of

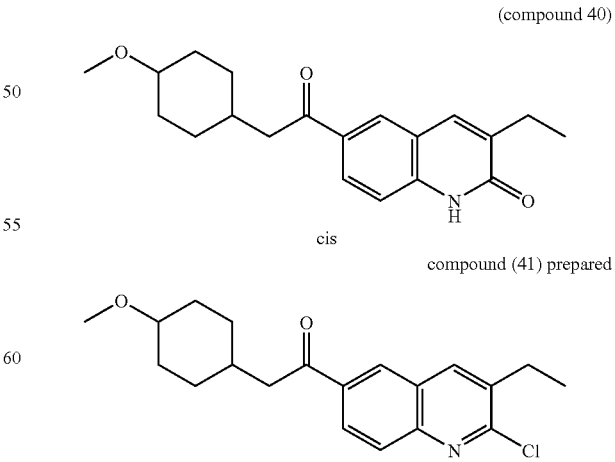

(compound 40)

cis compound (41) prepared

A mixture of according to example B3.b (0.0014 mol) in HCl 3N (5 ml) and THF (5 ml) was stirred and refluxed for a weekend, then poured out into H₂O, basified with K₂CO₃ and extracted with CH₂Cl₂. The organic layer was separated, dried (MgSO₄), filtered and the solvent was evaporated. Yielding: 0.5 g of F. This fraction F was crystallized from 2-propanone. The precipitate was filtered off and dried. Yielding: 0.35 g of compound (40) (74%).

y) Preparation of

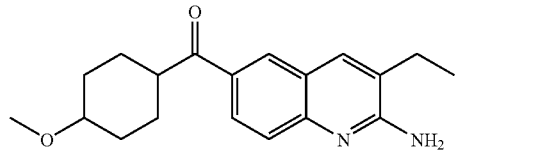
(compound 188)

A mixture of compound (5) (0.045 mol), acetamide (0.90013 mol) and K₂CO₃ (0.225 mol) was stirred and refluxed at 200° C. for 2 hours, cooled at room temperature, poured out into H₂O/CH₂Cl₂; and extracted with CH₂Cl₂. The organic layer was separated, dried (MgSO₄), filtered and the solvent was evaporated till dryness. The residue (14.4 g) was crystallized from CH₃OH. The precipitate was filtered off and dried. The filtrate was evaporated. The residue (11.27 g) was purified by column chromatography over silica gel (eluent: CH₂Cl₂/CH₃OH/NH₄OH 96/4/0.1; 15-35 μm). The pure fractions were collected and the solvent was evaporated. Yielding: 4.2 g of compound (188) (65%).

z) Preparation of

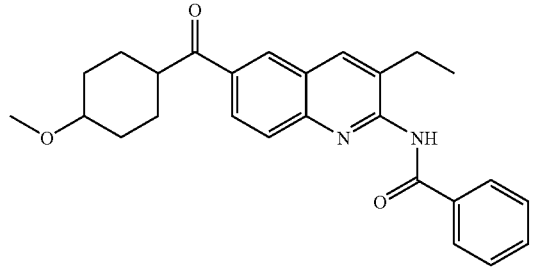
(compound 248)

A mixture of compound (188) (0.00032 mol), benzoic acid (1.5 equiv., 0.00048 mol), 1-ethyl-3-(3'-dimethylaminopropyl)carbodiimide .HCl (1:1) (1.5 equiv., 0.00048 mol), N-hydroxybenzotriazole (1.5 equiv., 0.00048 mol) and Et₃N (1 equiv., 0.00032 mol) in CH₂CL₂ (2 ml) was stirred at room temperature for 15 hours. The solvent was evaporated. The residue was purified by HPLC and the product fractions were collected and the solvent was evaporated. Yield: 0.066 g of compound (205) (49.50%).

aa) Preparation of

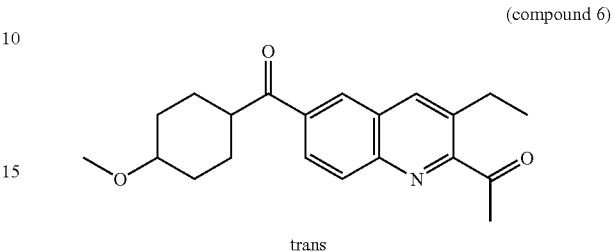
(compound 6)

trans

A mixture of interm. 20 (0.001507 mol) in HCl 3N (10 ml) and THF (10 ml) was stirred at room temperature for 8 hours, basified with K₂CO₃ 10% and extracted with CH₂Cl₂. The organic layer was separated, dried (MgSO₄), filtered and the solvent was evaporated. The residue (1.2 g) was purified by column chromatography over silica gel (eluent: cyclohexane/EtOAc 85/15; 15-40 μm). The pure fractions were collected and the solvent was evaporated. The residue (0.4 g) was crystallized from petroleum ether. The precipitate was filtered off and dried. Yield: 0.3 g of compound (6) (58%); mp. 108° C.

ab) Preparation of

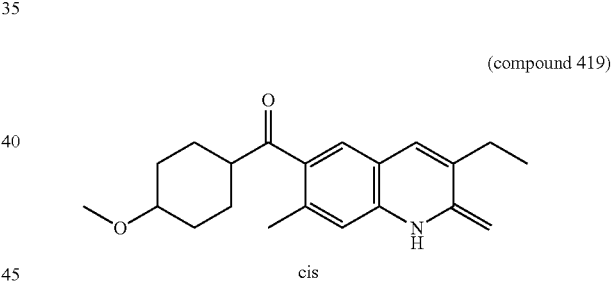
(compound 419)

cis

A mixture of compound 213 (prepared according to B4) (0.00305 mol) and CH₃ONa (30% in CH₃OH) (0.00916 mol) in CH₃OH (25 ml) was stirred and refluxed for 15 hours then cooled to room temperature, poured out into H₂O and extracted with EtOAc. The organic layer was separated, dried (MgSO₄), filtered, and the solvent was evaporated till dryness. The residue (1.1 g) was purified by column chromatography over silica gel (eluent: cyclohexane/EtOAc; 40/60; 15-40 μm). Two fractions were collected and the solvent was evaporated. Yielding: 0.3 g F1 and 0.5 g F2 (50%) F2 was crystallized from diethyl ether/petroleum ether. The precipitate was filtered off and dried. Yielding: 0.26 g F1 was crystallized from pentane. The precipitate was filtered off and dried. Yielding: 0.19 g. This fraction was purified by column chromatography over silica gel (eluent: CH₂Cl₂/CH₃OH; 98/2; 15-40 μm). The pure fractions were collected and the solvent was evaporated. Yielding: 0.11 g. This fraction was purified by column chromatography over kromasil (eluent: CH₃OH/H₂O; 70/30). The pure fractions were collected and the solvent was evaporated. Yielding: 0.09 g. (9%) This fraction was crystallized from diethyl ether. The precipitate was filtered off and dried. Yielding: 0.08 g of compound 419 (8%).

EXAMPLE B5

Preparation of (compound 42)

(compound 43)

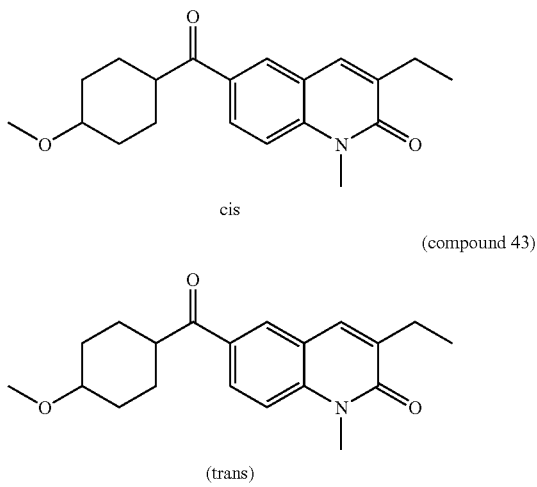

Iodomethane (0.00456 mol) was added at 5° C. to a mixture of compound (9) (0.0019 mol), compound (8) (0.0019 mol) and tBuOK (0.00456 mol) in THF (30 ml) under N$_2$ flow. The mixture was stirred at room temperature overnight, poured out into H$_2$O and extracted with CH$_2$Cl$_2$. The organic layer was separated, dried (MgSO$_4$), filtered and the solvent was evaporated. The residue was purified by column chromatography over silica gel (eluent: cyclohexane/EtOAc 65/35; 15-40 μm). Two fractions were collected and the solvent was evaporated. Yield: 0.35 g of compound (42) (30%; mp. 125° C.) and 0.35 g of compound (43) (30%; mp. 116° C.).

EXAMPLE B6 a) Preparation of (compound 44)

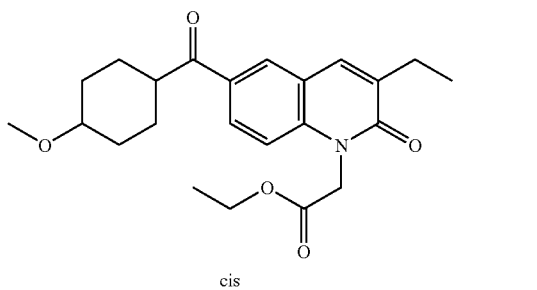

(compound 45)

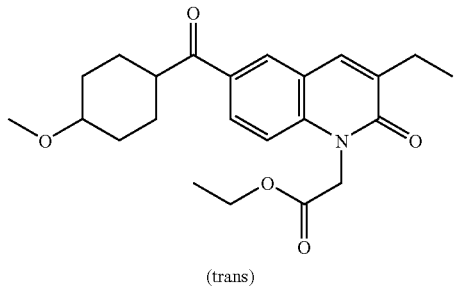

NaH 60% (0.01068 mol) was added at 0° C. under N$_2$ flow to a mixture of compound (8) and compound (9) (0.0089 mol). The mixture was stirred for 30 minutes. Ethyl bromoacetate (0.01068 mol) was added at 0° C. The mixture was stirred at room temperature for 1 hour, hydrolized with water and extracted with EtOAc. The organic layer was separated, dried (MgSO$_4$), filtered and the solvent was evaporated. The residue was purified by column chromatography over silica gel (eluent: cyclohexane/EtOAc 60/40; 15-40 μm). The desired fractions (F1-F4) were collected and the solvent was evaporated. Yield: 0.11 g F 1; 0.13 g F2; 0.75 g F3 and 0.8 g F4.

F3 was crystallized from diethyl ether. The precipitate was filtered off and dried. Yield: compound (44); mp. 152° C.

F4 was crystallized from diethyl ether. The precipitate was filtered off and dried. Yield: compound (45); mp. 147° C.

b) Preparation of (compound 46)

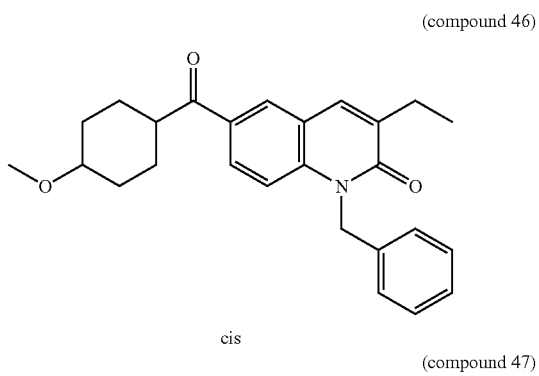

(compound 47)

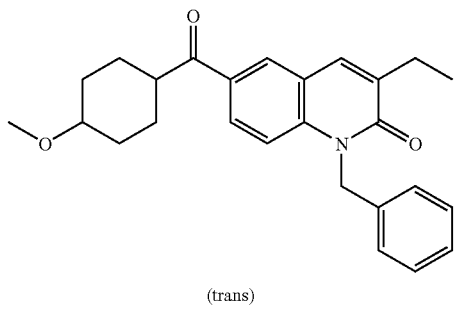

Bromomethylbenzene (0.007 mol) was added dropwise at 0° C. under N$_2$ flow to a solution of compound (8) and compound (9) (0.0064 mol) and NaH 60% (0.007 mol) in DMF (40 ml). The mixture was stirred at room temperature for 1 hour, hydrolized with water and extracted with EtOAc. The organic layer was separated, washed with water, dried (MgSO₄), filtered and the solvent was evaporated. The residue was purified by column chromatography over silica gel (eluent: cyclohexane/EtOAc 70/30; 15-40 μm). The desired fractions (F1-F4) were collected and the solvent was evaporated. Yield: 0.15 g F1, 0.11 g F2, 0.6 g F3 (23%) and 0.8 g F4.

F3 was crystallized from diethyl ether. The precipitate was filtered off and dried. Yield: 0.13 g of compound (46); mp. 137° C.

F4 was crystallized from DIPE and petroleum ether. The precipitate was filtered off and dried. Yield: compound (47); mp. 130° C.

EXAMPLE B7 a) 3-Chlorobenzenecarboperoxoic acid (0.088 mol) was added at 0° C. to a solution of compound (48) (prepared according to example B2) (0.044 mol) in CH₂Cl₂ (200 ml) and the mixture was stirred at room temperature for 12 hours. The mixture was washed with K₂CO₃ 10%. The organic layer was dried (MgSO₄), filtered off and evaporated. The residue was recrystallized from (C₂H₅)₂O. Yield: 8.2 g of cyclohexyl (3-methyl-6-quinolinyl)methanone, 1-oxide (compound 49) (69%).

b) 4-Methyl benzenesulfonyl chloride (0.043 mol) was added to a solution of compound (49) (0.028 mol) in K₂CO₃ (400 ml) and CH₂Cl₂ (400 ml) and the mixture was stirred at room temperature for 1 hour. The mixture was extracted with CH₂Cl₂. The organic layer was dried (MgSO₄), filtered off and evaporated. The residue was recrystallized from (C₂H₅)₂O. Yield: 6.64 g of 6-(cyclohexylcarbonyl)-3-methyl-2(1H)-quinolinone (compound 50) (85%); mp. 256.1° C.

EXAMPLE B8 a) Preparation of

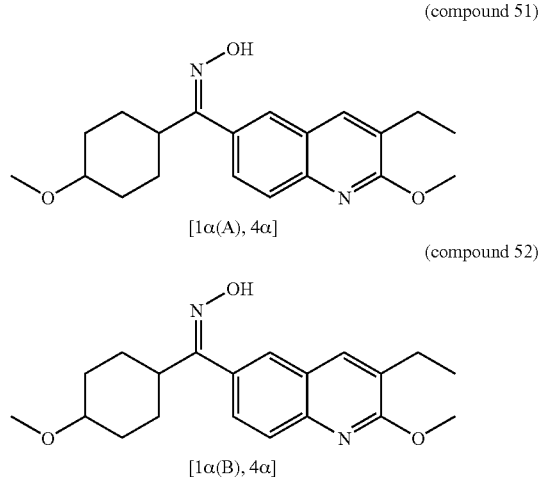

evaporated. The residue was crystallized from CH₃CN. The precipitate was filtered off and dried. The residue was purified by column chromatography over silica gel (eluent: CH₂Cl₂/EtOAc 80/20; 15-40 μm). Two fractions were collected and the solvent was evaporated. Yielding: 2.8 g of compound (51) (36%; mp. 133° C.) and 3 g of compound (52) (38%; mp. 142° C.).

b) Preparation of

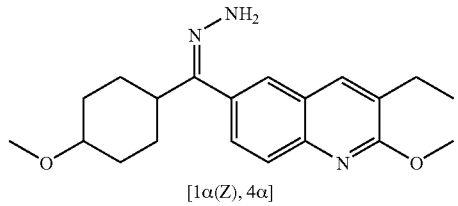

Hydrazine (0.41 mol) was added at room temperature to a solution of compound (7) (0.015 mol) in ethanol (75 ml). The mixture was stirred and refluxed for 1 night, poured out into water and extracted with CH₂Cl₂. The organic layer was separated, dried (MgSO₄), filtered and the solvent was evaporated. The residue was purified by column chromatography over silica gel (eluent: CH₂Cl₂/CH₃OH/NH₄OH 98/2/0.1). The pure fractions were collected and the solvent was evaporated. The residue was crystallized from diethyl ether. The precipitate was filtered off and dried. Yielding: 0.8 g of compound (53) (15%); mp. 110° C.

EXAMPLE B9

Preparation of

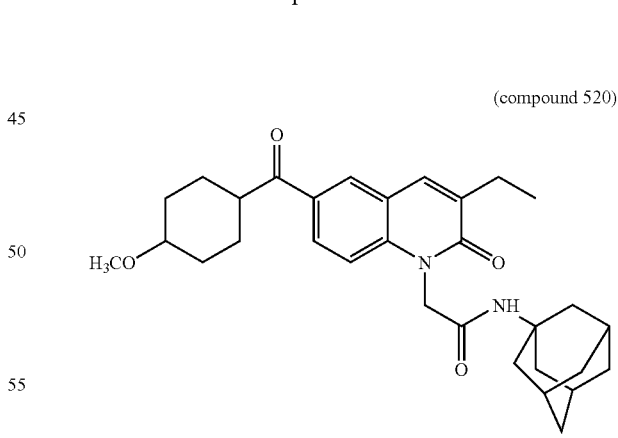

A mixture of compound (7) (0.0229 mol), hydroxylamine (0.0252 mol) and N,N-diethylethanamine (0.0252 mol) in ethanol (100 ml) was stirred and refluxed for 6 hours, poured out into water and extracted with CH₂Cl₂. The organic layer was separated, dried (MgSO₄), filtered and the solvent was Procedure for compounds 400, 401, 402, 403, 404 and 405. A mixture of interm. 21 (prepared according to A11) (0.000269 mol), amantadine hydrochloride (0.000404 mol; 1.5 eq.), N'-(ethylcarbonimidoyl)-N,N-dimethyl-1,3-propanediamine hydrochloride (0.000404 mol; 1.5 equiv.), 1-hydroxy-1H-benzotriazole (0.000404 mol; 1.5 equiv.) and Et₃N (0.000269 mol) in CH₂Cl₃ (2 ml) was stirred at room temperature for 12 hours. The solvent was evaporated. The residue was purified by HPLC. The product fractions were collected and the solvent was evaporated. Yield: 0.063 g of compound 520 (46.37%).

EXAMPLE B10

Preparation of

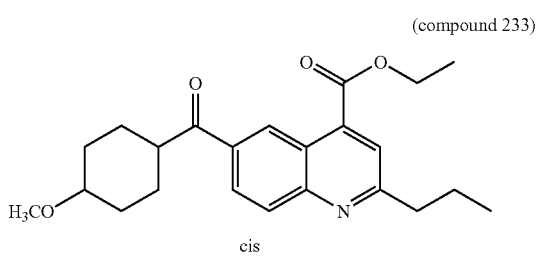

(compound 233)

cis

A mixture of intermediate 27 (0.0026 mol) and intermediate 26 (0.0026 mol) in EtOH (380 ml) and $H_2SO_4$ conc. (19 ml) was stirred and refluxed for 15 hours, the cooled to room temperature, poured out into ice water, basified with $K_2CO_3$ and extracted with EtOAc. The organic layer was separated, dried ($MgSO_4$), filtered, and the solvent was evaporated. The residue (17.9 g) was purified by column chromatography over silica gel (eluent: cyclohexane/EtOAc; 80/20; 15-35 µm). The pure fractions were collected and the solvent was evaporated. Yielding: 0.85 g of F1, 1.1 g F2 and 11.5 g of F3. F1 and F2 were crystallized separately from petroleum ether. The precipitate was filtered off and dried. Yielding: 0.34 g of compound 233.

EXAMPLE B11

Preparation of

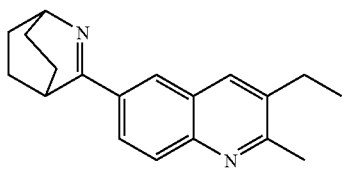

(compound 511)

A mixture of compound 22 (prepared according to B4) (0.004 mol) in HCl (3N) (20 ml) and THF (20 ml) was stirred and refluxed for 8 hours, poured out on ice, basified with $NH_4OH$ and extracted with $CH_2Cl_2$. The organic layer was separated, dried ($MgSO_4$), filtered, and the solvent was evaporated. The residue (1.2 g) was purified by column chromatography over silica gel (eluent: $CH_2Cl_2/CH_3OH/NH_4OH$; 93/7/0.5; 15-40 µm). Two fractions were collected and the solvent was evaporated. Yielding: 0.5 g F1 (41%) and 0.4 g of F2. F1 was crystallized from petroleum ether. The precipitate was filtered off and dried. Yielding: 0.17 g of compound 511 (14%).

EXAMPLE B12

Preparation of

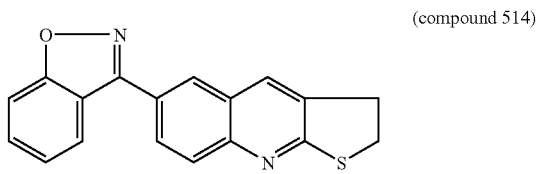

(compound 514)

A mixture of compound 524 (prepared according to B9a) (0.0018 mol) and KOH 85% (0.0094 mol) in EtOH (15 ml) was stirred and refluxed for 24 hours, poured out into $H_2O$ and extracted with $CH_2Cl_2$. The organic layer was separated, dried (MgSO4), filtered, and the solvent was evaporated. The residue was purified by column chromatography over silica gel (eluent: $CH_2Cl_2$/Cyclohexane 80/20; 15-40 µm). Two fractions were collected and the solvent was evaporated. Yielding: 0.35 g F1 (64%) and 0.17 g (SM) F1 was crystallized from diethyl ether. The precipitate was filtered off and dried. Yielding: 0.33 g of compound 514 (60%) (mp.: 185° C.).

EXAMPLE B13

Preparation of

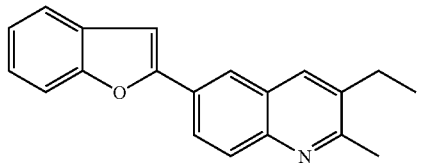

(compound 515)

A mixture of interm. 28 (0.019 mol), 2-benzofuranylboronic acid (0.028 mol), $Pd(PPh_3)_4$ (0.001 mol) and BHT (a few quantity) in dioxane (25 ml) and $Na_2CO_3$ [2] (25 ml) was stirred and refluxed for 8 hours and extracted with EtOAc. The aqueous layer was basified with $NH_4OH$ and extracted with $CH_2Cl_2$. The organic layer was separated, dried ($MgSO_4$), filtered, and the solvent was evaporated. The residue (3.6 g) was purified by column chromatography over silica gel (eluent: $CH_2Cl_2/CH_3OH$ 99/1; 15-40 µm). The pure fractions were collected and the solvent was evaporated. Yielding: 1.8 g (33%). This fraction was crystallized from 2-propanone/diethyl ether. The precipitate was filtered off and dried. Yielding: 0.39 g of compound 515 (7%) (mp.: 134° C.).

EXAMPLE B14

Preparation of

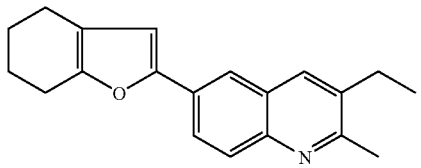

(compound 526)

Triethylsilane (0.0012 mol) was added slowly at room temperature to a solution of interm. 32 (0.004 mol) in CF$_3$COOH (5 ml) and AcOH (10 ml). NaBH$_4$ (0.0012 mol) was added portionwise under N$_2$ flow. The mixture was stirred at room temperature for 8 hours, poured out on ice, basified with K$_2$CO$_3$ and extracted with CH$_2$Cl$_2$. The organic layer was separated, dried (MgSO$_4$), filtered, and the solvent was evaporated. The residue (1.2 g) was purified by column chromatography over silica gel (eluent: CH$_2$Cl$_2$/CH$_3$OH 99/1; 15-40 μm). Two fractions were collected and the solvent was evaporated. Yielding: 0.5 g F1 (43%) and 0.4 g F2. F1 was dissolved in iPrOH. HCl/iPrOH (1 eq) were added. The precipitate was filtered off and dried; Yielding: 0.32 g of compound 526 (mp.: 248° C.).

EXAMPLE B15

Preparation of

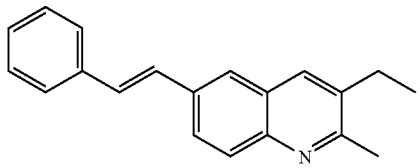

(compound 471)

A mixture of interm. 33 (0.082 mol) and 3-chloro-2-ethyl-2-butenal (0.098 mol) in AcOH (200 ml) was stirred and refluxed for 8 hours. The solvent was evaporated till dryness. The residue was dissolved in CH$_2$Cl$_2$ and washed with K$_2$CO$_3$ 10%. The organic layer was separated, dried (MgSO$_4$), filtered, and the solvent was evaporated. The residue (27 g) was purified by column chromatography over silica gel (eluent: CH$_2$Cl$_2$/EtOAc 95/5 to 92/8; 15-35 μm). Two fractions were collected and the solvent was evaporated. Yielding: 0.7 g of F1 and 5.3 g F2. F1 was crystallized from 2-propanone/diethyl ether. The precipitate was filtered off and dried. Yielding: 0.25 g of compound 471 (2%) (mp.: 140° C.).

EXAMPLE B16

Preparation of

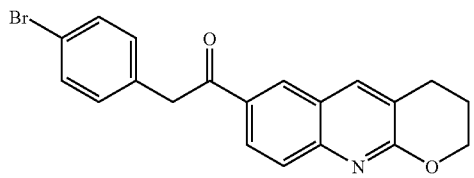

(compound 498)

nBuLi (0.0417 mol) was added dropwise at −78° C. to a solution of interm. 35 (prepared according to A17.b) (0.0379 mol) in THF (200 ml) under N$_2$ flow. The mixture was stirred for 30 minutes. A solution of 4-bromo-N-methoxy-N-methylbenzeneacetamide (0.0568 mol) in THF (100 ml) was added dropwise at −78° C. The mixture was stirred from −78° C. to 0° C., poured out into H$_2$O and extracted with EtOAc. The organic layer was separated, dried (MgSO$_4$), filtered, and the solvent was evaporated till dryness. The residue (20.9 g) was purified by column chromatography over silica gel (eluent: toluene/EtOAc 60/40 to 50/50; 15-35 μm). Two fractions were collected and the solvent was evaporated. Yielding: 4 g of fraction 1 and 4 g of fraction 2 (28%). Fraction 2 was crystallized from diethyl ether. The precipitate was filtered off and dried. Yielding: 1 g compound 528 (m.p. 195° C.).

Tables 1 to 8 list the compounds of formula (I-A) and (I-B) which were prepared according to one of the above examples.

TABLE 1

| Co. no. | Ex. no. | $R^2$ | $R^3$ | $R^4$ | $R^1$ | physical data |
|---|---|---|---|---|---|---|
| 54 | B2 | Cl | ethyl | H | 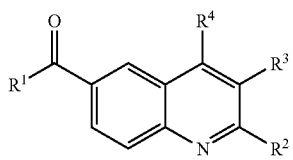 | — |

TABLE 1-continued

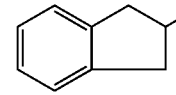

| Co. no. | Ex. no. | R² | R³ | R⁴ | R¹ | physical data |
|---|---|---|---|---|---|---|
| 3 | B3a | Cl | ethyl | H |  | mp. 145° C. |
| 55 | B3b | Cl | ethyl | H | 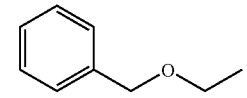 | mp. 131° C. |
| 56 | B3b | Cl | ethyl | H | 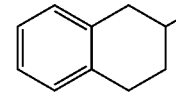 | mp. 104° C. |
| 57 | B3b | Cl | ethyl | H | phenylethyl | mp. 100° C. |
| 58 | B3b | Cl | ethyl | H | 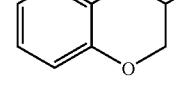 | mp. 126° C. |
| 59 | B3b | Cl | ethyl | H | 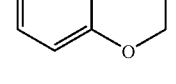 | mp. 150° C. |
| 60 | B3b | Cl | ethyl | H | 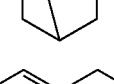 | mp. 138° C. |
| 61 | B3b | OCH₃ | ethyl | H | 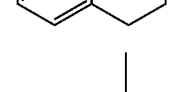 | — |
| 62 | B3b | OCH₃ | ethyl | H |  | mp. 130° C. |
| 63 | B3b | OCH₃ | ethyl | H |  | mp. 116° C. |
| 64 | B3b | Cl | ethyl | H | —(CH₂)₂—O—CH₃ | mp. 82° C. |
| 65 | B3b | OCH₃ | ethyl | H | 1-methylcyclohexyl | mp. 82° C. |
| 66 | B3b | OCH₃ | ethyl | H | 3-methoxycyclohexyl | trans; mp. 94° C. |
| 67 | B3b | OCH₃ | ethyl | H | 3-methoxycyclohexyl | cis; mp. 108° C. |
| 68 | B3b | OCH₃ | ethyl | H | 4-(methylethoxy)-cyclohexyl | (A), mp. 82° C. |
| 69 | B3b | OCH₃ | ethyl | H | 4-[C(CH₃)₃]cyclohexyl | cis; mp. 92° C. |
| 70 | B3b | OCH₃ | ethyl | H | 4-[C(CH₃)₃]cyclohexyl | trans; mp. |

TABLE 1-continued

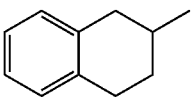

| Co. no. | Ex. no. | R² | R³ | R⁴ | R¹ | physical data |
|---|---|---|---|---|---|---|
| 71 | B3b | OCH₃ | ethyl | H | 4-methylcyclohexyl | 108° C. (B), mp. |
| 72 | B3b | OCH₃ | ethyl | H | 4-methylcyclohexyl | 92° C. (A), mp. |
| 2 | B2 | Cl | ethyl | H | CH₂—CH(CH₃)₂ | 80° C. mp. 82° C. |
| 73 | B3b | Cl | ethyl | H | —CH₂—O—C₂H₅ | mp. 82° C. |
| 48 | B2 | H | methyl | H | cyclohexyl | — |
| 74 | B4 | I | ethyl | H | 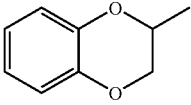 | — |
| 75 | B4 | I | ethyl | H | 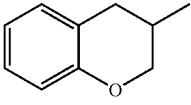 | mp. 124° C. |
| 76 | B4 | I | ethyl | H | 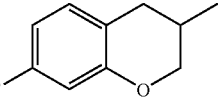 | mp. 138° C. |
| 77 | B4 | I | ethyl | H | 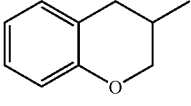 | mp. 120° C. |
| 78 | B4 | CN | ethyl | H | 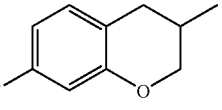 | mp. 128° C. |
| 79 | B4 | CN | ethyl | H | 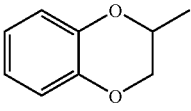 | mp. 136° C. |
| 80 | B4 | CN | ethyl | H | 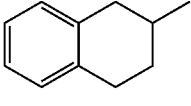 | mp. 120° C. |
| 81 | B4 | CN | ethyl | H | 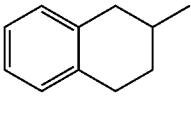 | mp. 139° C. |
| 82 | B4 | methyl | ethyl | H | 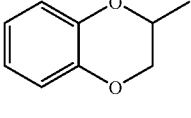 | mp. 106° C. |
| 83 | B4 | methyl | ethyl | H | | mp. 149° C. |

TABLE 1-continued

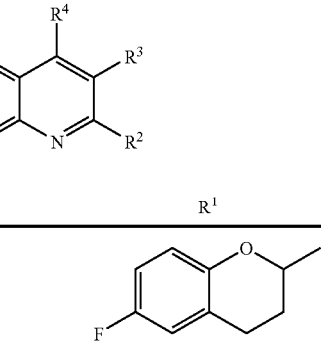

| Co. no. | Ex. no. | R² | R³ | R⁴ | R¹ | physical data |
|---|---|---|---|---|---|---|
| 84 | B4 | methyl | ethyl | H |  | mp. 118° C. |
| 85 | B4 | methyl | ethyl | H | 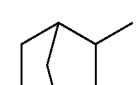 | mp. 180° C. |
| 86 | B4 | methyl | ethyl | H | phenylethyl | mp. 53° C. |
| 87 | B4 | methyl | ethyl | H | 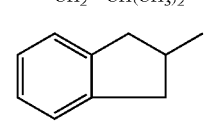 | mp. 87° C. |
| 88 | B4 | methyl | ethyl | H | —CH₂—CH(CH₃)₂ | mp. 68° C. |
| 89 | B4 | methyl | ethyl | H | 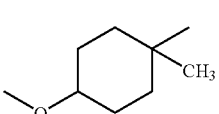 | mp. 120° C. |
| 31 | B4 | 3-thiazolyl | ethyl | H | 4-methoxycyclohexyl | cis; 113° C. |
| 90 | B3b | OCH₃ | H | H | 4-methoxycyclohexyl | trans, mp. 126° C. |
| 91 | B3b | OCH₃ | H | H | 4-methoxycyclohexyl | cis, mp. 100° C. |
| 92 | B3b | OCH₃ | H | CH₃ | 4-methoxycyclohexyl | cis; mp. 120° C. |
| 93 | B3b | OCH₃ | H | CH₃ | 4-methoxycyclohexyl | trans; mp. 111° C. |
| 94 | B3b | OCH₃ | methyl | H | 4-methoxycyclohexyl | cis, mp. 96° C. |
| 95 | B3b | OCH₃ | phenyl | H | 4-methoxycyclohexyl | cis; HCl (1:1), mp. 138° C. |
| 96 | B3b | OCH₃ | propyl | H | 4-methoxycyclohexyl | trans; mp. 118° C. |
| 97 | B3b | OCH₃ | propyl | H | 4-methoxycyclohexyl | cis; mp. 108° C. |
| 98 | B3b | OCH₃ | methyl | H | 4-methoxycyclohexyl | cis; mp. 104° C. |
| 99 | B4 | N(CH₃)₂ | ethyl | H | 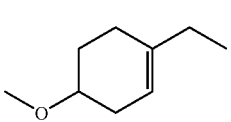 | (B); mp. 102° C. |
| 100 | B3b | Cl | ethyl | H | 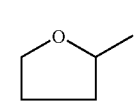 | mp. 114° C. |
| 101 | B4 | methyl | ethyl | H | 4-butoxycyclohexyl | cis; mp. 86° C. |
| 102 | B3b | Cl | ethyl | H | 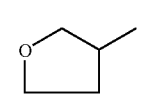 | mp. 78° C. |
| 103 | B3b | Cl | ethyl | H |  | mp. 91° C. |

TABLE 1-continued

| Co. no. | Ex. no. | R² | R³ | R⁴ | R¹ | physical data |
|---|---|---|---|---|---|---|
| 104 | B4 | N(CH₃)₂ | ethyl | H | bicyclo[2.2.1]heptyl (norbornyl) | mp. 103° C. |
| 105 | B4 | N(CH₃)₂ | ethyl | H | 2,3-dihydro-1,4-benzodioxin-2-ylmethyl | mp. 170° C. |
| 106 | B3b | Cl | ethyl | H | 4,4-dimethylcyclohexyl | mp. 137° C. |
| 107 | B3b | Cl | ethyl | H | tetrahydro-2H-pyran-4-yl | mp. 137° C. |
| 108 | B4 | methyl | ethyl | ethyl | 4-methoxycyclohexyl | cis; mp. 91° C. |
| 109 | B4 | methyl | ethyl | H | 4-ethoxycyclohexyl | trans; mp. |
| 110 | B4 | methyl | ethyl | H | 4-methoxycyclohexylmethyl | mp. 90° C. |
| 111 | B4 | methyl | ethyl | H | 4-methoxycyclohex-3-enylmethyl | mp. 94° C. |
| 112 | B4 | methyl | ethyl | H | cyclohex-3-enyl | mp. 176° C. |
| 113 | B4 | methyl | ethyl | H | 6-methoxy-1,2,3,4-tetrahydronaphthalen-2-yl | mp. 106° C. |
| 114 | B4 | propyl | H | H | 4-methoxycyclohexyl | cis; mp. 74° C. |
| 115 | B4 | methyl | ethyl | H | 4-ethoxycyclohexyl | cis; mp. 108° C. |
| 116 | B4 | methyl | ethyl | H | tetrahydro-2H-pyran-4-yl | mp. 110° C. |
| 117 | B3b | Cl | ethyl | H | 1-phenylethyl | mp. 124° C. |

TABLE 1-continued
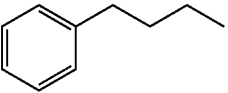
| Co. no. | Ex. no. | R² | R³ | R⁴ | R¹ | physical data |
|---|---|---|---|---|---|---|
| 118 | B3b | Cl | ethyl | H | 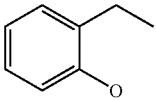 | mp. 107° C. |
| 119 | B3b | Cl | ethyl | H | 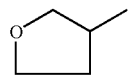 | mp. 129° C. |
| 120 | B4 | methyl | ethyl | H | 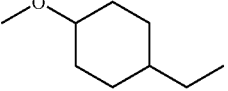 | mp. 106° C. |
| 41 | B3b | Cl | ethyl | H | 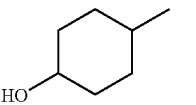 | trans; mp. 157° C. |
| 182 | B3b | methyl | ethyl | H | 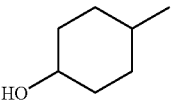 | cis; mp. 170° C. |
| 183 | B3b | methyl | ethyl | H | 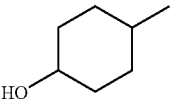 | trans; mp. 144° C. |
| 184 | B3b | methyl | ethyl | H | 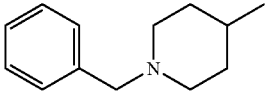 | mp. 138° C. |
| 185 | B3b | Cl | ethyl | H | 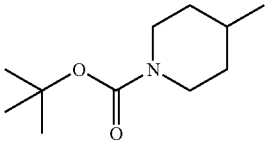 | mp. 120° C. |
| 186 | B3b | Cl | ethyl | H | 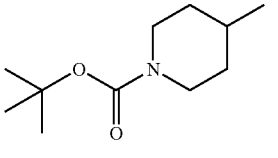 | |
| 187 | B3b | methyl | ethyl | H | | mp. 162° C. |
| 216 | B4 | C≡N | ethyl | H | 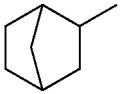 | mp.: 160° C. |

TABLE 1-continued

| Co. no. | Ex. no. | R² | R³ | R⁴ | R¹ | physical data |
|---|---|---|---|---|---|---|
| 217 | B4 | methyl | ethyl | H | 3-methylchroman-yl | .ethanedioate (1:1); mp.: 143° C. |
| 218 | B4 | I | ethyl | H | phenylpropyl | mp.: 102° C. |
| 219 | B4 | CC≡N | ethyl | H | sec-butyl (H₃C, H₃C) | mp.: 115° C. |
| 220 | B4 | Cl | ethyl | H | 4-methoxy-1-fluoro-1-methylcyclohexyl | (A); mp.: 107° C. |
| 221 | B4 | Cl | ethyl | H | 4-methoxy-1-fluoro-1-methylcyclohexyl | (B); mp.: 113° C. |
| 222 | B4 | I | ethyl | H | adamantyl-methyl | mp.: 206° C. |
| 223 | B4 | Cl | ethyl | H | 4-methylcyclohexyl | (trans); mp.: 117° C. |
| 224 | B4 | methyl | ethyl | H | 4-methoxy-1-methylcyclohexyl | (A); mp.: 103° C. |
| 225 | B2 | Cl | ethyl | H | cyclohexenyl-methyl | mp.: 94° C. |
| 226 | B3b | Cl | ethyl | H | 4-ethoxycyclohexyl-methyl | (trans); mp.: 157° C. |
| 227 | B3c | methoxy | ethyl-morpholine | H | 4-methoxycyclohexyl-methyl | mp.: 204° C. |

TABLE 1-continued
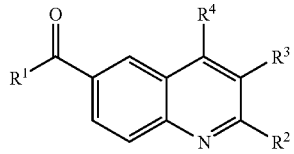
| Co. no. | Ex. no. | R² | R³ | R⁴ | R¹ | physical data |
|---|---|---|---|---|---|---|
| 228 | B4 | Cl | ethyl | H | 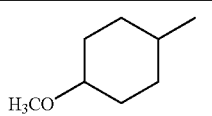 | (A); mp.: 136° C. |
| 229 | B3b | n-propyl | H | H | 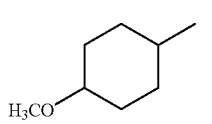 | (trans);.HCl (1:1); mp.; 150° C. |
| 230 | B3b | Cl | ethyl | H | 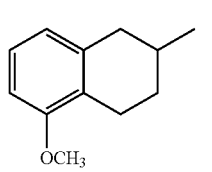 | mp.: 116° C. |
| 231 | B3b | Cl | ethyl | H | 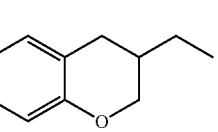 | mp.: 120° C. |
| 232 | B3b | Cl | ethyl | H | 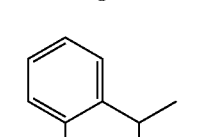 | mp.: 112° C. |
| 233 | B10 | i-propyl | H | C(=O)O—C₂H₅ | 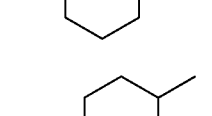 | (cis); mp.: 91° C. |
| 234 | B4 | methyl | ethyl | H | 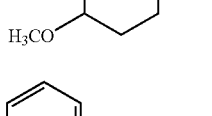 | mp.: 122° C. |
| 235 | B4 | methyl | ethyl | H | 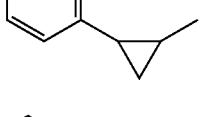 | mp.: 106° C. |
| 236 | B4 | methyl | ethyl | H | 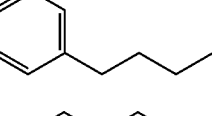 | mp.: 104° C. |
| 237 | B4 | methyl | ethyl | H | 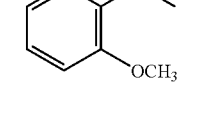 | mp.: 90° C. |

TABLE 1-continued

| Co. no. | Ex. no. | R² | R³ | R⁴ | R¹ | physical data |
|---|---|---|---|---|---|---|
| 238 | B4 | methyl | H | H | 4-methoxycyclohexyl | (cis); mp.: 80° C. |
| 239 | B3b | Cl | ethyl | H | 3-methoxycyclohexylmethyl | (trans); mp.: 126° C. |
| 240 | B3b | Cl | ethyl | H | 3-methoxycyclohexylmethyl | (cis); mp.: 128° C. |
| 241 | B4 | methyl | ethyl | H | 3-methoxycyclohexylmethyl | (A); mp.: 90° C. |
| 242 | B4 | methyl | ethyl | H | 4-methoxy-4-methylcyclohexyl | (B); mp.: 110° C. |
| 243 | B3b | Cl | ethyl | H | ethyl-dioxaspiro cyclohexyl | mp.: 134° C. |
| 244 | B3b | Cl | ethyl | H | norbornylmethyl | mp.: 127° C. |
| 245 | B4 | NHC(=O)NH₂ | ethyl | H | 4-methoxycyclohexyl | (cis); mp.: 176° C. |
| 246 | B4 | methyl | ethyl | H | 4-methylcyclohexyl | (B) |
| 247 | B3b | Cl | ethyl | H | tetrahydropyran-3-yl | mp.: 92° C. |
| 248 | B4 | methyl | ethyl | H | 4-methylcyclohexyl | (A); mp.: 80° C. |

TABLE 1-continued
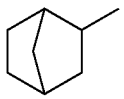
| Co. no. | Ex. no. | R² | R³ | R⁴ | R¹ | physical data |
|---|---|---|---|---|---|---|
| 249 | B3b | Cl | ethyl | H | 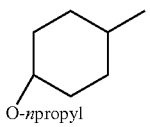 | (B); mp.: 138° C. |
| 250 | B4 | methyl | ethyl | H | 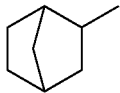 O-npropyl | (trans); mp.: 118° C. |
| 251 | B4 | methyl | ethyl | H | 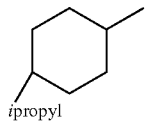 | (B);.HCl(1:1) |
| 252 | B3b | Cl | ethyl | H | 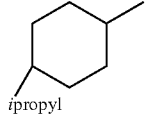 ipropyl | (A) |
| 253 | B3b | Cl | ethyl | H | 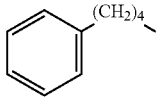 ipropyl | (B) |
| 254 | B3b | methyl | ethyl | H | 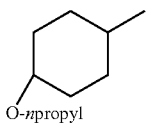 (CH₂)₄ | mp.: 74° C. |
| 255 | B4 | methyl | ethyl | H | 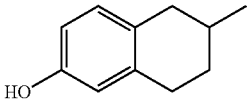 O-npropyl | (cis); mp.: 68° C. |
| 256 | B4 | methyl | ethyl | H | 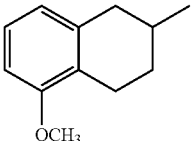 HO | mp.: 210° C. |
| 257 | B4 | methyl | ethyl | H | 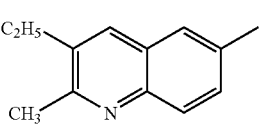 OCH₃ | mp.: 113° C. |
| 258 | B4 | methyl | ethyl | H | C₂H₅ CH₃ | mp.: 92° C. |

TABLE 1-continued
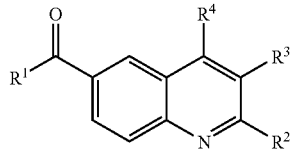
| Co. no. | Ex. no. | R² | R³ | R⁴ | R¹ | physical data |
|---|---|---|---|---|---|---|
| 259 | B3b | methyl | ethyl | H | 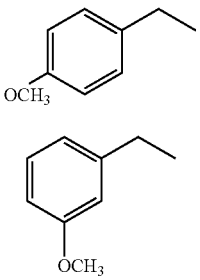 | mp.: 115° C. |
| 260 | B3b | methyl | ethyl | H | 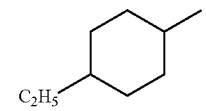 | mp.: 60° C. |
| 261 | B3b | Cl | ethyl | H | 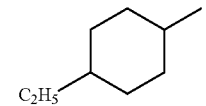 | (A); mp.: 86° C. |
| 262 | B3b | Cl | ethyl | H | 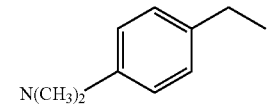 | (B); mp.: 101° C. |
| 263 | B3b | methyl | ethyl | H | 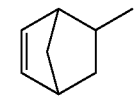 | mp.: 130° C. |
| 264 | B3b | Cl | ethyl | H | 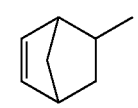 | (A); mp.: 124° C. |
| 265 | B3b | Cl | ethyl | H | 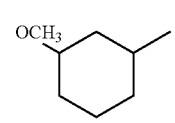 | (B); mp.: 126° C. |
| 266 | B4 | N(CH₃)₂ | ethyl | H | 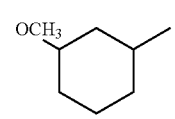 | (trans); mp.: 102° C. |
| 267 | B4 | N(CH₃)₂ | ethyl | H | 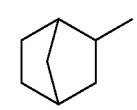 | (cis);.HCl(1:1); mp.: 170° C. |
| 268 | B4 | methyl | ethyl | H | 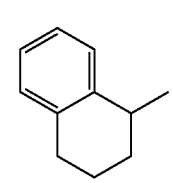 | (A);.HCl(1:1); mp.: 206° C. |
| 269 | B4 | methyl | ethyl | H | | mp.: 104° C. |

TABLE 1-continued
| Co. no. | Ex. no. | R² | R³ | R⁴ | R¹ | physical data |
|---|---|---|---|---|---|---|
| 270 | B3b | methyl | ethyl | H | 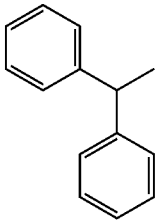 | mp.: 117° C. |
| 271 | B4 | NHC₂H₅OCH₃ | ethyl | H | 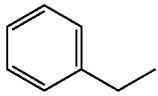 | — |
| 272 | B4 | methyl | ethyl | H | 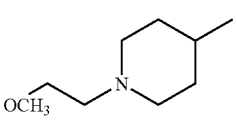 | — |
| 273 | B4 | NH₂ | ethyl | H | 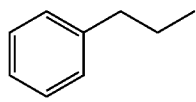 | — |
| 274 | B3b | Cl | ethyl | H | 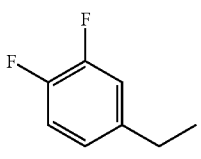 | — |
| 275 | B3b | Cl | ethyl | H | 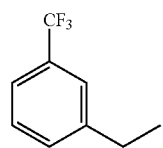 | mp.: 99° C. |
| 276 | B3b | Cl | ethyl | H | 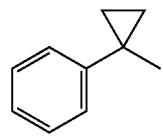 | mp.: 95° C. |
| 277 | B4 | methyl | ethyl | H | 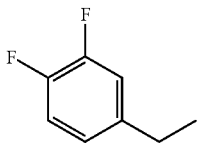 | mp.: 105° C. |
| 278 | B3b | Cl | ethyl | H | 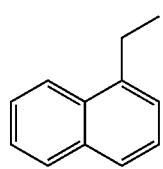 | mp.: 141° C. |

TABLE 1-continued

| Co. no. | Ex. no. | R² | R³ | R⁴ | R¹ | physical data |
|---|---|---|---|---|---|---|
| 279 | B4 | Cl | ethyl | H | norbornane with two OH and methyl | mp.: 168° C. |
| 280 | B4 | Cl | ethyl | H | norbornane with OH and methyl | — |
| 281 | B4 | Cl | ethyl | H | norbornane with OH and methyl | mp.: 140° C. |
| 282 | B4 | Cl | ethyl | H | epoxy norbornane with methyl | mp.: 169° C. |
| 283 | B4 | methyl | ethyl | H | phenyl-cyclopropyl-methyl | mp.: 96° C. |
| 284 | B3b | Cl | CH₂N(CH₃)₂ | H | benzyl/phenethyl | mp.: 115° C. |
| 285 | B4 | methyl | ethyl | H | 1-phenylethyl (CH₃) | mp.: 133° C. |
| 286 | B4 | methyl | CH₂OCH₃ | H | 4-methoxy-methylcyclohexyl | (trans); mp.: 106° C. |
| 287 | B4 | methyl | CH₂N(CH₃)₂ | H | 4-methoxy-methylcyclohexyl | (cis); mp.: 110° C. |
| 288 | B3b | Cl | n-propyl | H | phenethyl | mp.: 110° C. |
| 289 | B4 | NH₂ | ethyl | H | phenethyl | mp.: 218° C. |

TABLE 1-continued
| Co. no. | Ex. no. | R² | R³ | R⁴ | R¹ | physical data |
|---|---|---|---|---|---|---|
| 290 | B4 | methyl | n-propyl | H | 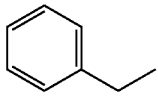 | mp.: 90° C. |
| 291 | B3b | Cl | n-propyl | H | 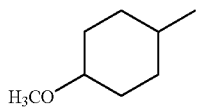 | (cis); mp.: 128° C. |
| 292 | B3b | Cl | n-propyl | H | 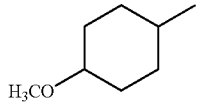 | (trans); mp.: 104° C. |
| 293 | B3b | Cl | ethyl | H |  | mp.: 106° C. |
| 294 | B4 | methyl | n-propyl | H | 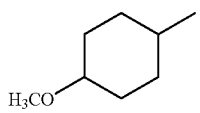 | (cis); mp.: 94° C. |
| 295 | B4 | methyl | CH₂N(CH₃)₂ | H | 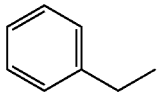 | mp. 83° C. |
| 296 | B3b | Cl | ethyl | H | 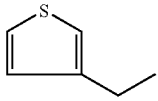 | mp.: 99° C. |
| 297 | B3b | Cl | ethyl | H | 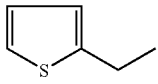 | mp.: 110° C. |
| 298 | B4 | methyl | ethyl | H | 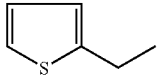 | mp.: 93° C. |
| 299 | B4 | methyl | ethyl | H | 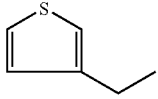 | mp.: 105° C. |
| 300 | B4 | methyl | ethyl | H | 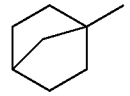 | mp.: 114° C. |
| 301 | B3b | methyl | ethyl | H | 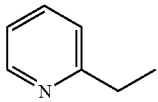 | mp.: 143° C. |

TABLE 1-continued

| Co. no. | Ex. no. | R² | R³ | R⁴ | R¹ | physical data |
|---|---|---|---|---|---|---|
| 302 | B4 | methoxy | ethyl | H | norbornyl-ethyl | mp.: 93° C. |
| 303 | B4 | methyl | ethyl | H | norbornyl-ethyl | mp.: 82° C. |
| 304 | B4 | n-butyl | ethyl | H | norbornyl-ethyl | — |
| 305 | B3b | Cl | n-propyl | H | norbornyl-ethyl | mp.: 125° C. |
| 306 | B1 | methyl | C(=O)OC₂H₅ | H | phenyl-ethyl | mp.: 136° C. |
| 307 | B4 | methyl | n-propyl | H | norbornyl-ethyl | mp.: 81° C. |
| 308 | B4 | methoxy | n-propyl | H | norbornyl-ethyl | mp.: 80° C. |
| 309 | B4 | I | n-propyl | H | phenyl-ethyl | mp.: 120° C. |
| 310 | B3d | methyl | ethyl | H | 2-methyl-3-phenyl-thiophene | .HCl(1:1); mp.: 129° C. |
| 311 | B3b | Cl | H | H | phenyl-ethyl | mp.: 160° C. |
| 312 | B3b | Cl | H | H | 4-methoxy-cyclohexyl (H₃CO) | (trans); mp.: 145° C. |

TABLE 1-continued

| Co. no. | Ex. no. | R² | R³ | R⁴ | R¹ | physical data |
|---|---|---|---|---|---|---|
| 313 | B3b | Cl | H | H | norbornyl-ethyl | mp.: 103° C. |
| 314 | B4 | n-propyl | n-propyl | H | norbornyl-ethyl | .HCl(1:1); mp.: 150° C. |
| 315 | B4 | n-propyl | ethyl | H | norbornyl-ethyl | .HCl(1:1) |
| 316 | B4 | n-propyl | H | H | tolyl | .HCl(1:1); mp.: 140° C. |
| 317 | B3b | Cl | H | H | thiophenyl-ethyl | mp.: 168° C. |
| 318 | B4 | methyl | n-propyl | H | methyl-norbornyl | .HCl(1:1); mp.: 200° C. |
| 509 | B3b | Cl | ethyl | H | methyl-dihydropyranyl | — |
| 510 | B4 | methyl | ethyl | H | methyl-dihydropyranyl | .H₂O(1:1) |
| 513 | B4 | methyl | ethyl | H | methoxy-methyl-dihydropyranyl | — |
| 516 | B4 | Cl | ethyl | H | dimethyl-cyclohexyl | mp.: 120° C. |
| 517 | B4 | I | ethyl | H | $CH_2CH(CH_3)_2$ | — |
| 518 | B4 | Cl | ethyl | H | methyl-adamantyl | — |

TABLE 1-continued

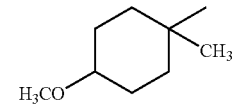

| Co. no. | Ex. no. | R² | R³ | R⁴ | R¹ | physical data |
|---|---|---|---|---|---|---|
| 519 | B4 | Cl | ethyl | H |  | (A + B) |
| 521 | B4 | I | ethyl | H | 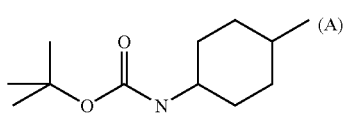 | — |
| 522 | B4 | methyl | ethyl | H | 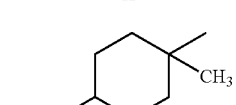 | (A) |
| 1 | B4 | methyl | ethyl | H | 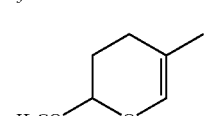 | (A) |
| 525 | B4 | Cl | ethyl | H | 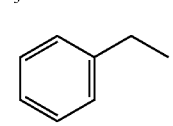 | |
| 527 | B4 | F | ethyl | H | | mp.: 116° C. |

TABLE 2

| Co. no. | Ex. no. | R² | X | physical data |
|---|---|---|---|---|
| 5 | B3b | Cl | O | trans; mp. 120° C. |
| 121 | B3b | 1-piperidinyl | O | cis; HCl (1:1) |
| 122 | B3b | 1-piperidinyl | O | trans; HCl (1:1); mp. 128° C. |
| 123 | B3b | 4-thiomorpholinyl | O | cis; mp. 105° C. |
| 124 | B3b | 4-thiomorpholinyl | O | trans; mp. 115° C. |
| 125 | B3b | 4-morpholinyl | O | trans; mp. 118° C. |
| 126 | B3b | 4-morpholinyl | O | cis; mp. 118° C. |
| 127 | B3b | —N(CH₃)₂ | O | trans; mp. 96° C. |
| 128 | B3b | —N(CH₃)₂ | O | cis; mp. 114° C. |
| 4 | B3b | Cl | O | cis; mp. 123° C. |
| 8 | B3c | OCH₃ | O | trans, mp. 68° C. |
| 7 | B3c | OCH₃ | O | cis; mp. 116° C. |
| 6 | B4 | acetyl | O | trans; mp. 108° C. |
| 129 | B4 | acetyl | O | cis; mp. 106° C. |
| 11 | B4 | NH—(CH₂)₂—OCH₃ | O | trans; mp. 107° C. |
| 10 | B4 | NH—(CH₂)₂—OCH₃ | O | cis; mp. 115° C. |

TABLE 2-continued

[Structure: 4-methoxycyclohexyl group connected via C(=X) to a quinoline bearing CH₂—CH₃ at 3-position and R² at 2-position]

| Co. no. | Ex. no. | R² | X | physical data |
|---|---|---|---|---|
| 12 | B4 | NH—(CH₂)₂—SCH₃ | O | cis; mp. 120° C. |
| 13 | B4 | NH—(CH₂)₂—SCH₃ | O | trans; mp. 125° C. |
| 14 | B4 | —C≡C—Si(CH₃)₃ | O | cis; mp. 114° C. |
| 16 | B4 | —C≡C—Si(CH₃)₃ | O | trans; mp. 108° C. |
| 15 | B4 | —C≡CH | O | cis; mp. 132-133° C. |
| 17 | B4 | —C≡CH | O | trans; mp. 128° C. |
| 18 | B4 | —C≡C—CH₂OH | O | cis; mp. 113° C. |
| 130 | B4 | —C≡C—CH₂OH | O | trans; mp. 108° C. |
| 19 | B4 | F | O | cis; mp. 92-99° C. |
| 20 | B4 | F | O | trans; mp. 114° C. |
| 21 | B4 | I | O | cis; mp. 110° C. |
| 22 | B4 | CN | O | cis; mp. 137-138° C. |
| 26 | B4 | H | O | trans |
| 23 | B4 | —C(=O)—OCH₃ | O | cis; mp. 91° C. |
| 24 | B4 | —C(=O)—OCH₃ | O | trans; mp. 99° C. |
| 25 | B4 | H | O | cis; mp. 88° C. |
| 27 | B4 | methyl | O | cis; mp. 110-112° C. |
| 131 | B4 | methyl | O | trans; mp. 25° C. |
| 28 | B4 | ethenyl | O | cis; mp. 108° C. |
| 132 | B4 | ethenyl | O | trans; mp. 103° C. |
| 29 | B4 | phenyl | O | trans; mp. 112° C. |
| 30 | B4 | 2-thienyl | O | cis; 142° C. |
| 133 | B4 | 2-thiazolyl | O | cis; 108° C. |
| 134 | B4 | 2-furanyl | O | cis; mp. 105° C. |
| 51 | B8a | OCH₃ | N—OH | [1α(A),4α]; mp. 133° C. |
| 52 | B8a | OCH₃ | N—OH | [1α(B),4α]; mp. 142° C. |
| 53 | B8b | OCH₃ | NNH₂ | [1α(Z),4α]; mp. 110° C. |
| 135 | B4 | NH₂ | O | cis; mp. 203° C. |
| 136 | B4 | NH₂ | O | trans; mp. 202° C. |
| 137 | B4 | —C(=O)—OCH(CH₃)₂ | O | cis; mp. 105° C. |
| 138 | B4 | —C(=O)—OCH(CH₃)₂ | O | trans; mp. 88° C. |
| 38 | B4 | SCH₃ | O | cis; mp. 124° C. |
| 39 | B4 | SCH₃ | O | trans; mp. 116° C. |
| 32 | B4 | [N-acetyl glycine methyl ester substituent: CH₃—C(=O)—NH—CH₂—C(=O)—OCH₃] | O | cis; mp. 130° C. |
| 139 | B4 | ethyl | O | cis; mp. 180° C. |
| 188 | B4 | NH₂ | O | cis + trans |
| 189 | B4 | [N-methyl-4-methoxybenzamide substituent: —N(CH₃)—C(=O)—C₆H₄—OCH₃] | O | cis; mp. 154° C. |
| 190 | B4 | [N-methyl-4-methoxybenzamide substituent: —N(CH₃)—C(=O)—C₆H₄—OCH₃] | O | trans; mp. 156° C. |
| 191 | B4 | [N-methyl-2-oxo-1,2-dihydropyridine-4-carboxamide substituent] | O | cis; mp. >260° C. |

TABLE 2-continued

| Co. no. | Ex. no. | R² | X | physical data |
|---|---|---|---|---|
| 192 | B4 | (N-methylcarboxamide linked to 6-oxo-1,6-dihydropyridin-3-yl) | O | .H2O(1:1); trans; mp. 248° C. |
| 193 | B4 | (N-methylcarboxamide linked to 1-acetylpiperidin-4-yl) | O | cis; mp. 224° C. |
| 194 | B4 | (N-methylcarboxamide linked to 1-acetylpiperidin-4-yl) | O | trans; mp. 234° C. |
| 195 | B4 | N-methyl-2-ethoxyacetamide | O | cis; mp. 108° C. |
| 196 | B4 | N-methyl-2-ethoxyacetamide | O | trans; mp. 127° C. |
| 197 | B4 | N-methyl-2-(benzylthio)acetamide | O | cis; mp. 150° C. |
| 198 | B4 | N-methyl-2-(benzylthio)acetamide | O | trans; mp. 90° C. |
| 199 | B4 | N-methyladamantane-1-carboxamide | O | LC/MS [M + H]⁺; 475.4 |
| 200 | B4 | N-methyl-2-(pyridin-4-ylthio)acetamide | O | LC/MS [M + H]⁺; 464.3 |
| 201 | B4 | N-methyl-2-(3-phenoxyphenyl)acetamide | O | LC/MS [M + H]⁺; 523.3 |

TABLE 2-continued

Structure: 4-methoxycyclohexyl-C(=X)- attached to quinoline at 6-position; quinoline has 3-CH₂-CH₃ and 2-R²

| Co. no. | Ex. no. | R² | X | physical data |
|---|---|---|---|---|
| 202 | B4 | -NH-C(=O)-CH₂CH₂CH₂-(2-thienyl), N-methyl | O | LC/MS [M + H]⁺; 465.3 |
| 203 | B4 | -NH-C(=O)-CH₂-(4-ethoxyphenyl), N-methyl | O | LC/MS [M + H]⁺; 475.4 |
| 204 | B4 | -NH-C(=O)-CH₂-S-(pyrimidin-2-yl), N-methyl | O | LC/MS [M + H]⁺; 465.3 |
| 205 | B4 | -NH-C(=O)-CH₂-phenyl, N-methyl | O | |
| 319 | B4 | -CH₂-phenyl | O | (cis);.ethanedioate(1:1); mp.: 160° C. |
| 320 | B4 | -C≡C-phenyl | O | (cis); mp.: 150° C. |
| 321 | B4 | methoxy | CH₂ | (cis);.HCl(1:1); mp.: 118° C. |
| 322 | B4 | n-butyl | O | (cis);.HCl(1:1); mp.: 158° C. |
| 323 | B4 | -NH-C(=O)-(4-methoxyphenyl), N-methyl | O | — |
| 324 | B4 | -NH-C(=O)-CH=CH-phenyl, N-methyl | O | — |
| 325 | B4 | -NH-C(=O)-(1-methylindol-2-yl), N-methyl | O | — |

TABLE 2-continued
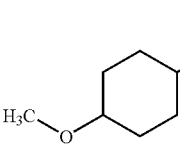
| Co. no. | Ex. no. | R² | X | physical data |
|---|---|---|---|---|
| 326 | B4 | 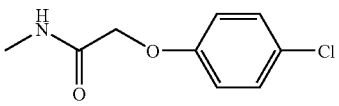 | O | — |
| 327 | B4 | 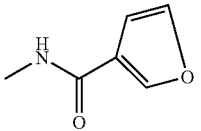 | O | — |
| 328 | B4 | 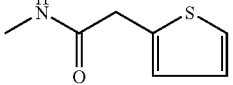 | O | — |
| 329 | B4 | 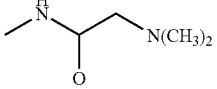 | O | — |
| 330 | B4 | 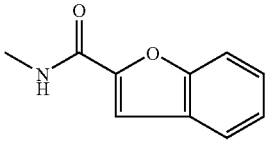 | O | — |
| 331 | B4 | 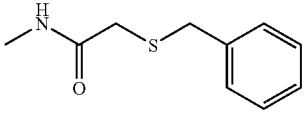 | O | — |
| 332 | B4 | 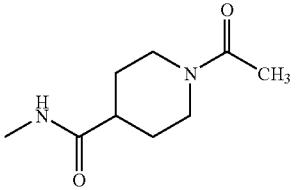 | O | — |
| 333 | B4 | 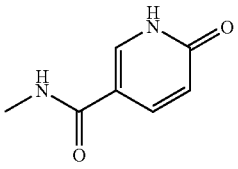 | O | — |
| 334 | B4 |  | O | — |

TABLE 2-continued
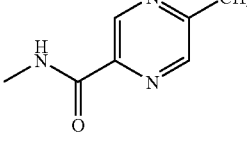
| Co. no. | Ex. no. | R² | X | physical data |
|---|---|---|---|---|
| 335 | B4 | 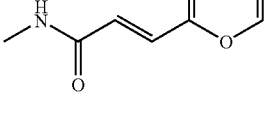 | O | — |
| 336 | B4 | 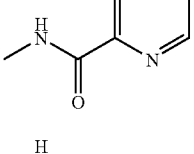 | O | — |
| 337 | B4 | 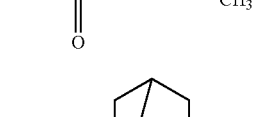 | O | — |
| 338 | B4 | 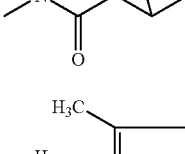 | O | — |
| 339 | B4 | 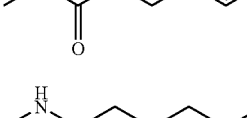 | O | — |
| 340 | B4 | 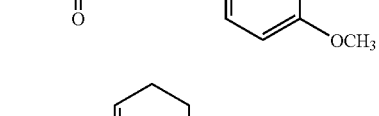 | O | — |
| 341 | B4 | 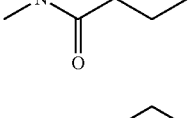 | O | — |
| 342 | B4 | 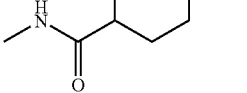 | O | — |
| 343 | B4 | | O | — |

TABLE 2-continued

| Co. no. | Ex. no. | R² | X | physical data |
|---|---|---|---|---|
| 344 | B4 | (N-methyl cyclohexanecarboxamide) | O | — |
| 345 | B4 | (N-methyl pentanamide) | O | — |
| 346 | B4 | (N-methyl 4-cyclohexylbutanamide) | O | — |
| 347 | B4 | (N-methyl 3-(3-trifluoromethylphenyl)acrylamide) | O | — |
| 348 | B4 | CH₂OPC(=O)CH₃ | O | (cis); mp.: 74° C. |
| 349 | B4 | (ethyl N-acetylglycinate) | O | — |
| 350 | B4 | (N-(3-ethoxypropyl)acetamide) | O | — |
| 351 | B4 | (ethyl N-acetyl-N-methylglycinate) | O | — |
| 352 | B4 | (N-(pyridin-2-ylmethyl)acetamide) | O | — |
| 353 | B4 | (N,N-dimethylpropylamine) | O | (A);.HCl(1:2).H2O(1:1); mp.: 166° C. |

TABLE 2-continued
| Co. no. | Ex. no. | R² | X | physical data |
|---|---|---|---|---|
| 354 | B4 |  | O | (cis) |
| 355 | B4 |  | O | — |
| 356 | B4 |  | O | — |
| 357 | B4 |  | O | — |
| 358 | B4 |  | O | — |
| 359 | B4 |  | O | — |
| 360 | B4 |  | O | — |
| 361 | B4 |  | O | — |
| 362 | B4 |  | O | — |
| 363 | B4 | | O | — |

TABLE 2-continued
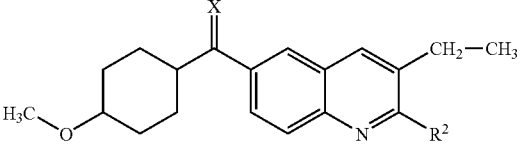
| Co. no. | Ex. no. | R² | X | physical data |
|---|---|---|---|---|
| 364 | B4 | 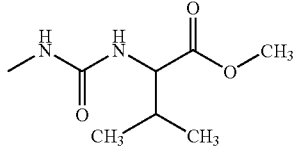 | O | — |
| 365 | B4 | 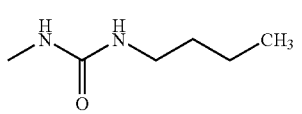 | O | — |
| 366 | B4 | 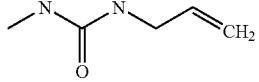 | O | — |
| 367 | B4 | 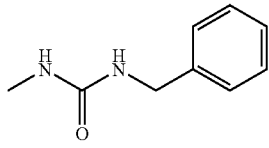 | O | — |
| 368 | B4 | 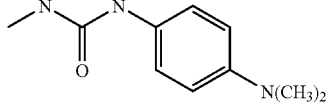 | O | — |
| 369 | B4 | 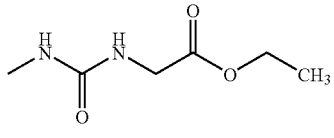 | O | — |
| 370 | B4 | 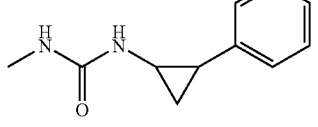 | O | — |
| 371 | B4 | 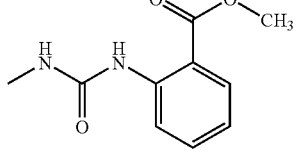 | O | — |
| 372 | B4 | | O | — |

TABLE 2-continued

[Structure: 6-substituted quinoline with CH2-CH3 at 3-position, R2 at 2-position, connected via C(=X) to a 4-methoxycyclohexyl group]

| Co. no. | Ex. no. | R² | X | physical data |
|---|---|---|---|---|
| 373 | B4 | [N-methyl-N'-(2-methylthiophenyl)urea] | O | — |
| 374 | B4 | [N-methyl-N'-(2-ethoxycarbonylethyl)urea] | O | — |
| 375 | B4 | [N-methyl-4-chlorobenzenesulfonamide] | O | — |
| 376 | B4 | [N-methyl-benzylsulfonamide] | O | — |
| 377 | B4 | [N-methyl-trifluoroethylsulfonamide] | O | — |
| 378 | B4 | [N-methyl-ethylsulfonamide] | O | — |
| 379 | B4 | [N-methyl-naphthalene-2-sulfonamide] | O | — |
| 380 | B4 | [N-methyl-3,5-dimethylisoxazole-4-sulfonamide] | O | — |
| 381 | B4 | [N-methyl-4-acetylbenzenesulfonamide] | O | — |

TABLE 2-continued

[Structure: cyclohexane with H3CO- substituent connected via C(=X) to quinoline with CH2-CH3 at 3-position and R² at 2-position]

| Co. no. | Ex. no. | R² | X | physical data |
|---|---|---|---|---|
| 382 | B4 | [N-methyl-N'H-sulfonamide-p-tolyl] | O | — |
| 383 | B4 | [N-methyl amide-(CH2)3-3,4-dimethoxyphenyl] | O | (cis); mp.: 148° C. |
| 384 | B4 | [N-methyl amide-(CH2)3-3,4-dimethoxyphenyl] | O | (trans); mp.: 141° C. |
| 385 | B4 | [N-methyl amide-(CH2)3-cyclohexyl] | O | mp.: 130° C. |
| 386 | B4 | [N-methyl amide-CH2CH2-S-CH3] | O | (cis); mp.: 140° C. |
| 387 | B4 | [N-methyl amide-tetrahydrofuran-2-yl] | O | (trans); mp.: 155° C. |

TABLE 3

[Structure: quinoline with R¹-C(=O)- at 6-position, CH2-CH3 at 3-position, =Y at 2-position, N-H]

| Co. no. | Ex. no. | Y | R¹ | physical data |
|---|---|---|---|---|
| 140 | B4 | O | [norbornyl-methyl] | mp. 220° C. |

TABLE 3-continued

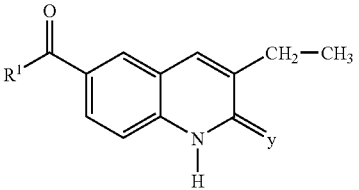

| Co. no. | Ex. no. | Y. | R¹ | physical data |
|---|---|---|---|---|
| 141 | B4 | O | 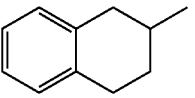 | mp. 213° C. |
| 142 | B4 | O | 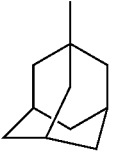 | mp. 148° C. |
| 143 | B4 | O | 1-methylcyclohexyl | mp. 195-210° C. |
| 144 | B4 | O | 3-methoxycyclohexyl | cis; mp. 156° C. |
| 145 | B4 | O | 3-methoxycyclohexyl | trans; mp. 156-163° C. |
| 146 | B4 | O | 4-(dimethylethyl)cyclohexyl | mp. 230° C. |
| 147 | B4 | O | 4-(methylethoxy)cyclohexyl | mp. 186° C. |
| 148 | B4 | O | 4-methylcyclohexyl | trans; mp. 214° C. |
| 36 | B4 | S | 4-methoxycyclohexyl | cis; mp. 224° C. |
| 37 | B4 | S | 4-methoxycyclohexyl | trans; mp. 220° C. |
| 149 | B4 | O | 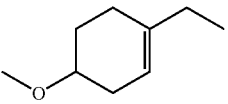 | mp. 188° C. |
| 40 | B4 | O | 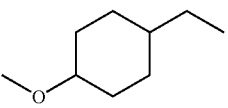 | mp. 192° C. |
| 150 | B4 | O | 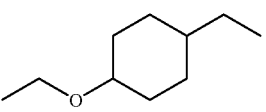 | cis; mp. 226° C. |
| 151 | B4 | O | 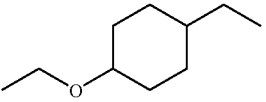 | trans; mp. 226° C. |
| 152 | B4 | O | 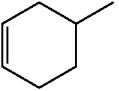 | mp. 213° C. |
| 153 | B4 | O | 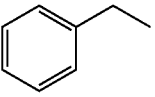 | mp. 200° C. |
| 154 | B4 | O | 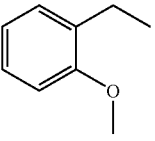 | mp. 210° C. |
| 155 | B4 | O | 4,4-dimethylcyclohexyl | mp. 242° C. |

TABLE 3-continued
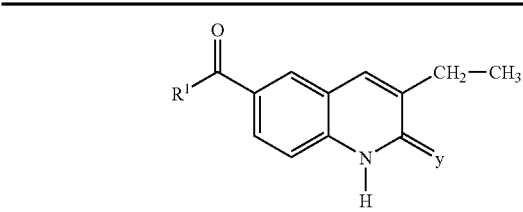
| Co. no. | Ex. no. | Y. | R¹ | physical data |
|---|---|---|---|---|
| 388 | B4 | O | CH₂CH(CH₃)₂ | mp. 189° C. |
| 389 | B4 | O | 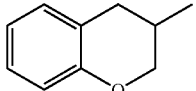 | mp. 228° C. |
| 390 | B4 | O | 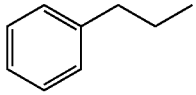 | mp. 197° C. |
| 391 | B4 | O | 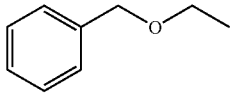 | mp. 145° C. |
| 392 | B4 | O | 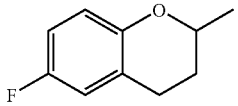 | mp. 192° C. |
| 393 | B4 | O | 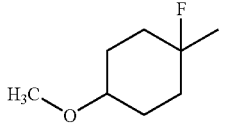 | (B); mp.: 224° C. |
| 394 | B4 | O | 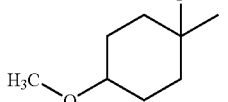 | (A); mp.: 201° C. |
| 395 | B4 | O | 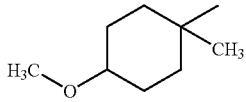 | (A); mp.: 207° C. |
| 396 | B4 | O | 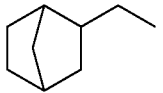 | mp.: 212° C. |
| 397 | B4 | O | 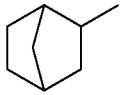 | (B); mp.: 238° C. |
| 398 | B4 | O |  | mp.: 234° C. |

TABLE 3-continued

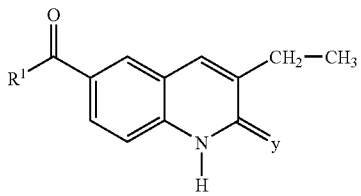

| Co. no. | Ex. no. | Y. | R¹ | physical data |
|---|---|---|---|---|
| 399 | B4 | O | (structure: 4-ethoxycyclohexyl-methyl) | (cis); mp.: 192° C. |

TABLE 4

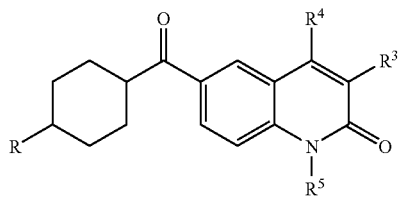

| Co. no. | Ex. no. | R³ | R⁴ | R⁵ | R | physical data |
|---|---|---|---|---|---|---|
| 156 | B4 | ethyl | H | H | OCH₃ | trans; mp. 252° C. |
| 157 | B4 | H | H | H | OCH₃ | (cis + trans); mp. 244° C. |
| 158 | B4 | H | methyl | H | OCH₃ | cis; mp. >260° C. |
| 159 | B4 | methyl | H | H | OCH₃ | cis; mp. 254° C. |
| 160 | B4 | methyl | H | H | OCH₃ | trans; mp. >260° C. |
| 161 | B4 | propyl | H | H | OCH₃ | mp. 208° C. |
| 162 | B4 | propyl | H | H | OCH₃ | trans; mp. 232° C. |
| 9 | B4 | ethyl | H | H | OCH₃ | cis; mp. 224-226° C. |
| 43 | 5 | ethyl | H | CH₃ | OCH₃ | trans; mp. 116° C. |
| 42 | 5 | ethyl | H | CH₃ | OCH₃ | cis; mp. 125° C. |
| 44 | 6 | ethyl | H | CH₂—COOC₂H₅ | OCH₃ | 152° C. |
| 45 | B4 | ethyl | H | CH₂—COOC₂H₅ | OCH₃ | trans; mp. 147° C. |
| 46 | B4 | ethyl | H | benzyl | OCH₃ | cis; mp. 137° C. |
| 47 | B4 | ethyl | H | benzyl | OCH₃ | trans; mp. 130° C. |
| 50 | 7 | methyl | H | H | H | mp. 256.1° C. |
| 163 | B4 | ethyl | ethyl | H | OCH₃ | cis; mp. 221° C. |
| 164 | B4 | ethyl | ethyl | H | OCH₃ | cis; mp. 221° C. |
| 165 | B4 | ethyl | ethyl | H | OCH₃ | trans; mp. 215° C. |
| 166 | B4 | ethyl | H | —CH(CH₃)C(O)NH-CH₂CH₂-OCH₃ | OCH₃ | LC/MS[M + H]⁺; 429.4 |
| 167 | B4 | ethyl | H | —CH(CH₃)C(O)NH-CH₂-(2-furyl) | OCH₃ | LC/MS[M + H]⁺; 451.3 |
| 168 | B4 | H | H | H | OCH₃ | cis; mp. 106° C. |
| 169 | B4 | ethyl | H | —CH(CH₃)C(O)NH-CH₂-C≡CH | OCH₃ | LC/MS[M + H]⁺; 409.3 |

TABLE 4-continued

| Co. no. | Ex. no. | R³ | R⁴ | R⁵ | R | physical data |
|---|---|---|---|---|---|---|
| 400 | B9 | ethyl | H | -CH₂C(=O)NH-CH₂-C(=O)-O-ethyl | OCH₃ | — |
| 401 | B9 | ethyl | H | -CH₂C(=O)NH-(CH₂)₃-(2-oxopyrrolidin-1-yl) | OCH₃ | — |
| 402 | B9 | ethyl | H | -CH₂C(=O)NH-(1-benzylpiperidin-4-yl) | OCH₃ | — |
| 403 | B9 | ethyl | H | -CH₂C(=O)NH-CH₂CH₂-S-benzyl | OCH₃ | — |
| 404 | B9 | ethyl | H | -CH₂C(=O)NH-CH₂CH₂-(pyridin-2-yl) | OCH₃ | — |
| 405 | B9 | ethyl | H | -CH₂C(=O)NH-CH₂CH₂-(1-methyl-1H-pyrrol-2-yl) | OCH₃ | — |
| 406 | B4 | ethyl | H | -CH₂C(=O)NH-cyclohexyl | OCH₃ | — |
| 407 | B4 | ethyl | H | -CH₂C(=O)NH-(2-oxotetrahydrothiophen-3-yl) | OCH₃ | — |
| 408 | B4 | ethyl | H | -CH₂C(=O)NH-cyclopropyl | OCH₃ | — |

TABLE 4-continued

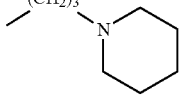

| Co. no. | Ex. no. | R³ | R⁴ | R⁵ | R | physical data |
|---|---|---|---|---|---|---|
| 409 | B3b | 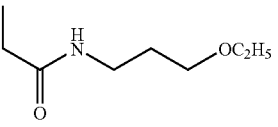 | H | H | OCH₃ | mp.: 168° C. |
| 410 | B4 | CH₂OCH₃ | H | H | OCH₃ | mp.: 194° C. |
| 508 | B4 | ethyl | H | 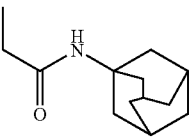 | OCH₃ | — |
| 520 | B9 | ethyl | H | 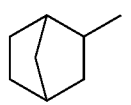 | OCH₃ | — |

TABLE 5

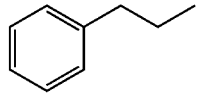

| Co. no. | Ex. no. | R⁴ | R¹ | X | physical data |
|---|---|---|---|---|---|
| 33 | B4 | H | methoxycyclohexyl | CH | cis; mp. 224° C. |
| 34 | B4 | H | methoxycyclohexyl | CH | trans; mp. 185° C. |
| 35 | B4 | H | methoxycyclohexyl | N | cis; mp. 160-172° C. |
| 170 | B4 | H | methoxycyclohexyl | N | trans; mp. 146° C. |
| 171 | B4 | H | 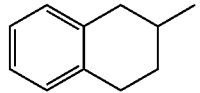 | N | (B); mp. 165° C. |
| 172 | B4 | H | methylcyclohexyl | N | cis + trans; mp. 143° C. |
| 173 | B4 | ethyl | methoxycyclohexyl | N | cis; mp.: 126° C. |
| 411 | B4 | H |  | N | mp.: 109° C. |
| 412 | B4 | H |  | N | mp.: 180° C. |

TABLE 5-continued
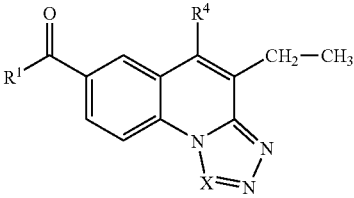
| Co. no. | Ex. no. | R⁴ | R¹ | X | physical data |
|---|---|---|---|---|---|
| 413 | B4 | H | 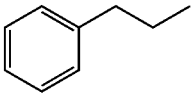 | N | (A) |
| 414 | B4 | H | 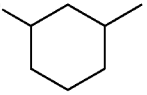 | N | mp.: 156° C. |
TABLE 6
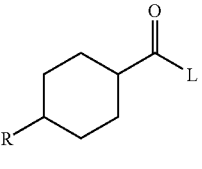
| Co. no. | Ex. no. | R | L | physical data |
|---|---|---|---|---|
| 49 | B7 | H | 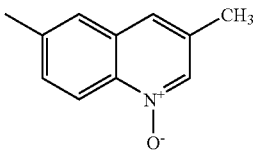 | — |
| 174 | B3b | OCH₃ | 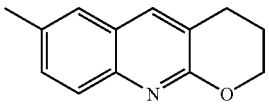 | cis; mp. 115° C. |
| 175 | B3b | OCH₃ | 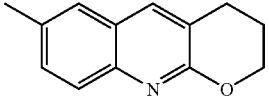 | trans; mp. 141° C. |
| 176 | B3b | OCH₃ | 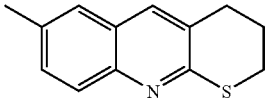 | cis; mp. 149° C. |
| 177 | B3b | OCH₃ | 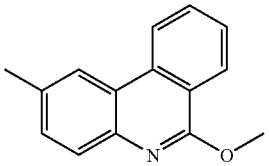 | mp. 126° C. |
| 178 | B3b | OCH₃ | 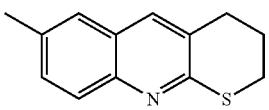 | trans; mp. 160° C. |

TABLE 6-continued
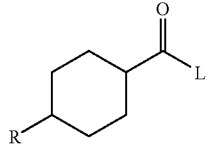
| Co. no. | Ex. no. | R | L | physical data |
|---|---|---|---|---|
| 179 | B3b | OCH$_3$ | 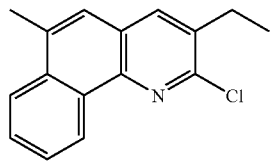 | cis; mp. 119° C. |
| 180 | B3b | OCH$_3$ | 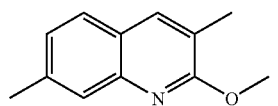 | trans; mp. 124° C. |
| 181 | B3b | OCH$_3$ | 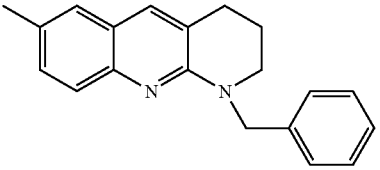 | trans; mp. 92° C. |
| 206 | B3b | OCH$_3$ | 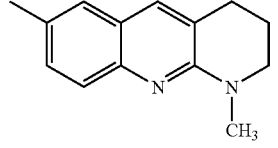 | cis; m.p. 144° C. |
| 207 | B3b | OCH$_3$ | 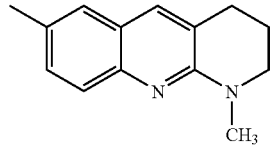 | trans; m.p. 125° C. |
| 208 | B3b | OCH$_3$ | 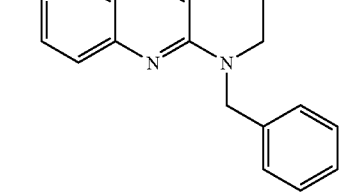 | cis; m.p. 127° C. |
| 209 | B3b | OCH$_3$ | 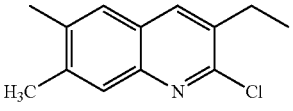 | cis; m.p. 101° C. |
| 210 | B3b | OCH$_3$ | | cis; m.p. 104° C. |

TABLE 6-continued
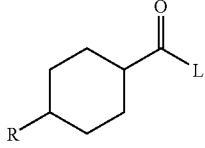
| Co. no. | Ex. no. | R | L | physical data |
|---|---|---|---|---|
| 211 | B3b | OCH₃ | 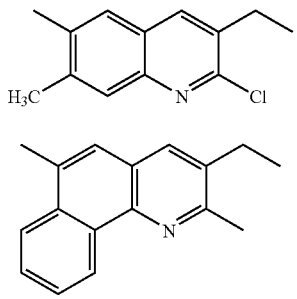 | trans; m.p. 134° C. |
| 212 | B4 | OCH₃ | 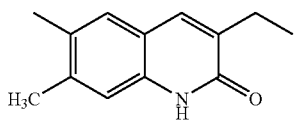 | cis; m.p. 141° C. |
| 213 | B4 | OCH₃ | 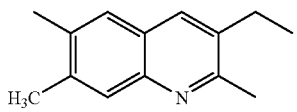 | trans; m.p. 215° C. |
| 214 | B4 | OCH₃ | 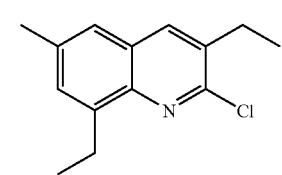 | cis; m.p. 139° C. |
| 215 | B3b | OCH₃ | 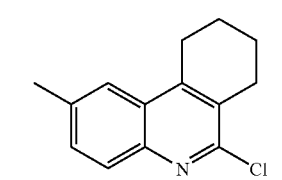 | trans |
| 415 | B3b | OCH₃ | 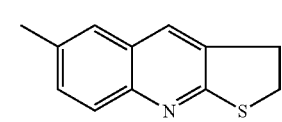 | (cis); mp.: 136° C. |
| 416 | B3b | OCH₃ | 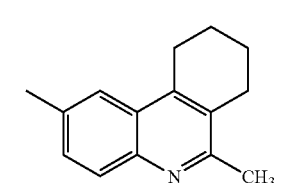 | (cis) |
| 417 | B4 | OCH₃ | 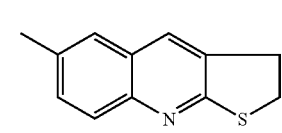 | (cis); mp.: 149° C. |
| 418 | B3b | OCH₃ | | (trans); mp: 132° C. |

TABLE 6-continued
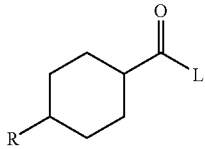
| Co. no. | Ex. no. | R | L | physical data |
|---|---|---|---|---|
| 419 | B4 | OCH₃ | 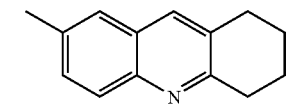 | (cis); mp.: 217° C. |
| 420 | B3b | OCH₃ | 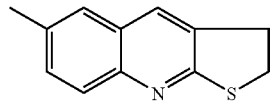 | (cis); HCl(1:1); mp.: 200° C. |
| 421 | B4 | OH | 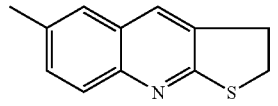 | (cis); mp.: 215° C. |
| 422 | B4 | OH | 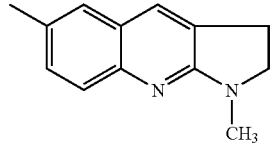 | (trans); mp.: 178° C. |
| 423 | B3b | OCH₃ | 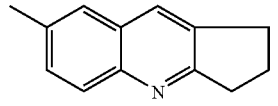 | mp.: 160° C. |
| 424 | B3b | OCH₃ | 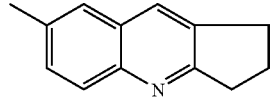 | (cis); mp.: 106° C. |
| 425 | B3b | OCH₃ | 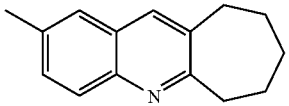 | (trans); mp.: 120° C. |
| 426 | B3b | OCH₃ | 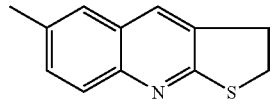 | (cis); mp.: 121° C. |
| 427 | B3b | H | 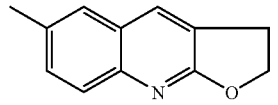 | mp.: 156° C. |
| 428 | B3b | OCH₃ | 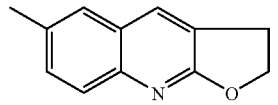 | (cis); mp.: 156° C. |
| 429 | B3b | OCH₃ |  | (trans); mp.: 197° C. |

TABLE 6-continued
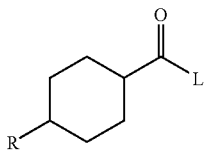
| Co. no. | Ex. no. | R | L | physical data |
|---|---|---|---|---|
| 430 | B3b | CH₃ | 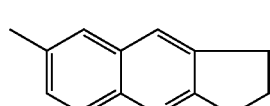 | (B) |
| 431 | B3b | CH₃ | 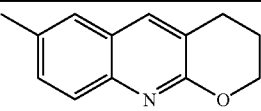 | (A) |
TABLE 7
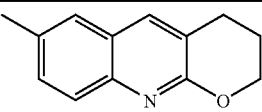
| Co. no. | Ex. no. | R¹ | L | physical data |
|---|---|---|---|---|
| 432 | B16 |  | 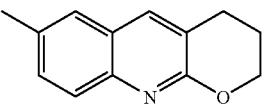 | mp.: 128° C. |
| 433 | B4 | 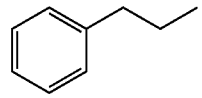 | 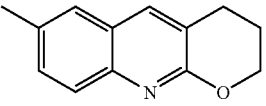 | mp.: 175° C. |
| 434 | B4 | 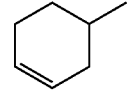 | 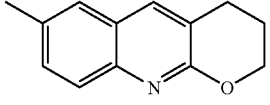 | mp.: 170° C. |
| 435 | B4 | 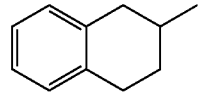 | 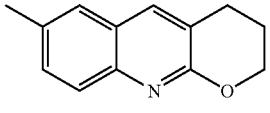 | mp.: 103° C. |
| 436 | B4 | 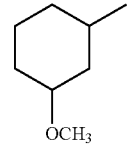 | 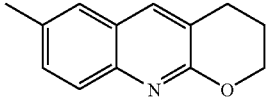 | mp.: 151° C. |
| 437 | B4 | 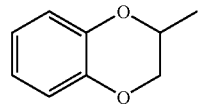 | | (trans); mp.: 110° C. |
| 438 | B4 | 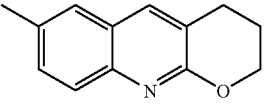 | | mp.: 150° C. |

TABLE 7-continued

| Co. no. | Ex. no. | R¹ | L | physical data |
|---|---|---|---|---|
| 439 | B4 | benzyl-CH₂- | 6-methyl-2,3-dihydro-thiopyrano[2,3-b]quinoline | mp.: 150° C. |
| 440 | B4 | 3-methoxycyclohexyl-CH₂- | 6-methyl-2,3-dihydro-pyrano[2,3-b]quinoline | (cis) |
| 441 | B4 | benzyl-CH₂- | 6-methyl-2,3-dihydro-thieno[2,3-b]quinoline | mp.: 166° C. |
| 442 | B4 | 2-(dimethylamino)-1-phenylpropyl- | 6-methyl-2,3-dihydro-thieno[2,3-b]quinoline | mp.: 173° C. |
| 443 | B4 | benzyl-CH₂- | 6-methyl-2,3-dihydro-thieno[2,3-b]quinoline-S,S-dioxide | mp.: 208° C. |
| 444 | B4 | α-methylenebenzyl- | 6-methyl-2,3-dihydro-thieno[2,3-b]quinoline | mp.: 149° C. |
| 445 | B4 | norbornyl-CH₂- | 6-methyl-2,3-dihydro-thiopyrano[2,3-b]quinoline | mp.: 133° C. |
| 446 | B3b | benzyl-CH₂- | 6-methyl-2,3-dihydro-cyclopenta[b]quinoline | mp.: 150° C. |
| 447 | B3b | norbornyl-CH₂- | 6-methyl-2,3-dihydro-thieno[2,3-b]quinoline | mp.: 165° C. |
| 448 | B3b | phenylpropyl- | 6-methyl-2,3-dihydro-thieno[2,3-b]quinoline | mp.: 147° C. |

TABLE 7-continued

| Co. no. | Ex. no. | R¹ | L | physical data |
|---|---|---|---|---|
| 449 | B3b | adamantyl | methyl-thieno-quinoline | mp.: 154° C. |
| 450 | B3b | tetrahydronaphthalenyl | methyl-thieno-quinoline | mp.: 157° C. |
| 451 | B4 | 4-methylpiperazinyl-CH₂-CH(CH₃)-phenyl | methyl-thieno-quinoline | mp.: 190° C. |
| 452 | B4 | morpholinyl-CH₂-CH(CH₃)-phenyl | methyl-thieno-quinoline | mp.: 187° C. |
| 453 | B3b | 4-bromophenyl-ethyl | methyl-thieno-quinoline | mp.: 200° C. |
| 454 | B3b | phenyl-ethyl | methyl-cyclohepta-quinoline | mp.: 160° C. |
| 455 | B3b | phenyl-ethyl | methyl-(2-methyl-furo)-quinoline | mp.: 139° C. |
| 456 | B3b | 2-oxabicyclic | methyl-pyrano-quinoline | (A); mp.: 174° C. |
| 457 | B3b | 2-oxabicyclic | methyl-pyrano-quinoline | (B); mp.: 160° C. |
| 458 | B3b | phenyl-ethyl | methyl-(N-methyl-tetrahydro-naphthyridine) | mp.: 184° C. |

TABLE 7-continued

| Co. no. | Ex. no. | R¹ | L | physical data |
|---|---|---|---|---|
| 459 | B4 | 4-cyanophenylethyl | 7-methyl-tetrahydro-benzo[b][1,6]naphthyridine-2-carboxylic acid tert-butyl ester moiety | — |
| 460 | B4 | 2-methoxy-5-methyl-3,6-dihydro-2H-pyran | 7-methyl-2,3-dihydro-pyrano-quinoline | mp.: 134° C. |
| 461 | B4 | methylnorbornenyl | 7-methyl-2,3-dihydro-pyrano-quinoline | (B); mp.: 156° C. |
| 462 | B4 | phenylethyl | 7-methyl-thieno-quinoline | mp.: 153° C. |
| 463 | B3b | phenylethyl | 7-methyl-furo-dihydro-quinoline | mp.: 161° C. |
| 464 | B4 | 3-thienylethyl | 7-methyl-2,3-dihydro-thiopyrano-quinoline | mp.: 135° C. |
| 465 | B4 | 3-thienylethyl | 7-methyl-2,3-dihydro-pyrano-quinoline | mp.: 131° C. |
| 466 | B3b | 3-methylchroman | 7-methyl-dihydro-thieno-quinoline | .HCl(1:1); mp.: 206° C. |
| 467 | B3d | phenylethyl | 8-methyl-tetrahydro-benzo[b][1,6]naphthyridine-2-carboxylic acid tert-butyl ester moiety | mp.: 142° C. |
| 468 | B4 | methyl-epoxy-cyclohexane | 7-methyl-2,3-dihydro-pyrano-quinoline | .hydrate(1:1); mp.: 104° C. |
| 469 | B3b | dimethylethyl | 7-methyl-dihydro-thieno-quinoline | mp.: 104° C. |

TABLE 7-continued

| Co. no. | Ex. no. | R¹ | L | physical data |
|---|---|---|---|---|
| 470 | B3b | 4-methyltetrahydropyran-4-yl | 6-methyl-2,3-dihydrothieno[2,3-b]quinoline | mp.: 161° C. |
| 472 | B3b | benzyl | 6-methyl-3,4-dihydro-2H-thiopyrano[2,3-b]quinoline | mp.: 144° C. |
| 473 | B4 | 3-fluorobenzyl | 6-methyl-3,4-dihydro-2H-pyrano[2,3-b]quinoline | mp.: 143° C. |
| 474 | B4 | 3,4-difluorobenzyl | 6-methyl-3,4-dihydro-2H-pyrano[2,3-b]quinoline | mp.: 196° C. |
| 475 | B4 | 4-fluorobenzyl | 6-methyl-3,4-dihydro-2H-pyrano[2,3-b]quinoline | mp.: 162° C. |
| 476 | B4 | 1-phenylethyl | 6-methyl-2,3-dihydrothieno[2,3-b]quinoline | mp.: 171° C. |
| 477 | B4 | 2-fluorobenzyl | 6-methyl-3,4-dihydro-2H-pyrano[2,3-b]quinoline | mp.: 155° C. |
| 478 | B2 | trimethylmethyl | 6-methyl-2,3-dihydrothieno[2,3-b]quinoline | mp.: 124° C. |
| 479 | B4 | 1-fluoro-4-methoxycyclohexylmethyl | 6-methyl-3,4-dihydro-2H-thiopyrano[2,3-b]quinoline | (A); mp.: 146° C. |
| 480 | B4 | 1-fluoro-4-methoxycyclohexylmethyl | 6-methyl-3,4-dihydro-2H-thiopyrano[2,3-b]quinoline | (B); mp.: 162° C. |
| 481 | B4 | 2-methylnorbornyl-2-methyl | 6-methyl-2,3-dihydrothieno[2,3-b]quinoline | (A); mp.: 129° C. |

TABLE 7-continued
| Co. no. | Ex. no. | R¹ | L | physical data |
|---|---|---|---|---|
| 482 | B4 | 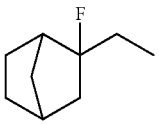 | 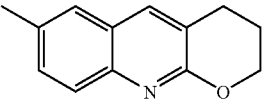 | mp.: 115° C. |
| 483 | B2 | 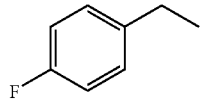 | 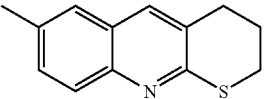 | mp.: 187° C. |
| 484 | B2 | 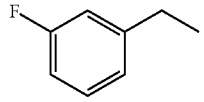 | 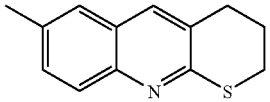 | mp.: 162° C. |
| 485 | B4 | 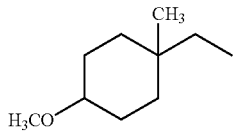 | 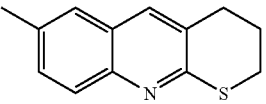 | (A); mp.: 130° C. |
| 486 | B4 | 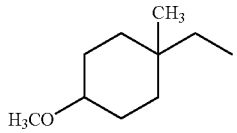 | 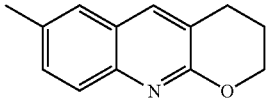 | (A); mp.: 124° C. |
| 487 | B4 | 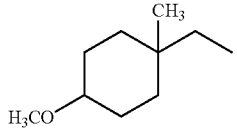 | 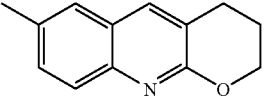 | (B); mp.: 128° C. |
| 488 | B4 | 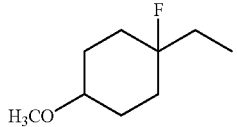 | 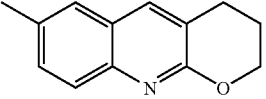 | mp.: 85° C. |
| 489 | B2 | 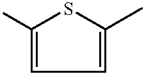 | 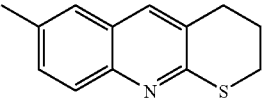 | mp.: 150° C. |
| 490 | B4 | 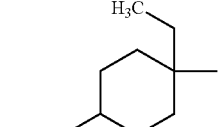 | 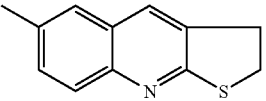 | (A); mp.: 117° C. |
| 491 | B2 | 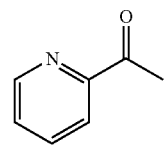 | 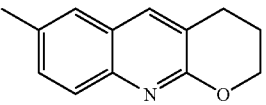 | mp.: 220° C. |

TABLE 7-continued

| Co. no. | Ex. no. | R¹ | L | physical data |
|---|---|---|---|---|
| 492 | B4 | (norbornyl with CH₃) | (methyl-thiopyrano-quinoline) | mp.: 136° C. |
| 493 | B2 | 4-(N(CH₃)₂CH₂)-phenyl-ethyl | (methyl-pyrano-quinoline) | mp.: 131° C. |
| 494 | B4 | (norbornyl with CH₃) | (methyl-pyrano-quinoline) | (A); mp.: 125° C. |
| 495 | B4 | (norbornyl with F) | (methyl-thiopyrano-quinoline) | mp.: 135° C. |
| 496 | B4 | (norbornyl with F) | (methyl-thieno-quinoline) | mp.: 139° C. |
| 497 | B4 | (ethyl-norbornyl) | (methyl-pyrano-quinoline) | mp.: 127° C. |
| 498 | B16 | 4-Br-phenyl-ethyl | (methyl-pyrano-quinoline) | mp.: 195° C. |
| 499 | B2 | 2-F-phenyl-ethyl | (methyl-thiopyrano-quinoline) | mp.: 201° C. |
| 500 | B3b | phenyl-ethyl | (methyl-methylfuro-quinoline) | mp.: 143° C. |
| 501 | B3b | phenyl-ethyl | (methyl-pyrano-quinoline) | mp.: 137° C. |
| 502 | B2 | 2-acetyl-pyridyl | (methyl-thiopyrano-quinoline) | mp.: 210° C. |

TABLE 7-continued
R¹—C(=O)—L
| Co. no. | Ex. no. | R¹ | L | physical data |
|---|---|---|---|---|
| 503 | B3d | 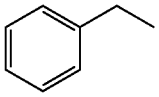 | 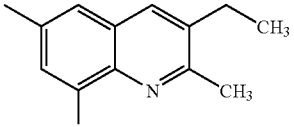 | mp.: 134° C. |
| 504 | B2 | 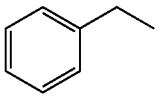 | 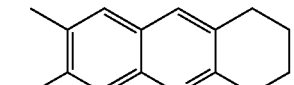 | mp.: 163° C. |
| 505 | B4 | 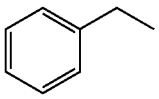 | 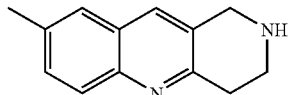 | mp.: 142° C. |
| 506 | B2 | 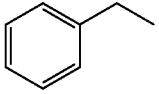 | 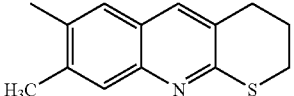 | mp.: 139° C. |
| 507 | B4 | 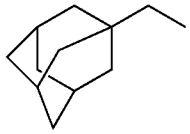 | 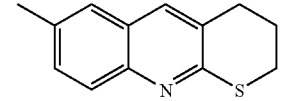 | mp.: 171° C. |
| 512 | B3b | 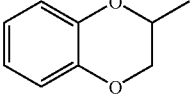 | 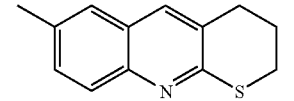 | — |
| 523 | B3b | 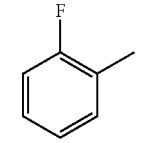 | 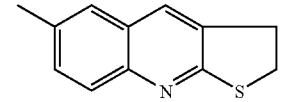 | — |
TABLE 8
| Co. no. | Ex. no. | Structure | physical data |
|---|---|---|---|
| 511 | B11 | 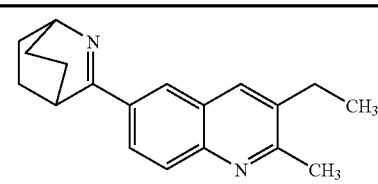 | — |
| 514 | B12 | 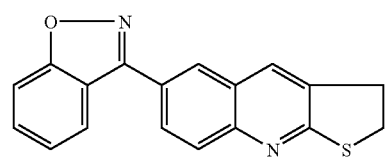 | — |

TABLE 8-continued

| Co. no. | Ex. no. | Structure | physical data |
|---|---|---|---|
| 515 | B13 | 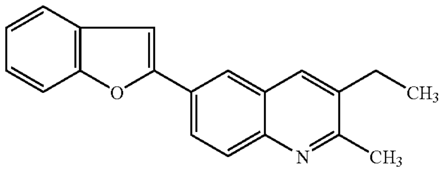 | — |
| 524 | B9a | 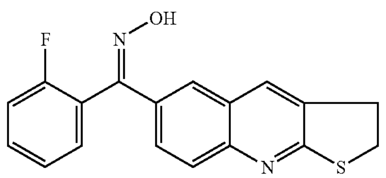 | mp.: 185° C. |
| 471 | B15 | 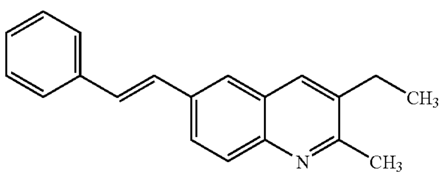 | (E) |
| 526 | B14 | 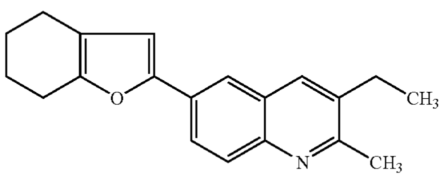 | .HCl(1:1) |

C. Preparation of Radioactively Labelled Compounds

C.1 [³H]-labelled Compounds

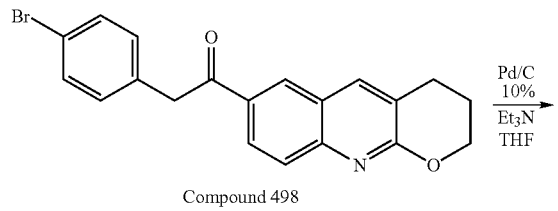

Compound 498

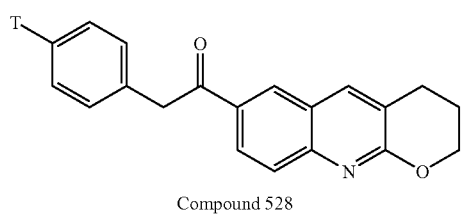

Compound 528

To a carefully measured amount of palladium on carbon (10%, 0.872 mg) was added a solution of compound 498 (I, 0.919 mg, 2.4 µmol) and triethylamine (0.92 µl, 6.6 µmol) in sodium-dried tetrahydrofuran (175 µl). The reaction flask was connected to a tritiation manifold system and the reaction mixture was carefully degassed. Tritium gas (19.5 Ci at a pressure of 1017 mbar) was generated from uranium tritide and was allowed onto the at room temperature stirred reaction mixture. After 30 min, the reaction mixture was frozen with liquid nitrogen and the excess of tritium gas was recaptured onto uranium sponge. The solvent was lyophilized from the reaction mixture. Methanol (100 µl) was introduced and lyophilized in order to remove labile tritium. This procedure was repeated twice more. The residue was taken up in ethanol, filtered over a GHP Acrodisk 13 mm syringe filter and depleted with ethanol to a total volume of 50.0 ml. It contained 71 mCi of radioactivity with [³H]-compound 528 (II) at a 67% radiochemical purity. From this amount, a fraction (5.0 ml) was taken and thoroughly purified in portions via preparative HPLC (Kromasil KR100-10, column dimensions 4.6 mm ID×300 mm). UV detection took place at 265 nm. Elution was performed isocratically with water-methanol-acetonitrile-diisopropylamine (47:26.5:26.5:0.2; v/v/v/v) at a flow rate of 2.0 ml/min. The product containing fractions were combined and concentrated under vacuum at 30° C. The residue was dissolved in ethanol (5.0 ml) and concentrated again. This procedure was repeated twice more. The remaining residue was finally dissolved in ethanol (20.0 ml) and stored as such. The batch contained [³H]-compound 528 (II)

D. Pharmacological Examples

D1. Signal Transduction at the Cloned Rat mGlu1 Receptor in CHO Cells

CHO cells expressing the mGlu1 receptor were plated in precoated black 96-well plates. The next day, the effect of the present compounds on glutamate-activated intracellular $Ca^{2+}$ increase was evaluated in a fluorescent based assay. The cells were loaded with Fluo-3 AM, plates were incubated for 1 hour at room temperature in the dark, cells were washed and the present compounds were added onto the cells for 20 minutes. After this incubation time, the glutamate-induced $Ca^{2+}$ rise was recorded for each well in function of time using the Fluorescent Image Plate Reader (FLIPR, Molecular Devices Inc.). Relative fluorescence units were recorded and average data graphs of quadruple wells were obtained. Concentration-response curves were constructed based on peak fluorescence (maximum signal between 1 and 90 secondes) for each concentration of tested compound. $pIC_{50}$ values are the −log values of the concentration of the tested compounds resulting in 50% inhibition of the glutamate-induced intracellular $Ca^{2+}$ rise.

The compounds according to the present invention exhibited a $pIC_{50}$ value of at least 5.

The compounds that are included in the Tables 1-8 exhibited a $pIC_{50}$ value of at least 6.

A particular group of compounds exhibited a $pIC_{50}$ value between 7 and 8. It concerns the compounds listed in Table 9.

TABLE 9

| Com.nr. | $pIC_{50}$ |
|---|---|
| 463 | 7.98 |
| 441 | 7.95 |
| 334 | 7.95 |
| 22 | 7.94 |
| 421 | 7.94 |
| 15 | 7.93 |
| 440 | 7.93 |
| 139 | 7.93 |
| 178 | 7.92 |
| 338 | 7.91 |
| 87 | 7.90 |
| 462 | 7.90 |
| 394 | 7.90 |
| 423 | 7.89 |
| 21 | 7.87 |
| 220 | 7.87 |
| 479 | 7.86 |
| 483 | 7.86 |
| 485 | 7.84 |
| 9 | 7.84 |
| 110 | 7.84 |
| 248 | 7.84 |
| 341 | 7.83 |
| 163 | 7.81 |
| 433 | 7.79 |
| 238 | 7.79 |
| 224 | 7.78 |
| 437 | 7.78 |
| 498 | 7.78 |
| 449 | 7.77 |
| 242 | 7.76 |
| 346 | 7.74 |
| 182 | 7.73 |
| 486 | 7.73 |
| 447 | 7.72 |
| 7 | 7.72 |
| 175 | 7.71 |

TABLE 9-continued

| Com.nr. | $pIC_{50}$ |
|---|---|
| 475 | 7.71 |
| 480 | 7.71 |
| 213 | 7.70 |
| 239 | 7.70 |
| 241 | 7.67 |
| 461 | 7.65 |
| 115 | 7.64 |
| 445 | 7.63 |
| 281 | 7.63 |
| 487 | 7.63 |
| 299 | 7.63 |
| 431 | 7.61 |
| 98 | 7.57 |
| 464 | 7.57 |
| 446 | 7.56 |
| 251 | 7.55 |
| 484 | 7.54 |
| 494 | 7.53 |
| 128 | 7.52 |
| 344 | 7.52 |
| 161 | 7.49 |
| 298 | 7.48 |
| 454 | 7.45 |
| 456 | 7.45 |
| 277 | 7.44 |
| 91 | 7.43 |
| 356 | 7.42 |
| 229 | 7.41 |
| 333 | 7.41 |
| 326 | 7.41 |
| 369 | 7.40 |
| 430 | 7.39 |
| 435 | 7.38 |
| 35 | 7.36 |
| 228 | 7.36 |
| 429 | 7.36 |
| 117 | 7.35 |
| 291 | 7.35 |
| 313 | 7.35 |
| 280 | 7.34 |
| 460 | 7.34 |
| 482 | 7.34 |
| 343 | 7.33 |
| 425 | 7.32 |
| 473 | 7.32 |
| 287 | 7.31 |
| 448 | 7.31 |
| 243 | 7.29 |
| 323 | 7.28 |
| 159 | 7.28 |
| 289 | 7.27 |
| 184 | 7.26 |
| 436 | 7.26 |
| 89 | 7.25 |
| 108 | 7.25 |
| 373 | 7.25 |
| 255 | 7.23 |
| 527 | 7.23 |
| 303 | 7.22 |
| 296 | 7.22 |
| 221 | 7.21 |
| 193 | 7.21 |
| 14 | 7.20 |
| 131 | 7.19 |
| 438 | 7.19 |
| 148 | 7.18 |
| 496 | 7.18 |
| 236 | 7.17 |
| 332 | 7.17 |
| 481 | 7.16 |
| 191 | 7.16 |
| 457 | 7.14 |
| 20 | 7.14 |
| 145 | 7.13 |
| 268 | 7.13 |
| 512 | 7.13 |
| 474 | 7.13 | with a total radioactivity of 3.83 mCi at a purity>98% and at a specific activity of about 25 Ci/mmol.

TABLE 9-continued

| Com.nr. | pIC$_{50}$ |
|---|---|
| 10 | 7.11 |
| 307 | 7.11 |
| 426 | 7.11 |
| 466 | 7.10 |
| 97 | 7.08 |
| 83 | 7.08 |
| 434 | 7.08 |
| 300 | 7.08 |
| 199 | 7.07 |
| 290 | 7.06 |
| 112 | 7.05 |

TABLE 9-continued

| Com.nr. | pIC$_{50}$ |
|---|---|
| 348 | 7.05 |
| 286 | 7.03 |
| 442 | 7.03 |
| 422 | 7.02 |
| 283 | 7.02 |
| 318 | 7.02 |
| 36 | 7.00 |
| 396 | 7.00 |

A particular group of compounds exhibited a pIC$_{50}$ value of at least 8. It concern the compounds listed in Table 10.

TABLE 10

| Comp. nr. | Structure | pIC50 |
|---|---|---|
| 416 | (CIS) | 8.587 |
| 27 | (CIS) | 8.527 |
| 174 | (CIS) | 8.49 |
| 506 | 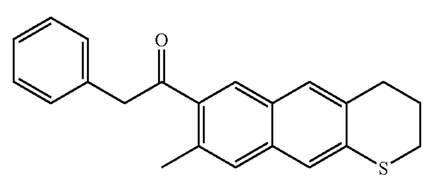 | 8.48 |
| 25 | (CIS) | 8.45 |
| 4 | (CIS) | 8.4 |

TABLE 10-continued

| Comp. nr. | Structure | pIC50 |
|---|---|---|
| 19 | (CIS) | 8.38 |
| 429 | (CIS) | 8.38 |
| 424 | (CIS) | 8.355 |
| 176 | (CIS) | 8.33 |
| 210 | (CIS) | 8.315 |
| 114 | (CIS) | 8.28 |
| 488 | 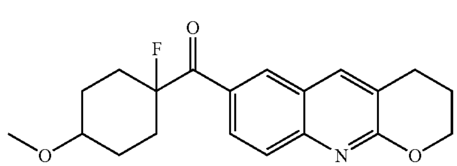 | 8.27 |

TABLE 10-continued

| Comp. nr. | Structure | pIC50 |
|---|---|---|
| 504 | 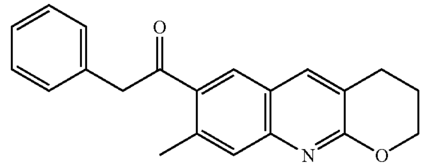 | 8.27 |
| 477 | 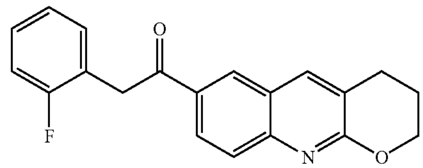 | 8.25 |
| 432 | 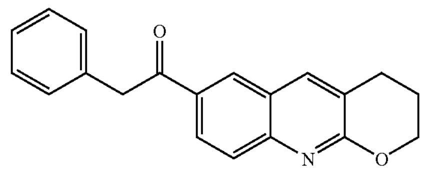 | 8.237 |
| 214 | (CIS) | 8.233 |
| 465 | 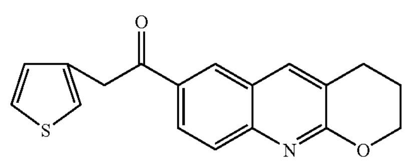 | 8.145 |
| 135 | (CIS) | 8.14 |
| 420 | (CIS) Hydrochloride (1:1) | 8.135 |
| 292 | (CIS) | 8.13 |

TABLE 10-continued

| Comp. nr. | Structure | pIC50 |
|---|---|---|
| 427 | (cyclohexyl-C(=O)- fused quinoline with dihydrothiophene) | 8.115 |
| 208 | (4-methoxycyclohexyl-C(=O)- fused quinoline with N-methyl tetrahydropyridine) (CIS) | 8.095 |
| 419 | (4-methoxycyclohexyl-C(=O)- 3-ethyl-7-methyl-2-oxo-1,2-dihydroquinoline) (CIS) | 8.065 |
| 455 | (benzyl-C(=O)- fused quinoline with 2-methyl dihydrofuran) | 8.055 |
| 418 | (4-methoxycyclohexyl-C(=O)- fused quinoline with dihydrothiophene) (TRANS) | 8.045 |
| 497 | (norbornyl-CH2-C(=O)- fused quinoline with dihydropyran) | 8.025 |
| 439 | (benzyl-C(=O)- fused quinoline with dihydrothiopyran) | 8.023 |
| 237 | (benzyl-C(=O)- 2-methyl-3-ethylquinoline) | 8.01 |

TABLE 10-continued

| Comp. nr. | Structure | pIC50 |
|---|---|---|
| 499 | [structure: 2-fluorophenyl-CH2-C(=O)- attached to 2,3-dihydro-thiopyrano[3,2-b]quinoline] | 8 |

D2. In Vitro Binding Experiments with a [³H]-radiolabelled Compound According to the Invention As [³H]-radiolabelled compounds are used: compound 528, hereafter named as [³H]Compound A, which is the tritium-radiolabelled equivalent of compound 432.

In the next paragraphs, a study will be disclosed illustrating the use of radiolabelled compounds according to the invention.

Materials

All cell culture reagents were obtained from Invitrogen (Carlsbad, USA). Glutamate was obtained from Aldrich Chemical Company (Milwaukee, Wis.); [³H]quisqualate (29 Ci/mmol), [³H]Ro 48-8587 (53 Ci/mmol), myo-[³H]-inositol (22 Ci/mmol) and [³⁵S]GTPγS (1030 Ci/mmol) were obtained from Amersham (Paisley, UK). [³R]MK-801 (22.5 Ci/mmol) and [³H]CGP39653 (20-50 Ci/mmol) were obtained from NEN (Zaventem, Belgium). GDP was obtained from Boehringer Manheim (Basel, Switzerland) and glycine from BioRad (CA, USA). [³H]L689560 (10-30 Ci/mmol), [³H]LY341495 (34.61 Ci/mmol), [³H]MPEP (50.2 Ci/mmol), (S)-4C3HPG, (1S,3R)-ACPD, (S)-3,5-DHPG, (S)-4CPG, AIDA, MCPG, MPEP, CPCCOEt, L-SOP and L-quisqualic acid were purchased from Tocris Cookson (Essex, UK). BAY 36-7620, NPS 2390 and phencyclidine were synthesized in-house. Fluo-3-AM and pluronic acid were obtained from Molecular Probes (Leiden, The Netherlands). Probenecid, strychnine, D-serine and Triton X-100 were purchased from Sigma-Aldrich (Steinheim, Germany). All other reagents were from Merck (Darmstadt, Germany).

Cell Transfection and Culture

L929sA cells stably expressing the human mGlu1a receptor were obtained as described in Lavreysen et al., *Mol. Pharmacol.* 61:1244-1254, 2002 and were cultured in Glutamax-I medium supplemented with 10% heat inactivated dialysed foetal calf serum, 0.1 mg/ml streptomycin sulphate and 100 units/ml penicillin. CHO-dhfr⁻ cells stably expressing the rat mGlu1a, -2, -3, -4, -5 and -6 receptor were a kind gift from S. Nakanishi (Tokyo University, Japan) and were grown in DMEM with Glutamax-I with 10% heat inactivated dialysed foetal calf serum, 0.4 mM L-prolin, 0.2 mg/ml streptomycin sulphate and 200 units/ml penicillin. Cells were kept in an atmosphere of 37° C. and 5% $CO_2$.

Intracellular $Ca^{2+}$ Response in Rat and Human mGlu1a Receptor Expressing Cells and in Rat mGlu5 Receptor Expressing Cells.

Intracellular calcium ion levels ($[Ca^{2+}]_i$) in human mGlu1a receptor expressing L929sA cells were measured using the Fluorometric Imaging Plate Reader (FLIPR, Molecular Devices, CA, USA), as described in Lavreysen et al., *Mol. Pharmacol.* 61:1244-1254, 2002. The same procedure was followed for CHO-dhfr⁻ cells expressing the rat mGlu1a receptor. For the rat mGlu5 receptor, cells were seeded at 30.000 cells/well 2 days before the experiment.

IP Response in Rat mGlu1a Receptor Expressing CHO-dhfr⁻ Cells

IP accumulation was measured as described in Lavreysen et al., *Mol. Pharmacol.* 61:1244-1254, 2002. Briefly, cells were seeded at 30,000 cells/well in 24-well plates and were labelled with 2.5 µCi/ml myo-[³H]inositol overnight. On the day of the experiment, cells were washed and incubated for 10 min with 10 mM LiCl. After 30 min incubation with increasing concentrations of [³H]Compound A, 1 N $HClO_4$ was added and plates were put at 4° C. KOH/phosphate solution and a solution containing 30 mM $Na_2B_4O_7.10H_2O$ and 3 mM EDTA were added prior to application to ion exchange chromatography.

Membrane Preparation from CHO-dhfr⁻ Cells Expressing the Rat mGlu1a, -2, -3, -4, -5 and -6 Receptor Confluent cells were washed in ice-cold phosphate-buffered saline and stored at −20° C. until membrane preparation. After thawing, cells were suspended in 50 mM Tris-HCl, pH 7.4 and collected through centrifugation for 10 min at 23,500 g at 4° C. The cells were lysed in 10 mM hypotonic Tris-HCl, pH 7.4. After recentrifugation for 20 min at 30,000 g at 4° C., the pellet was homogenized with an Ultra Turrax homogenizer in 50 mM Tris-HCl, pH 7.4. Protein concentrations were measured by the Bio-Rad protein assay using bovine serum albumin as standard.

[³⁵S]GTPγS Binding to Membranes from CHO-dhfr⁻ Cells Expressing the Rat mGlu2, -3, -4 and -6 Receptor Membranes were thawed on ice and diluted in 10 mM HEPES acid, 10 mM HEPES salt, pH 7.4, containing 100 mM NaCl, 3 mM $MgCl_2$, 3 µM GDP and 10 µg/ml saponine. Assay mixtures contained 10 µg of membrane protein and were pre-incubated with compounds or buffer for 5 min at 37° C. Then, glutamate was added and the assay mixtures were further incubated for 30 min at 37° C. [³⁵S]GTPγS was added to a final concentration of 0.1 nM for another 30 min at 37° C. Reactions were terminated by rapid filtration through Unifilter-96 GF/B filter plates (Packard, Meriden, Conn.) using a 96-well Packard filtermate harvester. Filters were washed 2 times with ice-cold 10 mM $NaH_2PO_4$/10 mM $Na_2HPO_4$ buffer, pH 7.4. Filter-bound radioactivity was counted in a Microplate Scintillation and Luminesence Counter from Packard.

Radioligand Binding to Rat mGlu1a Receptor CHO-dhfr⁻ Membranes

[³H]Compound A-binding. After thawing, the membranes were homogenized using an Ultra Turrax homogenizer and suspended in ice-cold binding buffer containing 50 mM Tris- HCl (pH 7.4), 1.2 mM $MgCl_2$, 2 mM $CaCl_2$, unless otherwise indicated. Ligand saturation experiments were performed at apparent binding equilibrium (30 min incubation) with 20 µg membrane protein and 10 concentrations (0.1, 0.2, 0.3, 0.4, 0.5, 1, 2, 2.5, 5 and 10 nM) of radioligand. Non-specific binding was estimated in the presence of 1 µM compound 135. The incubation was stopped by rapid filtration under suction over GF/C glass-fibre filters using a manual 40-well filtration manifold. To measure association kinetics, membranes were incubated at 4° C., 25° C. or 37° C. in the presence of 2.5 nM [$^3$H]Compound A for 2, 5, 10, 15, 20, 30, 45, 60, 90 or 120 min, then terminated by rapid filtration using a manual 40-well filtration unit. Dissociation kinetics were measured by adding, at different times before filtration 1 µM compound 135 to membranes preincubated for 30 min at 4° C. or 25° C. in the presence of 2.5 nM [$^3$H]Compound A. The filters were transferred to scintillation vials and, after the addition of Ultima-Gold MV, the radioactivity collected on the filters was counted in a Packard scintillation counter. For inhibition experiments, assay mixtures were incubated for 30 min at 4° C. in a volume of 0.5 ml containing 10-20 µg membrane protein, appropriate concentrations of test compounds and 2.5 nM [$^3$H]Compound A. Non-specific binding was defined as above. Filtration was performed using Unifilter-96 GF/C filter plates and a 96-well Packard filtermate harvester. After the addition of microscint-O, radioactivity on the filters was counted in a Microplate Scintillation and Luminesence Counter from Packard.

[$^3$H]quisqualate binding. Thawed membranes were homogenized and suspended in ice-cold binding buffer. For saturation experiments, 30 µg of membrane protein was incubated for 1 h at 25° C. with 10 concentrations (1, 2, 5, 10, 20, 40, 60, 90, 120 and 150 nM) of [$^3$H]quisqualate. Non-specific binding was determined in the presence of 1 mM L-glutamate. Bound and free radioligand was separated by rapid filtration over GF/C glass-fibre filters using a manual 40-well filtration manifold. For inhibition experiments, 30 µg membrane protein was incubated for 1 h at 25° C. in a volume of 0.5 ml containing appropriate concentrations of test compounds and a final concentration of 10 nM [$^3$H]quisqualate. Filtration was performed using Unifilter-96 GF/C filter plates and a Packard filtermate harvester. Radioactivity trapped on the filters was counted as above.

Radioligand Binding to Membranes from CHO-dhfr$^-$ Cells Expressing the Rat mGlu2, -3, -4, -5 and -6 Receptor After thawing, the membranes were homogenized using an Ultra Turrax homogenizer and suspended in ice-cold binding buffer containing 50 mM Tris-HCl (pH 7.4), 1.2 mM $MgCl_2$, 2 mM $CaCl_2$. For [$^3$H]Compound A binding, 20 to 160 µg membrane protein and a final concentration of 20 nM [$^3$H] Compound A was used. As indicated in the results section, different blancs were used to define non-specific binding. Incubation time and temperature as well as filtration were as described for rat mGlu1a receptor CHO-dhfr$^-$ membranes. Expression of rat mGlu2, -3, -5 and mGlu6 receptors was confirmed by specific binding of [$^3$H]LY341495 (mGlu2, -3 and -6) or [$^3$H]MPEP (mGlu5). For [$^3$H]LY341495 binding, 1 nM (mGlu2 and mGlu3) or 10 nM (mGlu6) [$^3$H]LY341495 was used. Non-specific binding was determined using 1 mM glutamate. Assay mixtures were incubated for 30 min (mGlu2 and mGlu3) or 60 min (mGlu6) at 4° C. Incubation was stopped by filtration over GF/B glass fibre filters (Whatman, England) using a manual 40-well filtration manifold. For rat mGlu5 receptor CHO-dhfr$^-$ membranes, 10 nM [$^3$H]MPEP and 10 µM MPEP, to reveal non-specific binding, were used. Incubation was performed at 4° C. for 30 min. Bound and free radioligand were separated over GF/C glass-fibre filters (Whatman, England) using a 40-well filtration unit.

[$^3$H]Compound A Binding to Rat Brain Membranes.

Tissue preparation. Male Wistar rats (~200 g) were sacrificed by decapitation. The brains were rapidly removed and cortex, hippocampus, striatum and cerebellum were immediately dissected. The fresh tissue was homogenized with an Ultra Turrax in 20 volumes of 50 mM Tris-HCl, pH 7.4 and tissue was centrifuged at 23,500 g for 10 min. After homogenisation using a DUAL homogeniser, membranes were washed twice by centrifugation at 23,500 g for 10 min. The final pellet was suspended in 10 volumes of 50 mM Tris-HCl, pH 7.4 and frozen at −80° C.

In vitro binding assay. After thawing, membranes from rat cortex, cerebellum, striatum and hippocampus were rehomogenized using a DUAL and suspended in ice-cold binding buffer containing 50 mM Tris-HCl, 1.2 mM $MgCl_2$, 2 mM $CaCl_2$, pH 7.4. The binding assay was carried out in a total volume of 0.5 ml containing 2.5 nM [$^3$H]Compound A and a membrane aliquot corresponding to 40 µg for cerebellar membranes, 60 µg for hippocampal membranes, 80 µg for striatal membranes or 150 µg for cortical membranes. Specific binding was calculated as the difference between the total binding and the binding measured in the presence of 1 µM compound 135. After incubation for 30 min at 4° C., the labelled membranes were washed and harvested by rapid vacuum filtration over Whatman GF/C glass-fibre filters using a 40-well filtration manifold and radioactivity collected on the filters was counted as above.

[$^3$H]Ro 48-8587, [$^3$H]L689560, [$^3$H]CGP39653 and [$^3$H]MK-801 Binding to Rat Brain Membranes.

Tissue preparation. Male Wistar rats (~200 g) were sacrificed by decapitation. The brains were rapidly removed and forebrain was dissected. The tissue was homogenized with an Ultra Turrax in 20 volumes of ice-cold $H_2O$ and was centrifuged at 48,000 g for 20 min. After homogenisation using a DUAL homogeniser, membranes were washed by centrifugation at 48,000 g for 10 min. The pellet was then suspended in 20 volumes of 50 mM Tris-HCl, pH 7.4 containing 0.04% Triton X-100 and again centrifuged at 48,000 g for 20 min. The final pellet was frozen at −80° C.

In vitro binding assay. At the day of the experiment, the pellet was thawed, washed and rehomogenised using a DUAL in ice-cold 50 mM Tris-acetate, pH 7.4. Assay conditions for the different radioligands were as follows. The final concentration of membrane in the assay was 20 mg/ml (wet weight) for [$^3$H]Ro 48-8587 and [$^3$H]L689560 and was 10 mg/ml (wet weight) for [$^3$H]CGP39653 and [$^3$H]MK-801. Radioligand concentrations of 2 nM [$^3$H]Ro 48-8587, 2 nM [$^3$H]L689560, 2 nM [$^3$H]CGP39653 and 3 nM [$^3$H]MK-801 were used. Incubation was performed in the presence of 1 mM KSCN for [$^3$H]Ro 48-8587, 100 µM strychnine for [$^3$H]L689560 and 1 µM glycine+1 µM glutamate for [$^3$H]MK-801 binding. Non-specific binding was determined in the presence of 1 mM glutamate for [$^3$H]Ro 48-8587 and [$^3$H]CGP39653 binding. For [$^3$H]L689560 and [$^3$H]MK-801 binding, 100 µM D-serine or 10 µM phencyclidine were used to define non-specific binding, respectively. Assays were incubated for 1 h at 37° C., 2 h at 4° C., 30 min at 25° C. and 1 h at 4° C. for [$^3$H]Ro 48-8587, [$^3$H]L689560, [$^3$H]CGP39653 and [$^3$H]MK-801 binding, respectively. After incubation, bound and free radioligand was separated using a 40-well filtration manifold. Radioactivity collected on the filters was counted as above.

[³H]Compound A-binding and Autoradiography on Rat Brain Sections.

Tissue preparation. Male Wistar rats (200 g) were sacrificed by decapitation. Brains were immediately removed from the skull and were rapidly frozen in dry-ice-cooled 2-methylbutane (−40° C.). Brains were then stored at −70° C. until sectioning. Twenty-micrometer-thick sagittal sections were cut using a Leica C3050 cryostat microtome (Leica Microsystems, Wetzlar, Germany) and thaw-mounted on SuperFrost Plus microscope slides (Menzle-glaser, Germany). The sections were then kept at −70° C. until use.

Receptor autoradiography. Sections were thawed and dried under a stream of cold air, preincubated (3×5 min) in 50 mM Tris-HCl, 1.2 mM $MgCl_2$, 2 mM $CaCl_2$, 0.1% BSA pH 7.4 at room temperature. Sections were then incubated for 60 min at room temperature, in buffer containing 50 mM Tris-HCl, 1.2 mM $MgCl_2$, 2 mM $CaCl_2$, 0.1% BSA (pH 7.4) and 1.5 nM [³H]Compound A. Non-specific binding was determined by addition of 1 µM compound 135 in the incubation buffer. After the incubation, the excess of radioligand was washed off (3×5 min) in ice-cold buffer containing 50 mM Tris-HCl, 1.2 mM $MgCl_2$ and 2 mM $CaCl_2$, followed by a rapid dip in cold distilled water. The sections were dried under a stream of cold air and then exposed to [³H]Hyperfilm (Amersham, UK) for 6 weeks at room temperature. The films were developed manually in Kodak D19 and fixed with Kodak Readymatic. Some sections were exposed to a Fuji Imaging Plate for 2 days at room temperature and scanned using a Fujix Bass 2000 phosphoimager.

Data Analysis and Statistics

Data analysis was performed using the GraphPad Prism program (GraphPad Prism Software, Inc., San Diego, Calif.). Saturation binding experiments were analysed using a non-linear regression analysis. Inhibition curves were fitted using non-linear regression analysis fitting the one-site competition equation: $Y=Bottom+((Top-Bottom)/1+10^{X-LogIC50})$. $K_i$ values were calculated using the Cheng-Prusoff equation: $K_i=IC_{50}/[1+([C]/K_D)]$ where C is the concentration of radioligand and $K_D$ is the dissociation constant of the radioligand (Cheng and Prusoff, *Biochem. Pharmacol.* 22, 3099-3108, 1973). The observed on ($k_{ob}$) and off ($k_{off}$) rate were calculated from association-dissociation curves using the one-phase-exponential association and decay equations in the Prism program, respectively. $k_{on}$ was calculated by subtracting $k_{off}$ from $k_{ob}$ and dividing by the radioligand concentration. The two-tailed Student's t-test was used for statistical evaluation of the binding data: * $p<0.05$,  $p<0.01$ and * $p<0.001$. The Dunnett's t-test following a 2-way analysis of variance (with as factors compound concentration and experiment) were used to analyse the data from the IP experiments.

Results

Selectivity and mode of antagonism of Compound A for the mGlu1 receptor. In CHO-dhfr⁻ cells expressing the rat mGlu1a receptor, compound A inhibited the glutamate-induced increase in $[Ca^{2+}]_i$ with an $IC_{50}$ value of 21.6±5.0 nM (n=4; FIG. 1A) and appeared to be about 8 times more potent than the recently described specific mGlu1 receptor antagonist BAY 36-7620 ($IC_{50}$=161±38 nM, n=3) and 500 times more potent than CPCCOEt ($IC_{50}$=10.3±0.8 µM, n=3), tested in the same assay. For the human mGlu1a receptor, compound A had an $IC_{50}$ value of 10.4±4.7 nM (n=3). Compound A did not inhibit glutamate-induced $Ca^{2+}$ signaling of the rat mGlu5 receptor expressed in CHO-dhfr⁻ cells, tested up to a concentration of 10 µM. $IC_{50}$ values for inhibition of glutamate (30 µM)-induced [³⁵S]GTPγS activation were above 30 µM at recombinant rat mGlu2, -3, -4 or -6 receptors. In [³⁵S]GTPγS assays, compound A did not exhibit agonist activity towards any of the mGlu receptors up to a concentration of 30 µM. In addition, it was investigated whether compound A could act as a positive allosteric modulator on one of these mGlu receptor types. For this, we performed glutamate concentration-response curves by adding glutamate alone or together with 10 µM compound A. [³⁵S]GTPγS assays on recombinant rat mGlu2, -3, -4 or -6 receptors showed that the glutamate $EC_{50}$ was not altered and that the glutamate $E_{max}$ value was not increased upon addition of compound A. The $EC_{50}$ and $E_{max}$ value of glutamate-induced intracellular $Ca^{2+}$ mobilization also did not change in cells expressing the rat mGlu5 receptor when compound A was added together with glutamate (data not shown). Together these data exclude agonist, antagonist or positive allosteric action on mGlu2, -3, -4, -5 and -6 receptors. Radioligand binding studies on rat forebrain using [³H]Ro-488587, [³H]L689560, [³H]CGP39653 and [³H]MK-801 revealed that compound A did not bind to the AMPA receptor, nor did it bind to the glycine, glutamate or channel pore site of the NMDA receptor (tested up to a concentration of 10 µM), respectively. To analyse how compound A inhibits glutamate activation of the mGlu1a receptor, mobilization of $Ca^{2+}$ in response to glutamate was compared in the absence and presence of compound A (FIG. 1B). The presence of compound A not only caused a right-ward shift in the concentration-response curve of glutamate, but also resulted in a dramatic decrease in the maximal response evoked by the agonist, revealing that antagonism by compound A was non-competitive. Complete inhibition of mGlu1a receptor-mediated signalling was observed in the presence of 100 nM-1 µM compound A. To investigate whether compound A could act as an inverse agonist, we measured basal IP accumulation in rat mGlu1a receptor containing CHO-dhfr⁻ cells in the presence of compound A. FIG. 1C shows that there is a clear reduction in basal IP production with increasing concentration of compound A. This reduction was statistically significant (p<0.05) as off 1 µM compound A, at which basal IP accumulation decreased by 24±4%. A maximal decrease of 33±3% was found when using 100 µM compound A. These data indicate that compound A can indeed act as an inverse agonist towards the mGlu1a receptor.

Figure 2:
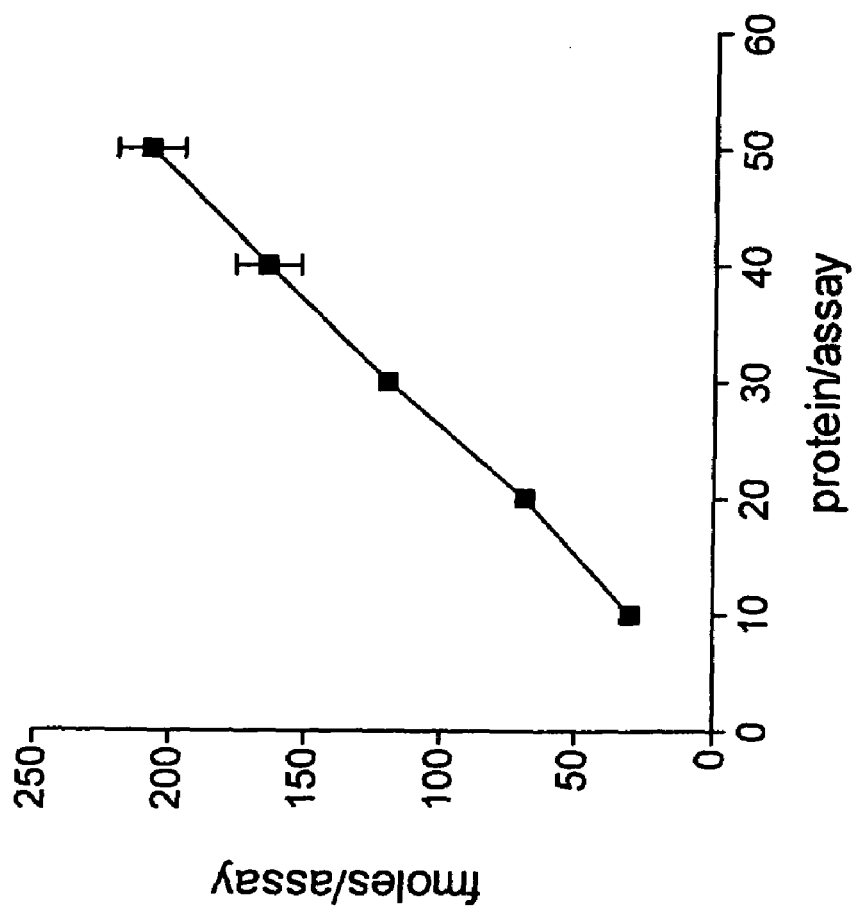

Characterization of [³H]Compound A binding to rat mGlu1a receptor CHO-dhfr⁻ membranes. The specific binding of 2.5 nM [³H]Compound A at 4° C. to rat mGlu1a receptor CHO-dhfr⁻ membranes was proportional to the amount of membrane protein and increased linearly between 10 and 50 µg membrane protein per assay (FIG. 2). Non-specific binding was defined using 1 µM compound 135 as inhibitor. compound 135 was identified as a specific mGlu1 receptor antagonist with a potency of 7.2±1.2 nM (n=3) for reversal of glutamate-induced $[Ca^{2+}]_i$ mobilization. Using 20 µg protein per assay, specific binding of [³H]Compound A was ~92% of the total binding; in typical assay conditions, total and non-specific binding were in the range of 3,800 and 300 DPM, respectively.

Addition of 1.2 mM $MgCl_2$ and 2 mM $CaCl_2$ caused a slight increase in specific binding (data not shown). Further addition of NaCl (10-100-300 mM) had no effect. While specific binding decreased by 22% at pH 6, increasing the pH up to 10 had no effect (data not shown).

Association kinetics were measured as described in Materials and Methods.

Figure 3:
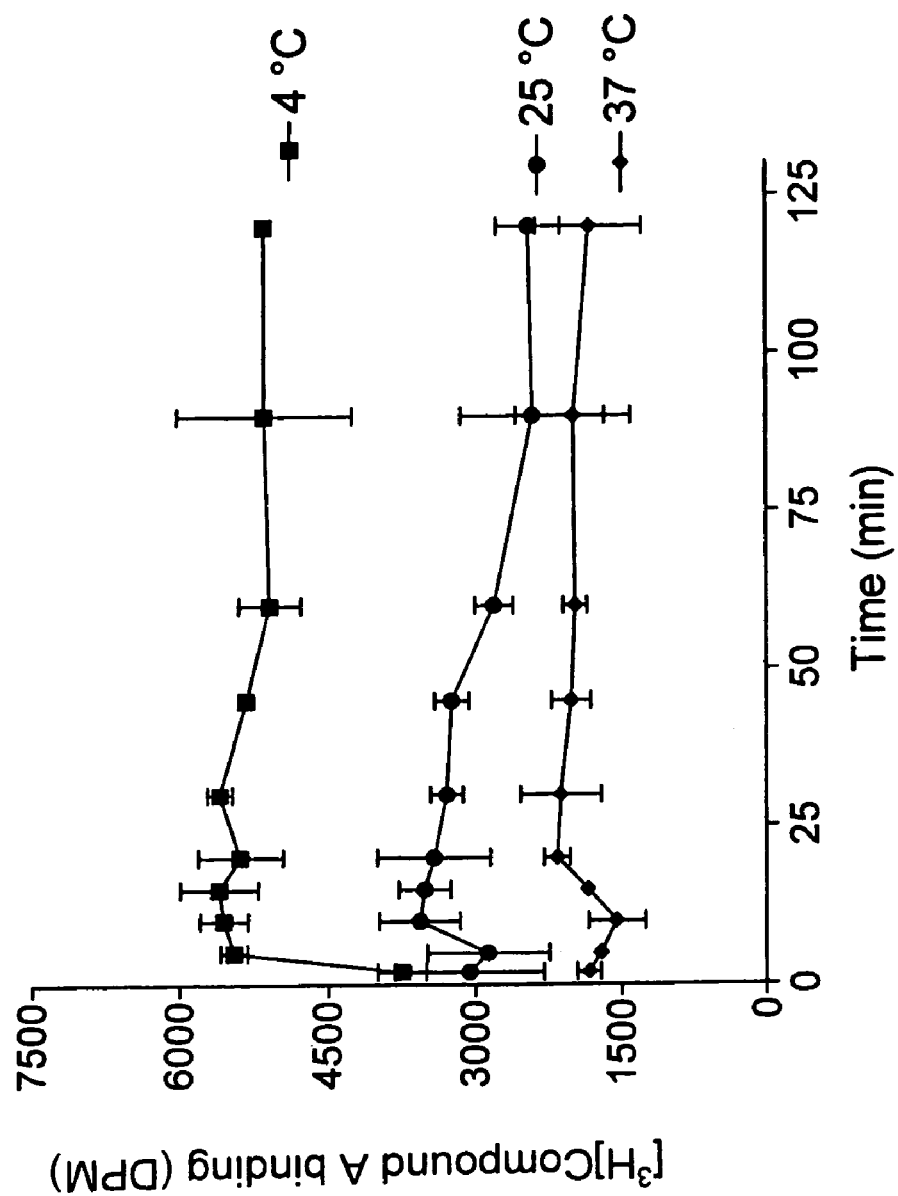
Figure 4:
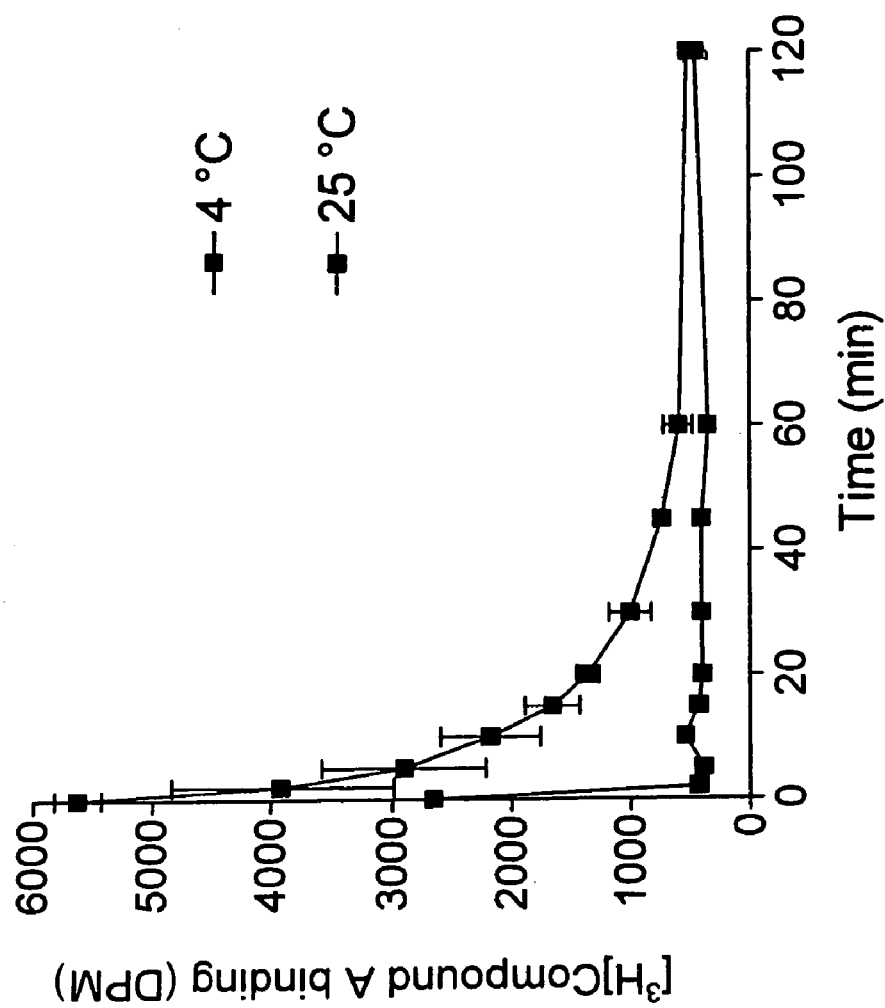

Decreasing the incubation temperature to 4° C., dramatically enhanced specific binding, whereas a low binding was found at 37° C. (FIG. 3). The association of [³H]Compound A to membranes was extremely fast. At 4° C., 2 min incubation resulted already in a specific binding corresponding to about 70% of the quantity bound at equilibrium. Maximal binding was reached within 5 min incubation for each incubation temperature. Analysis of the association curves resulted in observed association rate constants ($k_{ob}$) of 0.6285, 2.571 and 1.523 min⁻¹ at 4° C., 25° C. and 37° C., respectively. The kinetics of dissociation were also rapid (FIG. 4). At 25° C., the radioligand dissociated within as little as 2 min after 1 μM compound 135 was added to the reaction tubes. The rapid dissociation kinetics at 25° C. did not allow us to calculate an accurate dissociation rate constant ($k_{off}$). Dissociation occurred more gradual when incubated at 4° C. [$^3$H]Compound A was displaced completely within approximately 45 min after the addition of an excess compound 135. Analysis of the dissociation curve at 4° C. resulted in an $k_{off}$ of 0.1249 min$^{-1}$ $k_{on}$ ($k_{ob}$-$k_{off}$/radioligand concentration) at 4° C. was 0.1007 nM$^{-1}$ min$^{-1}$.

Figure 5:
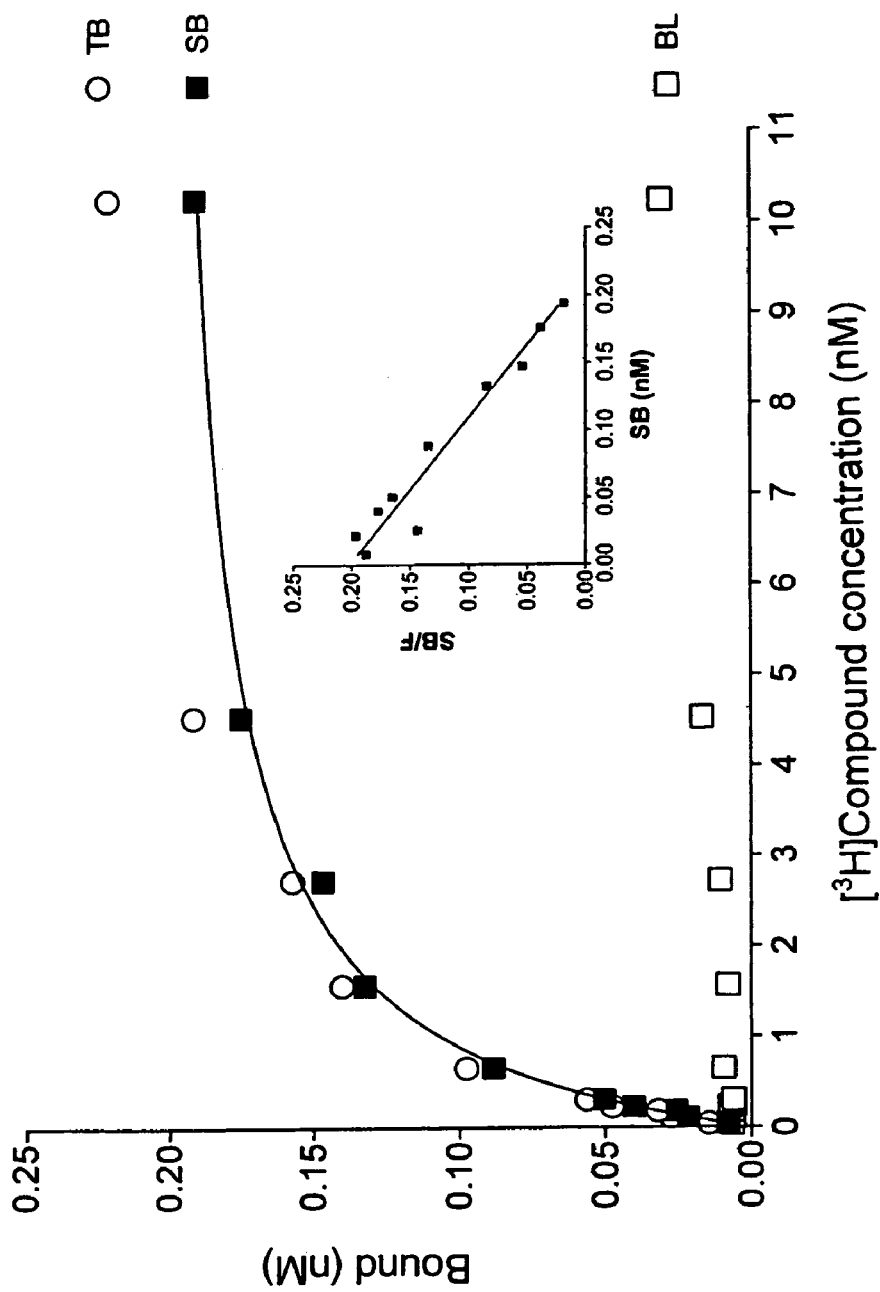

Ligand saturation experiments were performed at apparent binding equilibrium (30 min incubation) and with 10 concentrations of radioligand. FIG. 5 shows the saturation curve and Scatchard Plot of [$^3$H]Compound A binding to rat mGlu1a receptor CHO-dhfr$^-$ membranes. Scatchard Plots were linear, indicating the presence of a single, saturable, high affinity binding site. Non-linear regression analysis of the rectangular hyperbola revealed a $B_{max}$ of 6512±1501 fmoles/mg of protein and a $K_D$ of 0.90±0.14 nM (n=3).

Figure 6:
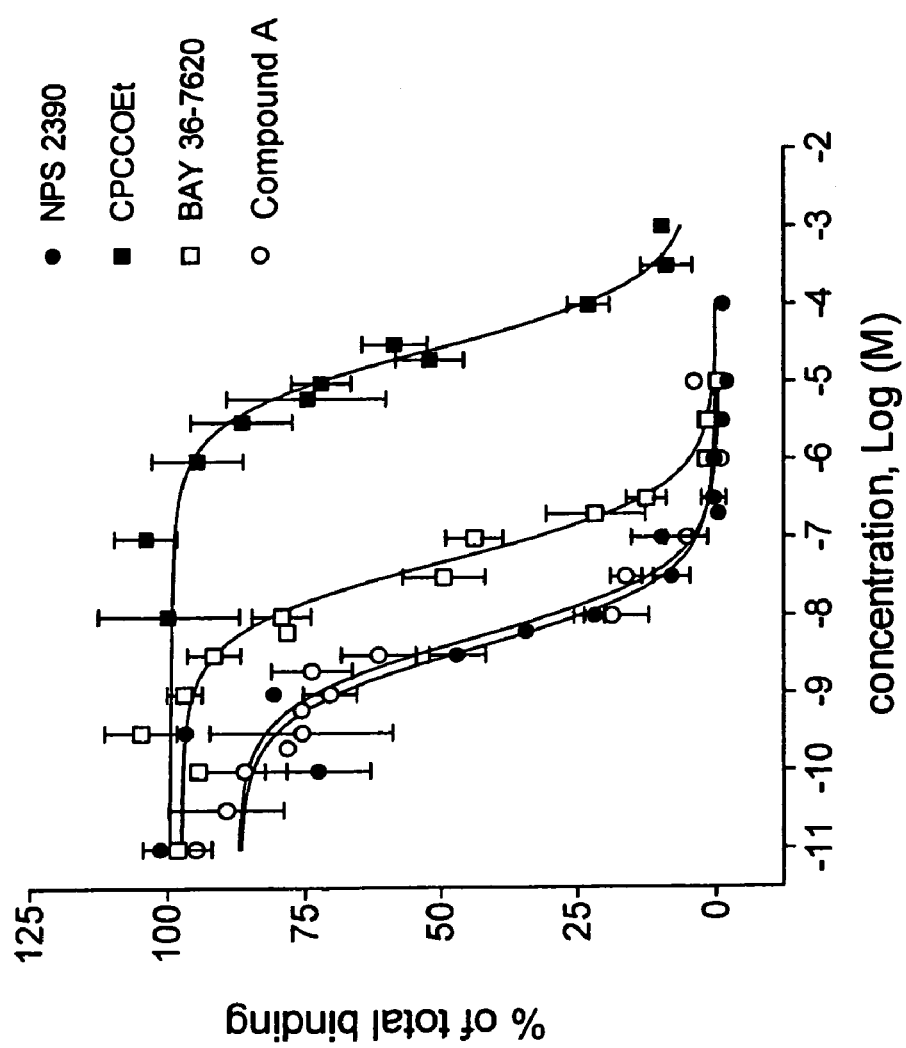

A series of mGlu1 receptor agonists and antagonists was tested for inhibition of [$^3$H]Compound A-binding to rat mGlu1a receptor CHO-dhfr$^-$ membranes. Inhibition curves for some antagonists are shown in FIG. 6, and the $K_i$ values of all compounds tested are listed in Table 11.

TABLE 11

Potencies of various mGlu1 receptor agonists and antagonists in inhibition of [$^3$H]Compound A-binding to rat mGlu1a receptor CHO-dhfr$^-$ membranes. $K_i$ values and Hill coefficients are mean ± SD of 3–4 independent experiments.

| compound | $K_i$ (nM) | Hill coefficient |
| --- | --- | --- |
| Compound A | 1.35 ± 0.99 | 0.94 ± 0.04 |
| NPS 2390 | 1.36 ± 0.50 | 0.97 ± 0.02 |
| BAY 36-7620 | 11.2 ± 0.93 | 0.95 ± 0.02 |
| CPCCOEt | 4,900 ± 170 | 0.93 ± 0.03 |
| glutamate | >1,000,000 | |
| quisqualate | >1,000,000 | |
| 1S,3R-ACPD | >1,000,000 | |
| (S)-3,5-DHPG | >1,000,000 | |
| LY367385 | >1,000,000 | |
| (S)-4C3HPG | >1,000,000 | |
| AIDA | >1,000,000 | |
| (S)-4CPG | >1,000,000 | |
| MCPG | >1,000,000 | |

Remarkably, all ligands that bind to the glutamate binding site, i.e. glutamate, quisqualate, 1S,3R-ACPD, (S)-3,5-DHPG, LY-367385, (S)-4C-3HPG, (S)-4CPG, MCPG and AIDA did not inhibit [$^3$H]Compound A binding. In contrast, the non-competitive mGlu1 receptor antagonists CPCCOEt, BAY 36-7620, NPS 2390 and compound A inhibited [$^3$H]Compound A binding to rat mGlu1a receptor CHO-dhfr$^-$ membranes with potencies, generally consistent with their potencies to inhibit mGlu1a receptor function. compound A and NPS 2390 showed the highest affinity, with a $K_i$ of 1.35±0.99 and 1.36±0.50 nM, respectively. BAY 36-7620 inhibited the binding also at nanomolar concentrations, whereas CPCCOEt displaced at micromolar concentrations.

We also investigated the specificity of [$^3$H]Compound A binding towards the mGlu1 versus mGlu2, -3, -4, -5, and -6 receptors. Using [$^3$H]LY341495, 95, 98 and 40% specific binding was found when using membranes prepared from CHO-dhfr$^-$ cells expressing the mGlu2, mGlu3, or mGlu6 receptor, respectively. [$^3$H]MPEP was used as a positive control for the mGlu5 receptor and produced 95% specific binding to rat mGlu5 receptor containing membranes. Total binding of 20 nM [$^3$H]Compound A to membranes prepared from CHO-dhfr$^-$ cells expressing the rat mGlu2, -3, -4, -5, or -6 receptor was not higher than the binding to membranes from wild-type CHO-dhfr$^-$ cells, nor was it higher than the non-specific binding to rat mGlu1a receptor CHO-dhfr$^-$ membranes. Furthermore, specific binding of [$^3$H]Compound A to these membranes was investigated using various blancs: 1 μM compound 135, which is expected to bind to the same site as compound A, glutamate and L-SOP, which bind to the glutamate binding pocket and MPEP that binds to an allosteric site on the mGlu5 receptor (see Table 12). None of these blancs displaced [$^3$H]Compound A. Together, these data demonstrate the specificity of [$^3$H] Compound A for the mGlu1 receptor relative to mGlu2, -3, -4, -5 and -6 receptor subtypes.

TABLE 12

[$^3$H]Compound A is specific for the mGlu1 receptor relative to the mGlu2, −3, −4, −5 or −6 receptor. The specific binding of 20 nM [$^3$H]Compound A to 40 μg membranes from wild-type (CHO-dhfr$^-$) cells or from CHO-dhfr$^-$ cells expressing rat mGlu2, −3, −4, −5, or −6 receptors is compared to binding of 10 nM [$^3$H]Compound A to 20 μg rat mGlu1a receptor CHO-dhfr$^-$ membranes. Various compounds were used to define non-specific binding. Specific binding (SB) data from rat mGlu1a receptor CHO-dhfr$^-$ membranes are the mean ± SD of 3 experiments performed in duplicate. Other SB data are the mean of duplicate determinations from one experiment (ND = not determined).

| SB (fmoles/mg protein) | mGlu1 | wild-type | mGlu2 | mGlu3 | mGlu4 | mGlu5 | mGlu6 |
| --- | --- | --- | --- | --- | --- | --- | --- |
| Compound 135 as blanc | 6057 ± 1456 | 65 ND | 0 | 0 | 82 | 38 | 0 |
| various blancs | ND | | 34[a] | 0[a] | 57[b] | 0[c] | 0[a] |

Figure 7:
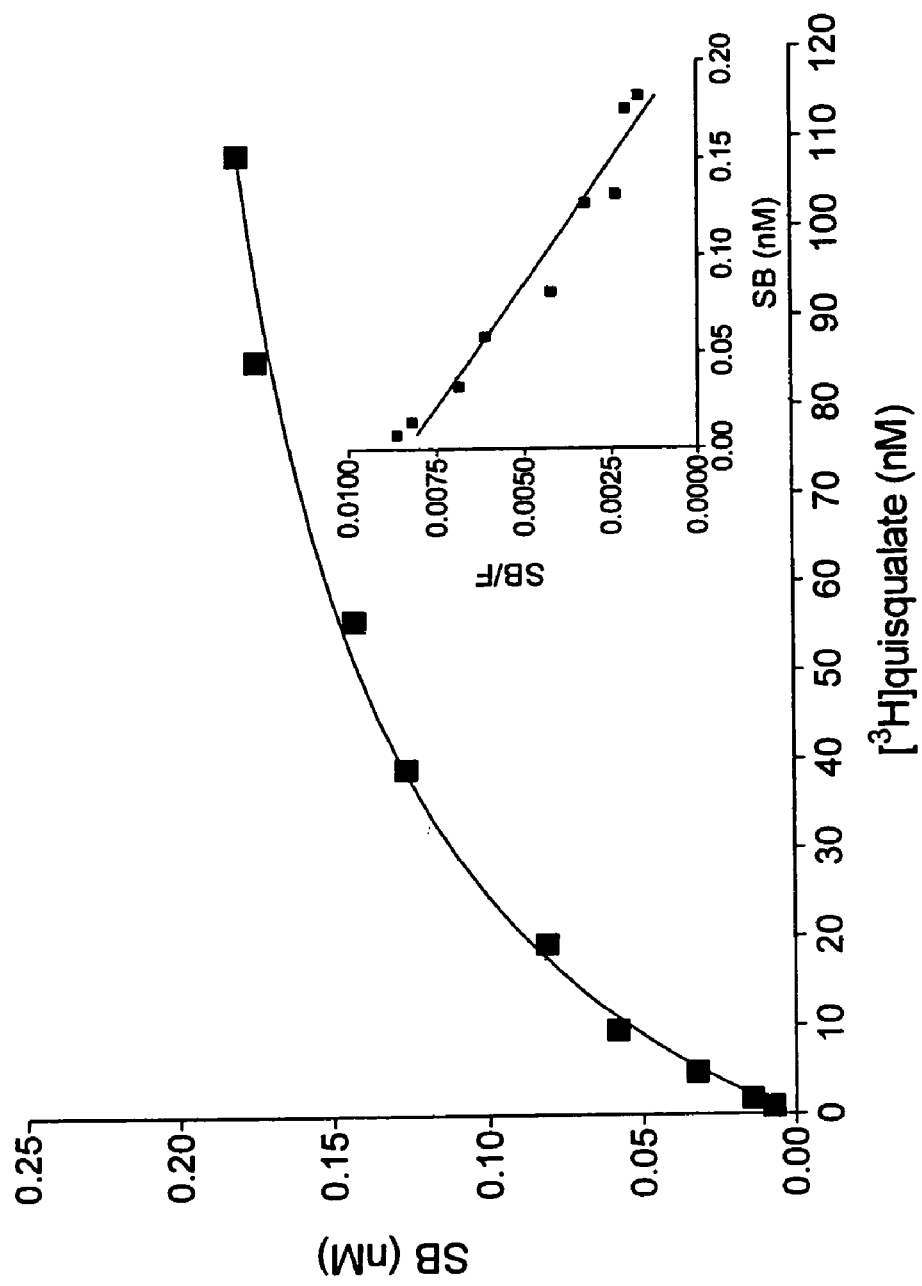

[a] 1 mM glutamate was used to determine non-specific binding
[b] 0.1 mM L-SOP was used to determine non-specific binding
[c] 10 μM MPEP was used to determine non-specific binding Comparison with [³H]quisqualate binding. Saturation binding experiments were performed using 30 μg protein per incubate and 10 concentrations (1, 2, 5, 10, 20, 40, 60, 90, 120 and 150 nM) of the mGlu1 receptor agonist [³H]quisqualate (FIG. 7). Fitting of the curves revealed a single binding site with $K_D$ and $B_{max}$ values of 22.0±10 nM and 3912±436 fmoles/mg protein, respectively (n=3). Clearly, [³H]Compound A bound to mGlu1a with a much higher affinity than [³H]quisqualate does. The number of binding sites labelled with [³H]quisqualate was ~60% of the number of binding sites labelled by [³H]Compound A.

The same compounds were evaluated for their inhibitory action on [³H]quisqualate binding to rat mGlu1a receptor CHO-dhfr⁻ membranes. Inhibitory potencies of the tested agonists and antagonists as well as Hill coefficients are summarized in Table 13. In this case, the compounds known to exert a competitive interaction with glutamate, inhibited [³H]quisqualate binding, whereas CPCCOEt, BAY 36-7620 and NPS 2390 did not affect [³H]quisqualate binding. Also compound A did not displace binding of [³H]quisqualate to the rat mGlu1a receptor. The competitive mGlu1 receptor ligands displaced [³H]quisqualate binding with the following rank order of potency: quisqualate>glutamate>LY367385>(S)-3,5-DHPG>(S)-4C-3HPG>1S,3R-ACPD>(S)-4CPG>AIDA>MCPG.

non-competitive compounds all displaced [³H]Compound A binding without affecting the binding of [³H]quisqualate suggested that these antagonists bound another site than the glutamate binding site. In order to assess whether the reference compounds CPCCOEt, BAY 36-7620, NPS 2390 and the newly identified mGlu1 receptor antagonist compound A compete for the same site or mutually exclusive sites, saturation experiments with [³H]Compound A concentrations from 0.2 to 20 nM in the absence and the presence of CPCCOEt (30 μM), BAY 36-7620 (100 nM) and NPS 2390 (10 nM) were performed. The presence of these competitors did not affect the $B_{max}$ values, but caused a significant increase in the $K_D$ value of [³H]Compound A (Table 14). This is visualized in FIG. 8, where the data are plotted using linear regression. In Scatchard plots, the obtained linear lines indeed merge to the same intercept on the X-axis (i.e. the $B_{max}$ value).

TABLE 14

$K_D$ and $B_{max}$ values obtained from analyses of [³H]Compound A saturation binding curves obtained in the absence and presence of the mGlu1 receptor antagonists CPCCOEt (30 μM), BAY 36-7620 (100 nM) and NPS 2390 (10 nM). Values are mean ± SD from 3 individual experiments. Statistical analysis was performed using the Student's t-test (two-tailed): p < 0.01 and *p < 0.001.

|  | control | CPCCOEt | BAY 36-7620 | NPS 2390 |
| --- | --- | --- | --- | --- |
| $K_D$ (nM) | 0.73 ± 0.09 | 3.17 ± 0.90** | 5.21 ± 1.2** | 2.90 ± 0.20*** |
| $B_{max}$ (fmoles/mg protein) | 7284 ± 970 | 7009 ± 1231 | 5872 ± 1018 | 6887 ± 2804 |

TABLE 13

Potencies of various mGlu1 receptor agonists and antagonists in inhibition of [³H]quisqualate binding to rat mGlu1a receptor CHO-dhfr⁻ membranes. $K_i$ values and Hill coefficients are mean ± SD of 2 independent experiments.

| compound | $K_i$ (μM) | Hill coefficient |
| --- | --- | --- |
| quisqualate | 0.030 ± 0.00 | 0.98 ± 0.01 |
| glutamate | 0.40 ± 0.07 | 0.99 ± 0.01 |
| LY367385 | 1.18 ± 0.47 | 0.99 ± 0.01 |
| (S)-3,5-DHPG | 1.42 ± 0.00 | 0.97 ± 0.00 |
| (S)-4C3HPG | 1.65 ± 0.06 | 0.98 ± 0.02 |
| 1S,3R-ACPD | 1.92 ± 0.20 | 0.97 ± 0.01 |
| (S)-4CPG | 4.51 ± 0.78 | 0.98 ± 0.00 |
| AIDA | 98.3 ± 15.4 | 0.98 ± 0.03 |
| MCPG | 165 ± 0.47 | 0.96 ± 0.02 |
| Compound A | >1,000 |  |
| NPS 2390 | >1,000 |  |
| BAY 36-7620 | >1,000 |  |
| CPCCOEt | >1,000 |  |

Nature of competition between CPCCOEt, BAY 36-7620, NPS 2390 and [³H]Compound A binding. The fact that the

Figure 9:
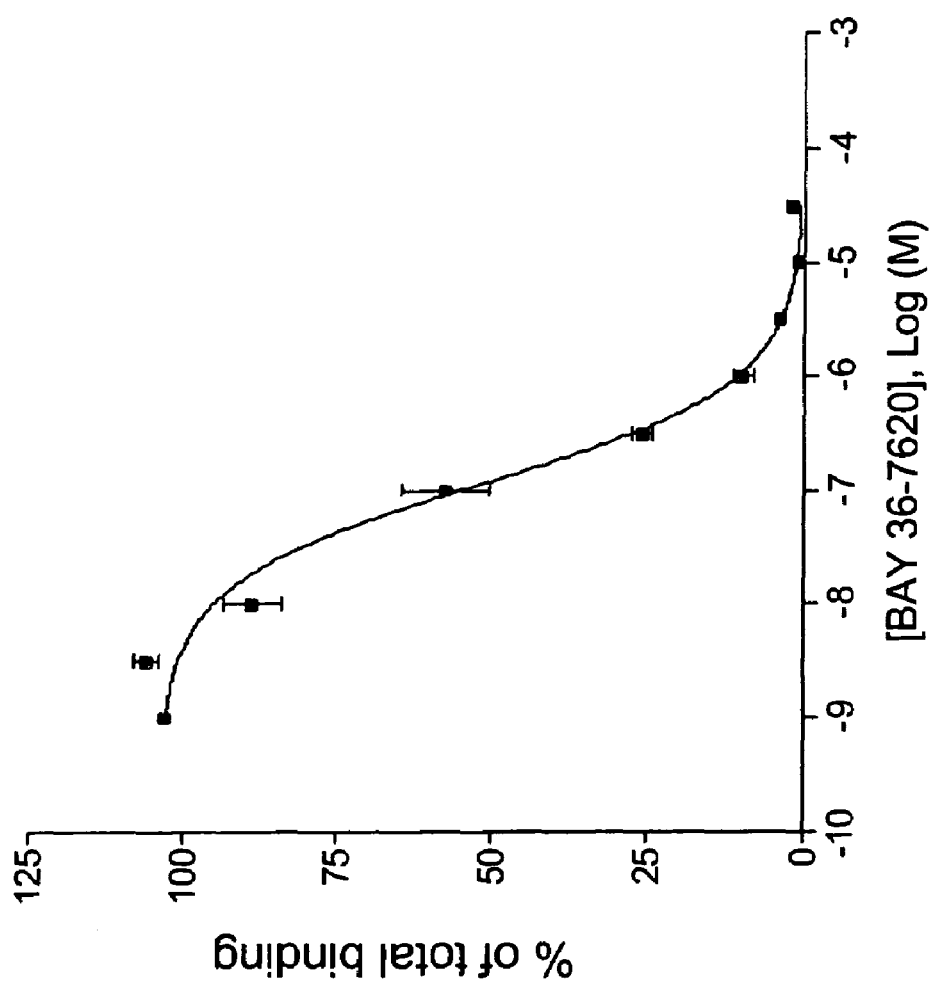

[³H]Compound A binding in rat brain membranes and sections. We used the specific mGlu1 receptor radioligand [³H]Compound A to examine receptor binding in different regions of the rat brain. Membranes from rat cortex, striatum, cerebellum and hippocampus were prepared and [³H]Compound A binding was measured. Non-specific binding compared to total binding was 10% in cerebellum, 30% in hippocampus and 25% in cortex and striatum. $K_D$ and $B_{max}$ values were determined for each brain region (Table 15). $K_D$ values were about 1 nM for all structures. The $B_{max}$ values were significantly different among the various areas. [³H]Compound A labelled a remarkably high number of mGlu1 receptors in the cerebellum. In the striatum and hippocampus about 16% of the number of sites found in the cerebellum were labelled. Only 11% of the number of binding sites in the cerebellum was bound in the rat cortex. Importantly, also incubation with 10 μM of the structurally unrelated compound BAY 36-7620 maximally inhibited [³H]Compound A binding (FIG. 9). The mGlu5 receptor selective compound MPEP (tested up to 30 μM) did not affect [³H]Compound A binding to rat cerebellar membranes, again showing the mGlu1 receptor selectivity of compound A.

Figure 10:
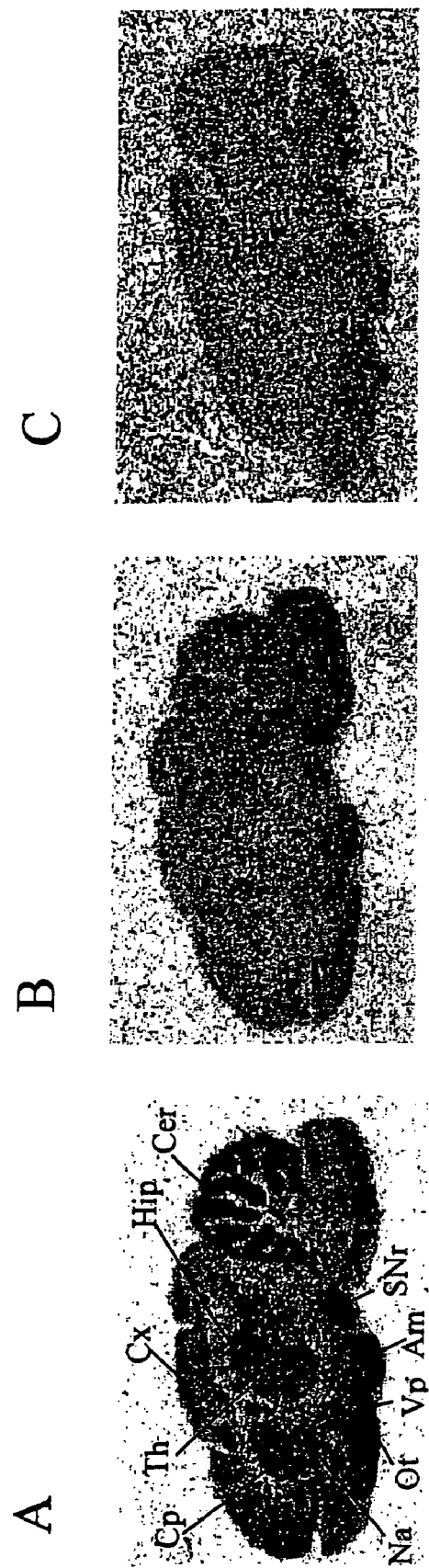

Using radioligand autoradiography, we examined [³H]Compound A binding distributions in rat brain sections in further detail (FIG. 10). [³H]Compound A autoradiography was investigated in sagittal rat brain sections; non-specific binding was determined using compound 135 (FIG. 10, panel A). Very high specific binding was observed in the molecular layer of the cerebellum. A moderate signal was observed in the CA3 field and dentate gyrus of the hippocampal formation, thalamus, olfactory tubercle, amygdala and substantia nigra reticulata. The cerebral cortex, caudate putamen, ventral pallidum, nucleus accumbens showed lower labelling.

Also incubation with BAY 36-7620 completely inhibited [³H]Compound A binding to rat brain sections (FIG. 10, panel C).

TABLE 15

Equilibrium binding constants of [³H]Compound A-binding to membranes from rat cortex, hippocampus, striatum and cerebellum. $K_D$ and $B_{max}$ values are mean ± SD derived from 3 independent experiments.

|  | cortex | hippocampus | striatum | cerebellum |
| --- | --- | --- | --- | --- |
| $K_D$ (nM) | 1.04 ± 0.40 | 0.72 ± 0.22 | 0.84 ± 0.23 | 0.99 ± 0.36 |
| $B_{max}$(fmoles/mg protein) | 471 ± 68 | 688 ± 125 | 741 ± 48 | 4302 ± 2042 |

Discussion

Up to now, only a few mGlu1 receptor subtype selective antagonists have been found. The mGlu1 receptor has been shown to be selectively blocked by CPCCOEt (Litschig et al., *Mol. Pharmacol.* 55:453-461, 1999) and BAY 36-7620 with potencies that vary from micromolar for CPCCOEt (6.6 μM) to high nanomolar concentrations for BAY 36-7620 (160 nM). In the present study, compound A is identified as a novel mGlu1 receptor antagonist with low nanomolar functional antagonistic potency on the rat mGlu1a receptor (21.6 nM) and the human mGlu1a receptor (10.4 nM). The antagonist action of compound A was found to be non-competitive, since the maximal glutamate-induced mGlu1 receptor activation was decreased in the presence of compound A. The observed increase in glutamate $EC_{50}$ in the presence of compound A can be explained by the presence of spare receptors. In the presence of low concentrations of a non-competitive antagonist, the concentrations-response curve will be shifted to the right since more agonist is needed to compensate for the 'nonspare' receptors that are blocked by the antagonist. These antagonist concentrations will not yet affect the maximal agonist response, while higher antagonist concentrations will eventually suppress the maximum response (Zhu et al., *J. Pharm. Tox. Meth.* 29:85-91, 1993). This phenomenon has also been reported for BAY 36-7620 (Carroll et al., *Mol. Pharmacol.* 59:965-973, 2001) and CPCCOEt (Hermans et al., *Neuropharmacology* 37:1645-1647, 1998). Our data further show that compound A may act as an inverse agonist towards the mGlu1a receptor and that compound A acts selectively on the mGlu1 receptor with regard to other mGlu receptor subtypes and ionotropic glutamate receptors. Signal transduction data showed that compound A does not display agonist, antagonist or positive allosteric action on the mGlu2, -3, -4, -5 and -6 receptor and radioligand binding studies revealed that [³H]Compound A does not bind to the mGlu2, -3, -4, -5 and -6 receptor, furthermore excluding the possibility that compound A acts as a neutral ligand at any of these receptor types. The lack of selective mGlu1 receptor radioligands together with the interesting pharmacological properties of compound A were compelling reasons to label compound A for the investigation of mGlu1 receptors in binding studies.

[³H]Compound A binding met all the requirements for a ligand very well suited to study binding properties, pharmacology and distribution of mGlu1 receptors. First, [³H]Compound A binding studies were performed in rat mGlu1a receptor CHO-dhfr⁻ membranes. Specific binding was very high and increased linearly with protein concentration (FIG. 2). Specific binding showed a modest increase in the presence of $MgCl_2$ and $CaCl_2$, whereas binding decreased by 22% at pH 6 and was unaffected by an increase in pH. In regard to the effects of pH on binding, it is worth noting the calculated physicochemical properties of compound A: calculated $pK_a$ and clogP are 6.2 and 4.5, respectively. At pH 7.4, the degree of ionisation of compound A is thus very low (only 5.9%). The percentage of ionisation decreases further at higher pH (1.6% at pH 8, 0.2% at pH 9 and no protonation at pH 10). The clogD value remains 4.5 from pH 7.4 to pH 10. At pH 6, however, 61.3% of compound A is in the protonated form. Accordingly, the clogD decreases to 4.1. The lower binding of the ligand in ionised form suggests that the non-ionised ligand has the highest binding affinity. This is remarkable, and is in contrast with findings for ligands for mono-amine G protein-coupled receptors (e.g. the dopamine receptor), which are often strong bases and bind in a cationic form. For such compounds, the driving force for the binding to the receptor is electrostatic in nature (Van de Waterbeemd et al., *J. Med. Chem.* 29:600-606, 1986). Our data may indicate that ionic interactions are not a driving force in the binding to the receptor, and that there is neither a contribution of ionic surface effects. Additionally, although compound A is a strong lipophilic compound, the very low non-specific [³H]Compound A binding might be due to the fact that no electrostatic interaction can take place between the non-ionised form of compound A and the negatively charged cell membrane. Binding was temperature dependent, and increased substantially at 4° C. (FIG. 3). By virtue of its fast association and dissociation kinetics, binding equilibrium was rapidly reached. [³H]Compound A labelled apparently a single population of sites with a very high affinity ($K_D$=0.90±0.14 nM). In contrast, [³H]quisqualate, the mGlu1 receptor radioligand of choice up to now, exhibited a much higher $K_D$ value of 22.0±10 nM, which correlated well with the value of 37 nM obtained by Mutel et al., *J. Neurochem,* 75:2590-2601, 2000. Besides the considerable higher affinity, [³H]Compound A labelled significantly more (~40%) binding sites than [³H]quisqualate. $B_{max}$ values of 6512±1501 fmoles/mg of protein and 3912±436 fmoles/mg protein were found for [³H]Compound A and [³H]quisqualate, respectively. This discrepancy can be explained on the basis of the G protein coupling of the receptor. Agonists facilitate the coupling of the receptor to the G protein, which results in a receptor conformation with high affinity for agonists. According to this theory, a full agonist such as quisqualate would predominantly label the high affinity or G protein-coupled receptor state. An antagonist would have equal affinity for coupled and uncoupled receptors, and thus for both the high and low affinity states of the receptor. Our finding that the $B_{max}$ for [³H]Compound A is considerably higher than for [³H]quisqualate is in line with this theory.

A striking finding in this study was that the natural agonist glutamate and also quisqualate were unable to inhibit [³H]Compound A binding to rat mGlu1a receptor CHO-dhfr⁻ membranes, whereas CPCCOEt, BAY 36-7620, NPS 2390 and compound A, known as non-competitive antagonists, all inhibited [³H]Compound A binding to the same maximal level (FIG. 6). Inhibition of [³H]Compound A binding by the latter compounds followed sigmoidal curves with Hill coefficients of about 1.0 (Table 11), which gave no indication for binding to multiple sites. It is important to mention that although a structurally related analogue was used to define non-specific binding, a similar low non-specific binding was obtained with structurally unrelated compounds such as BAY 36-7620 when used at 1 μM or more in rat mGlu1a receptor CHO-dhfr⁻ membranes (FIG. 6). For [³H]quisqualate, all the amino acid-like structures, known as competitive ligands, could displace [³H]quisqualate from its binding site. Inhibitory potencies of quisqualate, glutamate, LY367385, (S)-3,5-DHPG, (S)-4C-3HPG, 1S, 3R-ACPD, (S)-4CPG, AIDA and MCPG (Table 13) were in good agreement with the values reported by Mutel et al. *J. Neurochem.* 75:2590-2601, 2000. In contrast, the above non-competitive compounds did not affect its binding. For CPCCOEt, it has been reported that it does not affect [$^3$H]glutamate binding to membranes prepared from rat mGlu1a receptor-expressing cells (Litschig et al., *Mol. Pharmacol.* 55:453-461, 1999). Furthermore, it has been suggested that CPCCOEt does not bind to the glutamate binding site, but interacts with Thr815 and Ala818 in transmembrane domain VII. CPCCOEt is proposed to interfere with receptor signalling by disrupting an intramolecular interaction between the glutamate-bound extracellular domain and the transmembrane domain VII. Caroll et al. in *Mol. Pharmacol.* 59:965-973, 2001 demonstrated that BAY 36-7620 did not displace [$^3$H]quisqualate from the glutamate binding pocket. Transmembrane helices 4 to 7 were shown to play a crucial role for binding of BAY 36-7620. Our inhibition experiments performed with [$^3$H]Compound A and [$^3$H]quisqualate suggest that CPCCOEt, BAY 36-7620, NPS 2390 bind to the same site as compound A. Saturation experiments using [$^3$H]Compound A in the absence and the presence of 30 µM CPCCOEt, 100 nM BAY 36-7620 and 10 nM NPS 2390 further support that these compounds bind to the same or mutually exclusive sites. $K_D$ values significantly increased, whereas the $B_{max}$ value was unaltered (Table 14). These results indicate that although the affinity of [$^3$H]Compound A decreases, high concentrations of [$^3$H]Compound A are still able to displace binding of the another compound from its binding site, which is a typical property of a competitive interaction. In conclusion, our data support the notion that CPCCOEt, BAY 36-7620, NPS 2390 and compound A act on a site different from the glutamate binding pocket, presumably they compete for the same transmembrane segment VII.

Previous group I mGlu receptor binding studies in brain were performed using [$^3$H]glutamate or [$^3$H]quisqualate (Schoepp and True, *Neurosci. Lett* 145:100-104, 1992; Wright et al., *J. Neurochem.* 63:938-945, 1994; Mutel et al., *J. Neurochem.* 75:2590-2601, 2000). These radioligands have the disadvantage of labelling more than one type of glutamate receptor. Therefore, selective inhibitors had to be added to the incubation buffer to prevent labelling to other metabotropic or ionotropic glutamate receptor subtypes. To date, there is no radioligand available to specifically study the binding and distribution of the mGlu1 receptor. The specific mGlu1 receptor labelling of [$^3$H]Compound A makes it particularly useful for the investigation of native mGlu1 receptors in rat or human brain. Experiments using rat cortex, hippocampus, striatum and cerebellum membranes revealed that [$^3$H]Compound A specific binding, defined in the presence of 1 µM compound 135, was high, especially in the cerebellum (only 10% non-specific binding). Saturation experiments showed that [$^3$H]Compound A again labelled apparently a single binding site with very high affinity. $K_D$ values of about 1 nM were found for all the different brain areas (Table 15). A striking difference in $B_{max}$ values was found: a large population of binding sites was labelled in the cerebellum, whereas in hippocampus, striatum and cortex moderate to low levels of receptor expression were detected.

Because of its specificity, [$^3$H]Compound A proved to be particularly suitable for investigation of mGlu1 receptor distribution in brain sections using radioligand autoradiography. mGlu1 receptor autoradiography revealed that the highest level of mGlu1 specific binding was present in the molecular layer of the cerebellum. The granule cell layer was very weakly labelled. These results were also found by Mutel et al. in *J. Neurochem.* 75:2590-2601, 2000 who investigated group I mGlu receptor distribution using [$^3$H]quisqualate. In the hippocampal formation, the CA3 dendritic field together with the molecular layer of the dentate gyrus showed abundant labelling. The CA1 area showed very weak [$^3$H]Compound A binding, corresponding well with immunohistochemistry data from Lujan et al., *Eur. J. Neurosci.* 8:1488-1500, 1996 and Shigemoto et al., *J. Neurosci.* 17:7503-7522, 1997, who showed that in CA1 dendritic fields, an antibody specific for the mGlu5 receptor but not a specific mGlu1 receptor antibody yielded intense immunolabelling. Autoradiography experiments using [$^3$H]quisqualate indeed revealed staining in both the CA1 and CA3 region of the hippocampus, indicating binding to both the mGlu1 and mGlu5 receptor, respectively (Mutel et al., *J. Neurochem.* 75:2590-2601, 2000). [$^3$H]Compound A binding was also quite high in the thalamus, olfactory tubercle, amygdala and substantia nigra reticulata and was somewhat lower in the cerebral cortex, caudate putamen, nucleus accumbens and ventral pallidum. The same structures were labelled using [$^3$H]quisqualate (Mutel et al., *J. Neurochem.* 75:2590-2601, 2000). Also immunocytochemical findings on the cellular localization of the mGlu1a receptor, using an antibody selective for the mGlu1a receptor, were generally consistent with our data (Martin et al., *Neuron.* 9:259-270, 1992). Since [$^3$H]Compound A is expected to label all mGlu1 receptor splice variants known to date, the distribution of 1 splice variant may however differ from that of our radiolabel. For example, in the CA3 region and the caudate putamen, which are labelled by the radioligand, mGlu1b receptor but no or little mGlu1a receptor immunoreactivity was found (Martin et al., *Neuron.* 9:259-270, 1992; Shigemoto et al., *J. Neurosci.* 17:7503-7522, 1997; Ferraguti et al., *J. Comp. Neur.* 400:391-407, 1998). An important point in the demonstration of the identity of the [$^3$H]Compound A-labeled sites was the finding that the structurally different compound BAY 36-7620 also fully displaced [$^3$H]Compound A binding to rat brain membranes (FIG. 9) as well as to brain sections (FIG. 10), providing a good guarantee that the inhibited binding is purely receptor specific and not related to a structural moiety of the radioligand.

In this application, we have shown that [$^3$H]Compound A is an excellent radioligand to study mGlu1 receptors in an heterologous expression system, rat brain homogenates and brain sections. We can conclude that because of its minimal non-specific binding, its high binding affinity and marked selectivity, [$^3$H]Compound A is the ligand of choice for further exploration of the mGlu1 receptor. [$^3$H]Compound A opens perspectives for a detailed investigation of subcellular and cellular localization of the mGlu1 receptor and for the study of the functional role and regulation of the receptor in various areas.

LIST OF FIGURES

FIG. 1: Antagonist profile of Compound A. Inhibition of glutamate (30 µM)-induced $Ca^{2+}$ mobilization in CHO-dhfr$^-$ cells expressing the rat mGlu1a receptor is shown in FIG. 1A. Data are expressed as percentage of the signal obtained using 30 µM glutamate, which was set at 100% and are mean±SD of 3 experiments. FIG. 1B shows a concentration-response curve of glutamate alone or together with 20 nM, 30 nM, 60 nM, 100 nM and 1 µM Compound A. Values are mean±SD of triplicate determinations within 1 experiment. An additional experiment showed the same results. FIG. 1C shows basal IP accumulation in the presence of increasing concentrations of Compound A. Values are expressed as percentage of basal IP production in the presence of solvent, which was set as 100% and are mean±SD of 3 experiments performed in quadruplicate.

FIG. 2: Specific [³H]Compound A binding is linear with amount of membrane protein. 10 to 50 μg rat mGlu1a receptor CHO-dhfr⁻ membranes was incubated for 30 min on ice with 2.5 nM [³H]Compound A. Data are expressed as mean±SD of triplicate determinations and are from a representative experiment.

FIG. 3: Association time-course curve for [³H]Compound A binding to rat mGlu1a receptor CHO-dhfr⁻ membranes. Association kinetics were measured by adding 2.5 nM [³H] Compound A at different times before filtration and was determined at 3 different temperatures. Data are mean±SD of 3 independent experiments performed in duplicate.

FIG. 4: Time-course for dissociation of [³H]Compound A to rat mGlu1a receptor CHO-dhfr⁻ membranes at 4° C. and 25° C. Samples were incubated for 30 min at 4° C. or 25° C., then an excess of compound 135 was added, followed by rapid filtration at the time indicated for each data point. Values are mean±SD of 2 independent experiments performed in duplicate.

FIG. 5: Representative saturation binding curve and Scatchard Plot of [³H]Compound A binding to rat mGlu1a receptor CHO-dhfr⁻ membranes. Specific binding (SB) was obtained by calculating the difference between total binding (TB) and non-specific binding (BL), measured in the presence of 1 μM compound 135. For each experiment, data points were determined in duplicate. The experiment was repeated 3 times.

FIG. 6: Inhibition of 2.5 nM [³H]Compound A binding to rat mGlu1a receptor CHO-dhfr⁻ membranes by various mGlu receptor antagonists. Data points represent % of total binding and are mean±SD of 3-4 individual experiments.

FIG. 7: Representative saturation binding curve and Scatchard Plot of [³H]quisqualate binding to rat mGlu1a receptor CHO-dhfr⁻ membranes. For each experiment, data points were determined in duplicate. The experiment was repeated 2 times.

Figure 8:
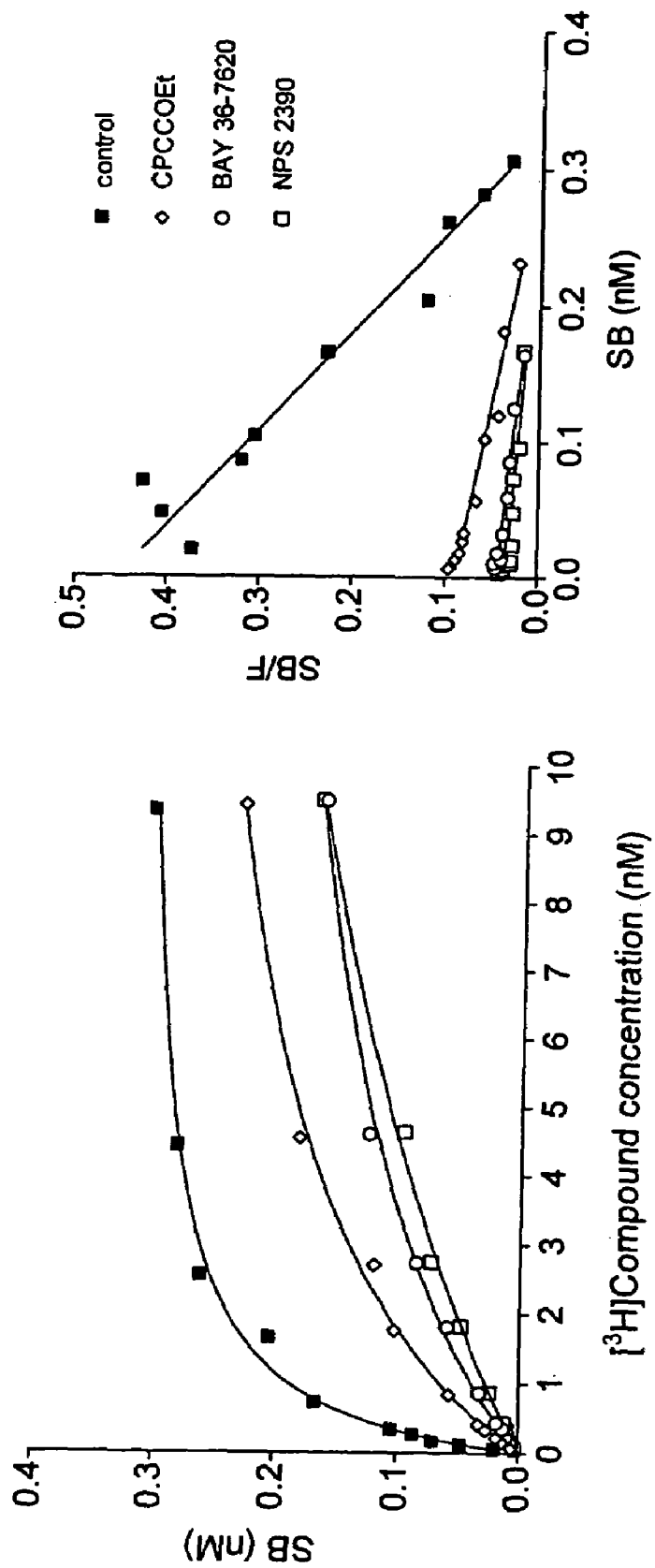

FIG. 8: Saturation binding curves and Scatchard plots of [³H]Compound A binding to rat mGlu1a receptor CHO-dhfr⁻ membranes in the absence and presence of CPCCOEt (30 μM), BAY 36-7620 (100 nM) and NPS 2390 (10 nM). The graph shown is a representative of 3 independent experiments. Data are expressed in nM specifically bound. For each experiment, data points were determined in duplicate.

FIG. 9: Inhibition of 2.5 nM [³H]Compound A binding to rat cerebellar membranes by BAY 36-7620. Data points represent % of total binding and are mean±SD of 2 individual experiments.

FIG. 10: [³H]Compound A binding to sagittal rat brain sections using autoradiography. Panel A is a representative section showing total binding with 1.5 nM [³H]Compound A. Panel B is a representative and adjacent section showing non-specific binding with 1.5 nM [³H]Compound A in the presence of 1 μM compound 135. Panel C is a representative section showing non-specific binding with 1.5 nM [³H]Compound A in the presence of 10 μM BAY 36-7620. Sections from panel A and B were exposed to [³H]Hyperfilm, while the section from panel C was exposed to a Fuji Imaging plate. Th, thalamus; SNr, substantia nigra reticulata; CA3, CA3 region of the hippocampus; Dg; dentate gyrus of the hippocampus; Cer; cerebellum; Cp, caudate putamen; Cx, cerebral cortex, Ot, olfactory tubercle, Am, amygdala, Vp, ventral pallidum, Na, nucleus accumbens.

The invention claimed is:

1. A radiolabelled compound that is any one of compounds (a), (b), (c), (d) or (e):

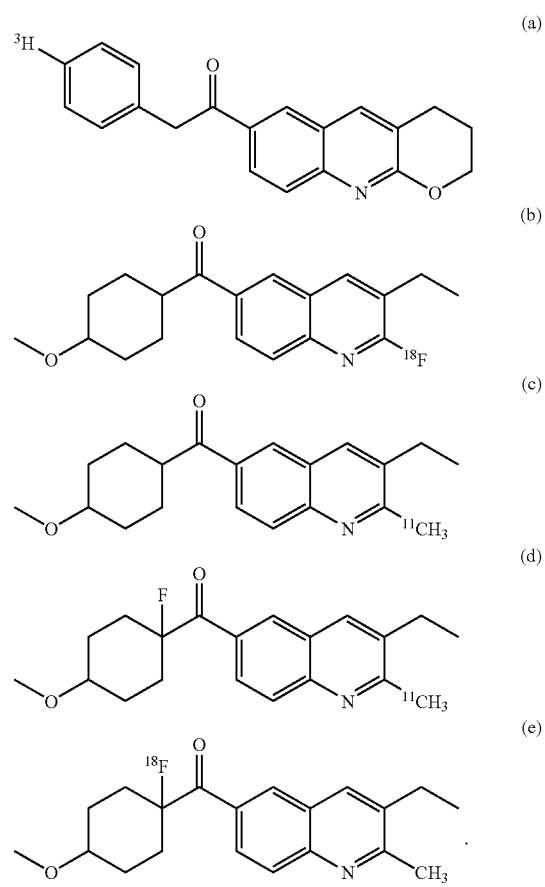

2. The radiolabelled compound according to claim 1, wherein the compound is compound (a).

3. A radioactive composition for administration to mammals for marking or identifying an mGlu1 receptor comprising a radiolabelled compound according to claim 1 and a pharmaceutically acceptable carrier or diluent.

4. A diagnostic method for detecting the presence of a mGlu1 receptor comprising
administering a radiolabelled compound according to claim 1 to biological material; and
detecting emissions from the radiolabelled compound.

5. The method of claim 4 further comprising screening a test compound for the ability to occupy or bind to a mGlu1 receptor in the biological material.

6. The method of claim 4 wherein the biological material is a tissue sample, plasma fluid, body fluid, body part from a warm-blooded animal, or organ from a warm-blooded animal.

7. A diagnostic tool for marking or identifying an mGlu1 receptor in biological material, said tool comprising a radiolabelled compound according to claim 1.

8. A diagnostic tool for screening whether a test compound has the ability to occupy or bind to a mGlu1 receptor in biological material, said diagnostic tool comprising a radiolabelled compound according to claim 1.

9. A method for imaging an organ comprising the steps of
 (a) administering a sufficient amount of a compound according to claim 1 to the organ; and
 (b) detecting the emissions from the radioactive compound.

10. The method of claim 9 wherein the compound is administered in vivo.

11. The method of claim 9 wherein the compound is administered in vitro.

12. The method of claim 9 wherein the emissions are detected using Single Photon Emission Computed Tomography or Positron Emission Tomography.

13. The method of claim 9 wherein the organ is a brain.

14. A method for marking an mGlu1 receptor comprising the steps of
    (a) administering a compound according to claim 1 to biological material; and
    (b) detecting the emissions from the radioactive compound.

15. The method of claim 14 wherein the compound is administered in vivo.

16. The method of claim 14 wherein the compound is administered in vitro.

17. The method of claim 14 wherein the emissions are detected using Single Photon Emission Computed Tomography or Positron Emission Tomography.

18. The method of claim 14 wherein the biological material is a tissue sample, plasma fluid, body fluid, body part from a warm-blooded animal, or organ from a warm-blooded animal.

19. A method of screening whether a test compound occupies or binds to an mGlu1 receptor in biological material comprising:
    (a) administering a compound according to claim 1 to biological material;
    (b) administering the test compound to the biological material; and
    (c) detecting the emissions from the radioactive compound.

20. The method of claim 19 wherein the emissions are detected using Single Photon Emission Computed Tomography or Positron Emission Tomography.

21. The method of claim 19 wherein the biological material is a tissue sample, plasma fluid, body fluid, body part from a warm-blooded animal, or organ from a warm-blooded animal.

* * * * *